United States Patent
O'Connor et al.

(10) Patent No.: US 10,238,828 B2
(45) Date of Patent: Mar. 26, 2019

(54) NASAL CANNULA, CONDUIT AND SECUREMENT SYSTEM

(75) Inventors: Mark Thomas O'Connor, Auckland (NZ); Jimmy Edward Eaton-Evans, Galway (IE); Neil Gray Duthie, Auckland (NZ); Brent Ian Laing, Auckland (NZ); Steven Charles Korner, Masterton (NZ); Laurence Gulliver, Auckland (NZ); Puqing Zhang, Auckland (NZ); Andrew Grant Niccol, Auckland (NZ); Charles William Douglas Irving, Bristol (GB); Craig Karl White, Auckland (NZ); Caroline Geraldine Hopkins, Auckland (NZ); Michael Paul Ronayne, Auckland (NZ); Callum James Thomas Spence, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 887 days.

(21) Appl. No.: 13/880,036

(22) PCT Filed: Oct. 18, 2011

(86) PCT No.: PCT/NZ2011/000218
§ 371 (c)(1),
(2), (4) Date: Sep. 18, 2013

(87) PCT Pub. No.: WO2012/053910
PCT Pub. Date: Apr. 26, 2012

(65) Prior Publication Data
US 2014/0000626 A1 Jan. 2, 2014

Related U.S. Application Data

(60) Provisional application No. 61/394,301, filed on Oct. 18, 2010, provisional application No. 61/414,316, (Continued)

(51) Int. Cl.
*A61M 16/06* (2006.01)
*A61M 16/08* (2006.01)

(52) U.S. Cl.
CPC .... *A61M 16/0683* (2013.01); *A61M 16/0666* (2013.01); *A61M 16/0688* (2014.02);
(Continued)

(58) Field of Classification Search
None
See application file for complete search history.

(56) References Cited

U.S. PATENT DOCUMENTS 2,807,262 A * 9/1957 Lew .................. A61F 13/02
602/47
3,288,136 A 11/1966 Lund
(Continued)

FOREIGN PATENT DOCUMENTS

CN 101396576 A 4/2009
EP 806217 A2 11/1997
(Continued)

OTHER PUBLICATIONS

International Search Report and Written Opionion, PCT/NZ2011/000218; dated Feb. 27, 2012; 17 pages.
(Continued)

*Primary Examiner* — Kathryn E Ditmer
(74) *Attorney, Agent, or Firm* — Knobbe, Martens, Olson & Bear, LLP

(57) ABSTRACT

Medical breathing tubes have a tubular body that defines a lumen extending between open terminal ends of the tubular
(Continued)

body. An internal form is enclosed within the lumen and supportive of the tubular body. The internal form may be a coated encapsulated internal form where the coating secures the internal form to the tubular body. The internal form may provide for a series of alternative crests and troughs of the tubular body. A patient interface and/or a securement system may be attached to the tubular body.

39 Claims, 18 Drawing Sheets

Related U.S. Application Data filed on Nov. 16, 2010, provisional application No. 61/473,584, filed on Apr. 8, 2011, provisional application No. 61/488,626, filed on May 20, 2011, provisional application No. 61/510,702, filed on Jul. 22, 2011.

(52) U.S. Cl.
CPC . *A61M 16/0875* (2013.01); *A61M 2205/0216* (2013.01); *A61M 2205/0238* (2013.01); *A61M 2205/7536* (2013.01); *A61M 2207/10* (2013.01); *A61M 2210/0618* (2013.01)

(56) References Cited

U.S. PATENT DOCUMENTS

| | | | |
|---|---|---|---|
| 3,513,844 A * | 5/1970 | Smith | A61M 16/0666 128/207.18 |
| 4,106,505 A | 8/1978 | Slater et al. | |
| 4,122,857 A | 10/1978 | Haerr | |
| 4,686,354 A * | 8/1987 | Makin | A61M 16/1075 128/204.17 |
| 4,782,832 A * | 11/1988 | Trimble | A61M 16/0666 128/204.18 |
| 4,808,160 A | 2/1989 | Timmons et al. | |
| 4,818,320 A | 4/1989 | Weichselbaum | |
| 5,061,258 A * | 10/1991 | Martz | A61F 13/023 128/898 |
| 5,163,914 A | 11/1992 | Abel | |
| 5,292,312 A | 3/1994 | Delk et al. | |
| 5,292,313 A | 3/1994 | Delk et al. | |
| 5,300,037 A | 4/1994 | Delk et al. | |
| 5,308,339 A | 5/1994 | Kalt et al. | |
| 5,672,159 A | 9/1997 | Warrick | |
| 5,682,881 A * | 11/1997 | Winthrop | A61M 16/0666 128/200.26 |
| 5,752,511 A | 5/1998 | Simmons et al. | |
| 6,206,134 B1 * | 3/2001 | Stark | A61B 7/02 181/131 |
| 6,328,038 B1 | 12/2001 | Kessler et al. | |
| 6,419,660 B1 * | 7/2002 | Russo | A61M 25/02 128/DIG. 26 |
| 6,447,486 B1 | 9/2002 | Tollini | |
| 6,536,428 B1 * | 3/2003 | Smith | A61M 16/08 128/203.17 |
| 7,178,521 B2 * | 2/2007 | Burrow | A61M 16/0816 128/202.27 |
| 7,331,348 B1 | 2/2008 | Beevers | |
| 7,469,719 B2 * | 12/2008 | Gray | A61M 16/08 128/203.26 |
| 7,793,892 B1 * | 9/2010 | Bowen | A61M 39/08 128/DIG. 26 |
| 2001/0029954 A1 | 10/2001 | Palmer | |
| 2003/0125668 A1 * | 7/2003 | Bierman | A61M 25/02 604/174 |
| 2003/0130644 A1 * | 7/2003 | Baker | A61F 13/622 604/389 |
| 2004/0260161 A1 * | 12/2004 | Melker | A61B 5/0873 600/340 |
| 2004/0261797 A1 * | 12/2004 | White | A61M 16/0666 128/206.11 |
| 2005/0033247 A1 | 2/2005 | Thompson | |
| 2005/0178383 A1 | 8/2005 | Mackie et al. | |
| 2006/0107958 A1 | 5/2006 | Sleeper | |
| 2007/0095347 A1 * | 5/2007 | Lampotang | A61B 5/0836 128/204.23 |
| 2008/0140044 A1 | 6/2008 | Beevers | |
| 2008/0190436 A1 * | 8/2008 | Jaffe | A61M 16/0666 128/207.18 |
| 2009/0078259 A1 * | 3/2009 | Kooij | A61M 16/0875 128/205.25 |
| 2009/0217492 A1 * | 9/2009 | Gallant | A44B 18/0003 24/306 |
| 2009/0320851 A1 | 12/2009 | Selvarajan et al. | |
| 2010/0000534 A1 * | 1/2010 | Kooij | A61M 16/0666 128/204.18 |
| 2010/0057034 A1 * | 3/2010 | Dennis | A61F 13/15203 604/385.05 |
| 2010/0100022 A1 | 4/2010 | Greener et al. | |
| 2010/0192957 A1 | 8/2010 | Hobson et al. | |
| 2010/0229872 A1 * | 9/2010 | Ho | A61M 16/06 128/206.25 |
| 2014/0000626 A1 | 1/2014 | O'Connor et al. | |

FOREIGN PATENT DOCUMENTS

| | | | |
|---|---|---|---|
| EP | 1481702 | 12/2004 | |
| FR | 2363423 A1 | 3/1978 | |
| GB | 813700 A | 5/1959 | |
| GB | 836407 A | 6/1960 | |
| GB | 933172 A | 8/1963 | |
| GB | 2368800 | 5/2002 | |
| GB | 2436525 | 10/2007 | |
| JP | H09-510635 | 10/1997 | |
| JP | 2000-500359 | 1/2000 | |
| JP | 2004-231516 | 8/2004 | |
| JP | 2005-40589 | 2/2005 | |
| JP | 2008-137971 | 6/2008 | |
| JP | 2009-72596 | 4/2009 | |
| JP | 2009-291615 | 12/2009 | |
| TW | M265052 U | 5/2005 | |
| TW | M301062 U | 11/2006 | |
| TW | M349271 U | 1/2009 | |
| WO | WO 92/20392 | 11/1992 | |
| WO | WO 1998/044973 A1 | 10/1998 | |
| WO | WO 2006062810 A1 * | 6/2006 | A44B 18/00 |
| WO | WO 2008/019294 | 2/2008 | |
| WO | WO 2008/100860 | 8/2008 | |
| WO | WO 2012/091967 | 7/2012 | |
| WO | WO 2013/157960 A1 | 10/2013 | |

OTHER PUBLICATIONS

UK Examination Report; GB15162878; dated Oct. 8, 2015; 8 pages.
UK Examination Report; GB15162852; dated Oct. 8, 2015; 7 pages.
UK Examination Report; GB15225840; dated Feb. 4, 2016; 8 pages.
UK Examination Report; GB15162878; dated Feb. 4, 2016; 5 pages.
UK Examination Report; GB15162852; dated Feb. 4, 2016; 5 pages.
UK Examination Report; GB15225832; dated Feb. 4, 2016; 5 pages.
UK Examination Report; GB13066352; dated Feb. 4, 2016; 3 pages.
UK Examination Report; GB16031130; dated Mar. 4, 2016; 7 pages.
UK Examination Report; GB16032922; dated Mar. 11, 2016; 6 pages.
AU Examination Report; 2011318681; dated Apr. 12, 2016; 3 pages.
Australian Government Patent Examination Report ; dated Jul. 2, 2015, 4 pages.
Japanese Examination Report and English translation; dated Aug. 19, 2015; 4 pages.
Chinese Office Action; dated Nov. 4, 2015; 8 pages.
GB Examination Report; dated Jun. 2, 2016; 2 pages.
GB Examination Report; dated May 18, 2016; 2 pages.
GB Examination Report; dated May 19, 2016; 1 page.

(56) References Cited

OTHER PUBLICATIONS

TW Search Report; English Translation; dated May 18, 2016; 1 page.
Australian Examination Report; dated Jan. 19, 2017; 4 pages.
Extended Search Report in corresponding European Patent Application No. 11834691.5, dated Apr. 3, 2017, in 9 pages.
Office Action in corresponding Chinese Patent Application No. 201180059469.7, dated May 15, 2017, in 5 pages.
Office Action in corresponding Japanese Patent Application No. 2016-166028, dated Jun. 19, 2017, in 7 pages.
Office Action in corresponding Australian Patent Application No. 2016222390, dated Jul. 3, 2017, in 3 pages.
Office Action in corresponding Australian Patent Application No. 2016203303, dated Jul. 12, 2017, in 4 pages.
Office Action in corresponding Canadian Patent Application No. 2814601, dated Aug. 8, 2017, in 5 pages.
Office Action in corresponding Chinese Patent Application No. 201610261300.4, dated Dec. 5, 2017, in 22 pages.
Office Action in corresponding Chinese Patent Application No. 201610261071.6, dated Mar. 28, 2018, in 22 pages.
Examination Report in corresponding Australian Patent Application No. 2016222390, dated Jun. 21, 2018, in 3 pages.
Examination Report in corresponding Canadian Patent Application No. 2814601, dated Jul. 13, 2018, in 5 pages.

\* cited by examiner

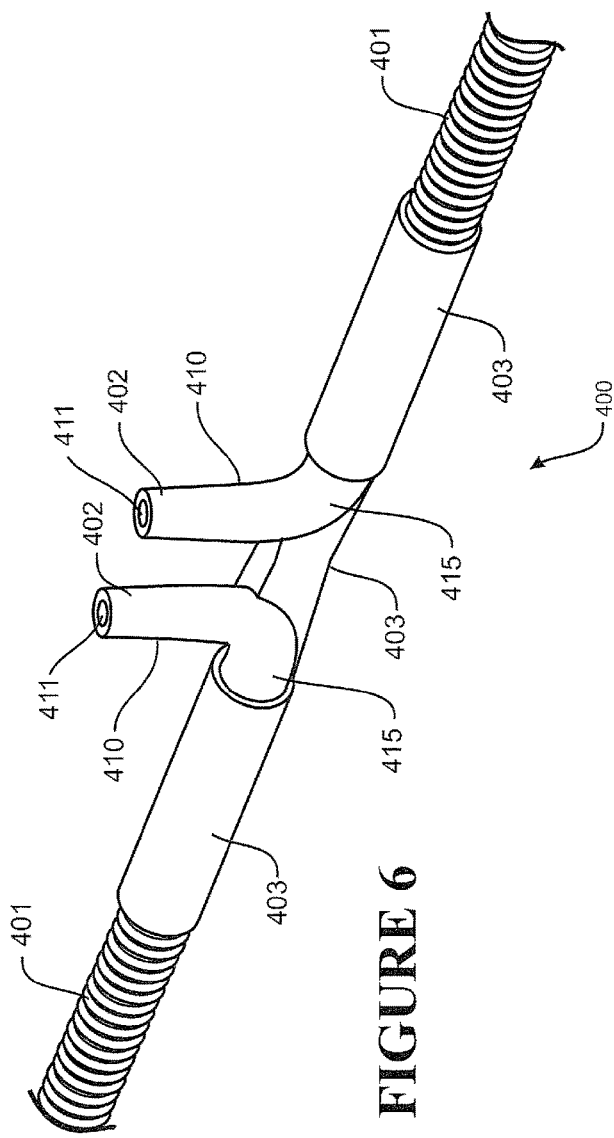
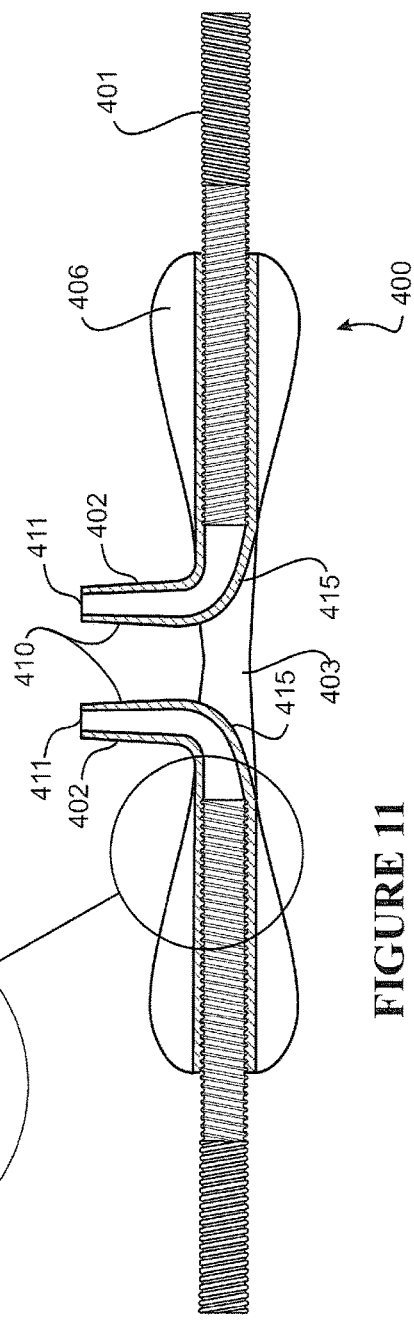
FIGURE 6
FIGURE 11

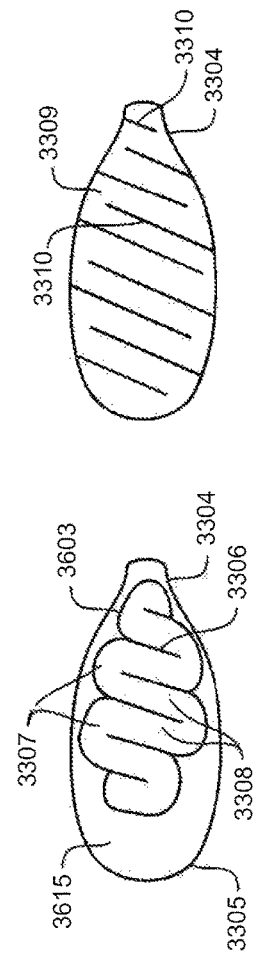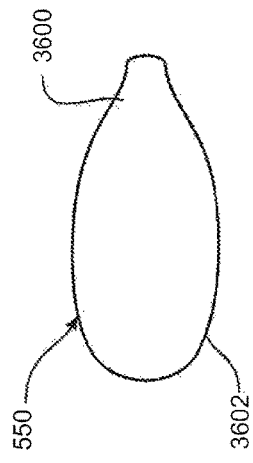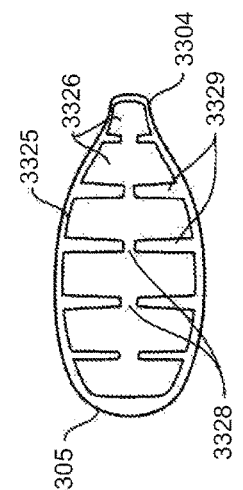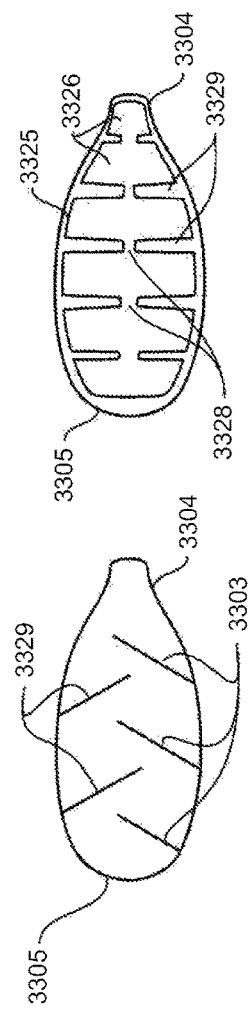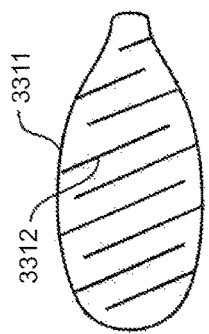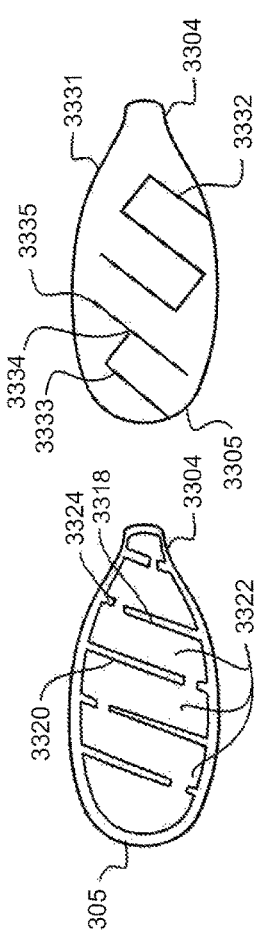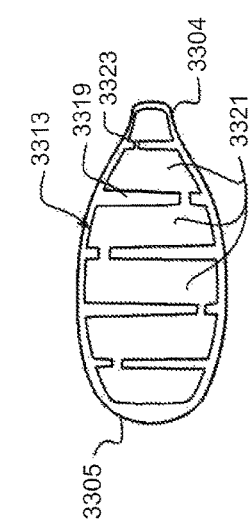
FIGURE 36a FIGURE 36b FIGURE 36c FIGURE 36d FIGURE 36e FIGURE 36f FIGURE 36g FIGURE 36h FIGURE 36i

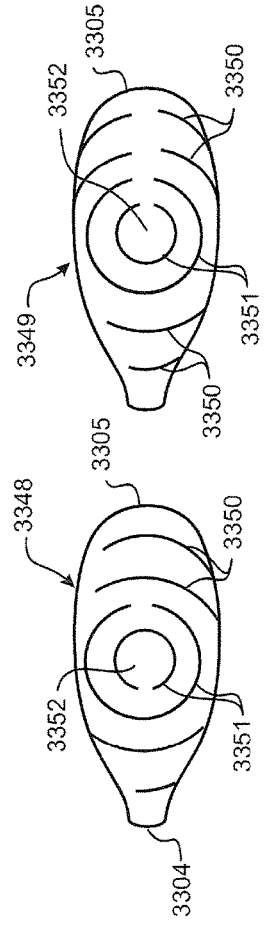
FIGURE 36j
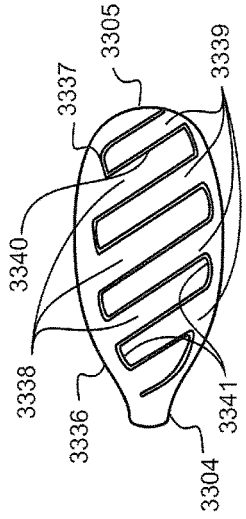
FIGURE 36m
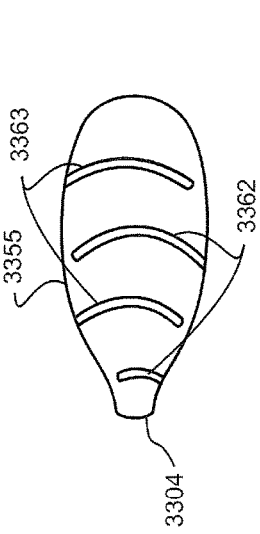
FIGURE 36k
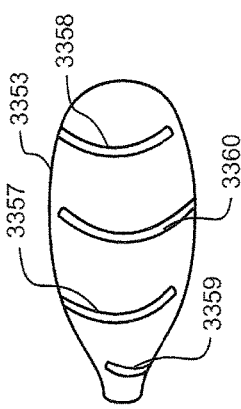
FIGURE 36n
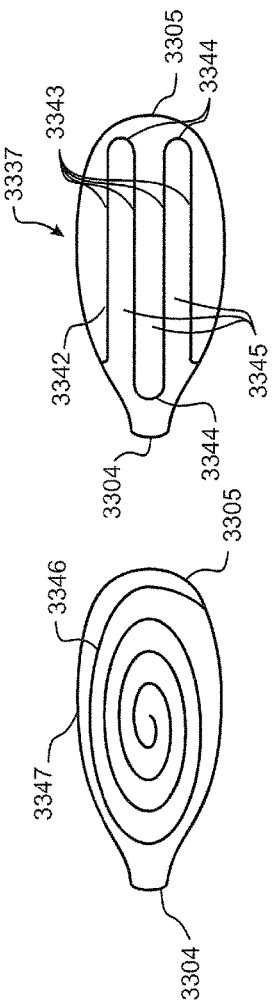
FIGURE 36l
FIGURE 36o
FIGURE 36p
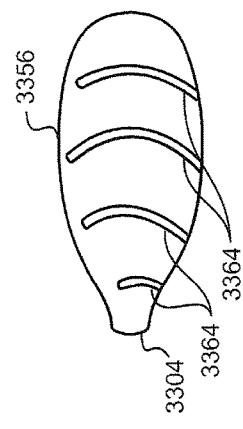
FIGURE 36q
FIGURE 36r

NASAL CANNULA, CONDUIT AND SECUREMENT SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present disclosure generally relates to components for medical systems for conveying gases to and/or from a patient. In one particular aspect, the disclosure relates to conduits, more particularly, breathing tubes for use in an inspiratory, expiratory and/or combined respiration limb of a breathing system. In another aspect, the disclosure relates to a nasal cannula and conduit that form part of a breathing system. In another aspect, the disclosure relates to nasal cannulas that form a part of a breathing system. In another aspect, the disclosure relates to a system or systems for positioning a patient interface, such as a cannula, in an operational position for and/or on a user.

Description of the Related Art

In assisted breathing, respiratory gases are supplied to a patient through a flexible breathing tube. The gases expired by the patient may be channeled through a similar breathing tube or expelled to the patient's surroundings. The gases are typically administered to the patient through a user interface, which may also comprise a short length of dedicated breathing tube to couple the interface with the supply tube. Each breathing tube is ideally lightweight, resistant to kinking or pinching, but also flexible to ensure sufficient performance and a level of comfort for the patient.

Typically, breathing tubes range in size between about 10 mm to about 25 mm in internal diameter bore (covering both neonatal and adult applications). Dedicated user interface tubes may be smaller, with an internal diameter of about 2 mm for neonatal applications. The small size of dedicated user interface breathing tubes makes them less visually intrusive and reduces the weight on the patient's face. Breathing tubes are preferably flexible so that they bend easily to improve patient comfort, which in turn can increase a patient's compliance with treatment.

In medical applications, such as assisted breathing, the gases inhaled by a patient are preferably delivered close to body temperature (usually between 33° C. and 37° C.) and with a high relative humidity (commonly near saturation). In other medical applications, such as continuous positive airway pressure (CPAP) systems or positive pressure ventilations systems that provide patient's suffering obstructive sleep apnea (OSA) with positive pressure breathing gases, the breathing gases may be heated and/or humidified to varying levels to improve user comfort or supplied without heating or humidification.

Similar tubes may also be used for supplying insufflation gases for laparoscopic surgery. These insufflation tubes are also ideally lightweight, resistant to kinking or pinching and exhibit similar flexibility to minimize obstructions and distractions within the operating theatre. The insufflation gases (typically CO2, but may be other gases or mixtures of gases) may also be humidified.

Further, gases provided to a patient can be provided via a nasal cannula. Flexibility of associated tubing becomes an important consideration, particularly in infant or neonatal situations. Improving flexibility of tubes supplying gases to a cannula of a patient assists in improved comfort, and consequently improved compliance to such gas delivery treatment.

Further, it would be advantageous to provide a system for an alternative or improved interface location or operational positioning of the interface, such as a nasal cannula. Such an alternative or improved system may further assist with improved compliance of gas delivery treatment.

In the specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

Further aspects and advantages of the present disclosure will become apparent from the ensuing description which is given by way of example only.

SUMMARY OF THE INVENTION

It is an object of the present disclosure to provide a component and/or method of manufacturing a component that will at least go some way towards improving on the above or which will at least provide the public or the medical profession with a useful choice.

In a first aspect, the disclosure broadly consists in a method of fabricating medical tubing, the method comprising providing an internal form, extruding a tubular body about the internal form, the tubular body defining a lumen enclosing the internal form.

Preferably the method further comprising:
i) applying a reduced pressure within (or to) the lumen, such that the reduced pressure draws the tubular body radially inward of the lumen and of an outer-most perimeter defined by the internal form, the outer-most perimeter of the internal form defining a plurality of alternating crests and troughs along a length of the tubular body, or
ii) applying an extension (or stretch) to at least a part or a region of the tubular body enclosing the internal form, such that release of the extension (or stretch) returns (or allows) the extended (or stretched) part or region of the tubular body to draw radially inward of the lumen and of an outer-most perimeter defined by the internal form, the outer-most perimeter defining a plurality of alternating crests and troughs along a length of the tubular body, or
iii) a combination of i) and ii).

Preferably the tubular body is provided by extrusion or by extruding a material from a die head.

Preferably the tubular body is extruded about the internal form and reduced pressure is applied in a manner allowing an inner face of the tubular body to become at least partly attached or bonded to at least a part of the internal form, preferably the reduced pressure differential between the pressure in the lumen and the pressure surrounding the tubular body, more preferably the pressure within (or provided to) the lumen is less than the pressure surrounding the tubular body (or the pressure surrounding the tubular body is greater than the pressure within (or provided to) the lumen).

Preferably the tubular body is a single walled body.

Preferably reduced pressure is applied at or adjacent formation of the lumen.

Preferably reduced pressure is applied at or adjacent a die head.

Preferably the lumen experiences the reduced pressure upon exit from an extrusion die head.

Preferably the tubular body and the internal form are co-extruded.

Preferably the tubular body so formed is corrugated.

Preferably the crests of the corrugated tubular body so formed are defined by the outer-most perimeter of the internal form.

Preferably the troughs of the corrugated tubular body so formed are defined by inwardly drawn portions of the tubular body, inwardly drawn between the internal form(s).

Preferably the internal form is a skeleton or internal supporting structure, supportive of the tubular body.

Preferably the internal form is a continuous length, one or a series of semi-continuous lengths or a series of discrete lengths.

Preferably the internal form is a mesh.

Preferably the internal form one or a combination of a helical spring or a helically wound element, a helically wound skeleton or a helically wound rib, annular disks, rings, or a plurality of discrete supports interconnected or inter-connectable by one or more connecting links.

Preferably the internal form is supportive or supporting of the lumen within the tube so formed.

Preferably the internal form is a helical element or member.

Preferably the internal form has a pitch that varies along a length (or sections) of the tube.

Preferably the internal form is a helically wound element (or member) having a pitch between adjacent turns of about 0.4 mm to about 2 mm, or about 0.5 to about 1.9, or about 0.6 to about 1.8, or about 0.7 to about 1.7, or about 0.8 to about 1.6, or about 0.9 to about 1.5, or about 1 to about 1.4, or about 1.1 mm to about 1.3 mm. More preferably, the pitch between adjacent turns is about 1 mm to about 1.5 mm.

Preferably the internal form has an outer most diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm.

Preferably the internal form is a helically wound element, the element having a diameter of about 0.05 mm to 0.3 mm, or about 0.06 to about 0.29, or about 0.07 to about 0.28, or about 0.08 to about 0.27, or about 0.09 to about 0.26, or about 0.1 to about 0.25, or about 0.11 to about 0.24, or about 0.12 to about 0.23, or about 0.13 to about 0.24, or about 0.14 to about 0.23, or about 0.15 to about 0.22, or about 0.16 to about 0.24, or about 0.17 to about 0.23, or about 0.18 to about 0.22, or about 0.19 mm to about 0.21 mm. Preferably having a diameter of about 0.1 mm to about 1.5 mm.

Preferably the internal form is of a medical grade material, preferably a medical grade stainless steel.

Preferably the tubular body has a wall thickness of about 0.05 mm to about 0.25 mm, or about 0.06 to about 0.24, or about 0.07 to about 0.23, or about 0.08 to about 0.22, or about 0.09 to about 0.21, or about 0.1 to about 0.2, or about 0.11 to about 0.19, or about 0.12 to about 0.18, or about 0.13 to about 0.17, or about 0.14 mm to about 0.16 mm. Preferably a wall thickness of about 0.1 mm to about 0.2 mm.

Preferably the tubular body has an internal diameter (e.g. the lumen) of about 1.5 mm to about 4.5 mm, or about 1.6 to about 4.4, or about 1.7 to about 4.3, or about 1.8 to about 4.2, or about 1.9 to about 4.1, or about 2 to about 4, or about 2.1 to about 3.9, or about 2.2 to about 3.8, or about 2.3 to about 3.7, or about 2.4 to about 3.6, or about 2.5 to about 3.5, or about 2.6 to about 3.4, or about 2.7 to about 3.3, or about 2.8 to about 3.2, or about 2.9 mm to about 3.1 mm.

Preferably the tubular body has an external (or outer) diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm. Preferably having an external (or outer) diameter of about 3 mm to about 5 mm.

Preferably the tubular body is corrugated, the corrugations having a depth of about 0.1 mm to about 0.5 mm.

Preferably the ratio of pitch of the internal form to outer diameter of internal form (e.g. outer-most diameter) is about 0.10 to about 0.50, more preferably the ratio is about 0.20 to about 0.35, even more the ratio is about 0.28 or about 0.29.

Preferably the ratio of the internal form diameter (e.g. diameter of actual internal form element or member) to outer diameter of internal form (e.g. outer-most diameter) is about 0.02 to about 0.10, more preferably about 0.05 to about 0.07, most preferably the ratio is 0.06.

Preferably the ratio of the corrugations depth to the external (i.e. outer) tube diameter is about 0.05 to about 0.09.

Preferably, characteristics of the tubular body contribute to desired flexibility and/or structural support required by the tube.

Preferably the tubular body is (preferably extruded from) a polymer, such as thermoplastic polymers, preferably polymers suitable for medical breathing tubes.

Preferably the tubular body is (preferably extruded from) one or a combination of any one or more of thermoplastic elastomer(s), polypropylene based elastomer(s), liquid silicon rubber(s), or breathable thermoplastic polyurethane(s), or breathable polyamides, more preferably polymers may be those such as, but not limited to, polyolefins, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Preferably the tubular body is a breathable tube, or formed of or from, a breathable material, such as breathable thermoplastic polyurethane(s) or breathable polyamides.

Preferably the reduced pressure is applied while the tubular body is in a molten, or a semi-molten or an as yet uncured state, preferably the reduced pressure is about 0 to about −2 bar (absolute), more preferably is about 0 to about −1 bar (absolute), even more preferably down to about −0.9 bar (absolute), yet even more preferably, such reduced pressure is a pressure differential between the inside of the lumen and the region surrounding the tubular body.

Preferably the internal form is electrically conductive, preferably the internal form is an electrically powered heater.

Preferably the internal form comprises electrically conductive members or electrically powered heaters or sensors (such as flow or temperature or humidity or pressure sensors).

Preferably the tube further comprises a heater, more preferably an electrically powered heater (such as a heater wire or heater circuit).

Preferably the tubular body so formed is flexible as defined by passing the test for increase in flow resistance with bending according to ISO 5367:2000(E) (Fourth edition, 2000, Jun. 1).

Preferably the medical tubing is a breathing tube.

Preferably the internal form comprises of one or more separate components.

Preferably the internal form comprises one or more components.

Preferably the tube comprises one or more internal forms.

In a second aspect, the invention may be said to broadly consist of a medical tube comprising:

a tubular body, the body defining a lumen extending between open terminal ends of the body, and an internal form enclosed within the lumen and supportive of the tubular body, an outer-most perimeter of the internal form defining a plurality of alternating crests and troughs along a length of the tubular body.

Preferably the tubular body is an extruded tube.

Preferably the tubular body is a continuous tube.

Preferably the tubular body is a continuously extruded tube.

Preferably the crests of the corrugated tubular body are defined by the outer-most perimeter of the internal form.

Preferably the troughs of the corrugated tubular body are defined by inwardly drawn portions of the tubular body, inwardly drawn between the internal form.

Preferably the internal form is a continuous length, one or a series of semi-continuous lengths or a series of discrete lengths.

Preferably the internal form is one or a combination of a helical spring or a helically wound element, a helically wound skeleton or a helically wound rib, annular disks, rings, or a plurality of discrete supports interconnected or inter-connectable by one or more connecting links.

Preferably the internal form is supporting of the tubular body defining the lumen within.

Preferably the internal form is a skeleton or internal supporting structure, supportive of the tubular body.

Preferably the tubular body is substantially unsupported in the troughs from the internal form and supported in the crests by the internal form.

Preferably the wall of the tubular body is suspended between adjacent crests.

Preferably the tubular body is (preferably extruded from) a polymer, such as thermoplastic polymers, preferably polymers suitable for medical breathing tubes.

Preferably the tubular body is a breathable tube, or is formed of or from a breathable material, such as breathable thermoplastic polyurethane(s) or breathable polyamides.

Preferably the internal form is a helically wound rib, or ribbing element.

Preferably the internal form is a helical element or member.

Preferably the internal form has a pitch that varies along a length (or sections) of the tube. Preferably the internal form is a helically wound element having a pitch between adjacent turns of about 0.4 mm to about 2 mm, or about 0.5 to about 1.9, or about 0.6 to about 1.8, or about 0.7 to about 1.7, or about 0.8 to about 1.6, or about 0.9 to about 1.5, or about 1 to about 1.4, or about 1.1 mm to about 1.3 mm. More preferably, the pitch between adjacent turns is about 1 mm to about 1.5 mm.

Preferably the internal form has an outer most diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm.

Preferably the internal form is a helically wound element, the element having a diameter of about 0.05 mm to 0.3 mm, or about 0.06 to about 0.29, or about 0.07 to about 0.28, or about 0.08 to about 0.27, or about 0.09 to about 0.26, or about 0.1 to about 0.25, or about 0.11 to about 0.24, or about 0.12 to about 0.23, or about 0.13 to about 0.24, or about 0.14 to about 0.23, or about 0.15 to about 0.22, or about 0.16 to about 0.24, or about 0.17 to about 0.23, or about 0.18 to about 0.22, or about 0.19 mm to about 0.21 mm. Preferably having a diameter of about 0.1 mm to about 1.5 mm.

Preferably the internal form is of a medical grade material, preferably a medical grade stainless steel.

Preferably the tubular body has a wall thickness of about 0.05 mm to about 0.25 mm, or about 0.06 to about 0.24, or about 0.07 to about 0.23, or about 0.08 to about 0.22, or about 0.09 to about 0.21, or about 0.1 to about 0.2, or about 0.11 to about 0.19, or about 0.12 to about 0.18, or about 0.13 to about 0.17, or about 0.14 mm to about 0.16 mm. Preferably a wall thickness of about 0.1 mm to about 0.2 mm.

Preferably the tubular body has an internal diameter of about 1.5 mm to about 4.5 mm, or about 1.6 to about 4.4, or about 1.7 to about 4.3, or about 1.8 to about 4.2, or about 1.9 to about 4.1, or about 2 to about 4, or about 2.1 to about 3.9, or about 2.2 to about 3.8, or about 2.3 to about 3.7, or about 2.4 to about 3.6, or about 2.5 to about 3.5, or about 2.6 to about 3.4, or about 2.7 to about 3.3, or about 2.8 to about 3.2, or about 2.9 mm to about 3.1 mm.

Preferably the tubular body has an external (or outer) diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm. Preferably having an external (or outer) diameter of about 3 mm to about 5 mm.

Preferably the tubular body is corrugated, the corrugations having a depth of about 0.1 mm to about 0.5 mm.

Preferably the ratio of pitch of the internal form to outer diameter of internal form (e.g. outer-most diameter) is about 0.10 to about 0.50, more preferably the ratio is about 0.20 to about 0.35, even more the ratio is about 0.28 or about 0.29.

Preferably the ratio of the internal form diameter (e.g. diameter of actual internal form element or member) to outer diameter of internal form (e.g. outer-most diameter) is about 0.02 to about 0.10, more preferably about 0.05 to about 0.07, most preferably the ratio is 0.06.

Preferably the ratio of the corrugations depth to the external (i.e. outer) tube diameter is about 0.05 to about 0.09.

Preferably, characteristics of the tubular body contribute to desired flexibility and/or structural support required by the tube.

Preferably the tubular body is (preferably extruded from) one or a combination of thermoplastic elastomers, polypropylene based elastomers, liquid silicon rubbers (LSR), or breathable thermoplastic polyurethanes, or breathable polyamides, more preferably polymers may be those such as, but not limited to, polyolefins, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Preferably the internal form is a plurality of rings spaced longitudinally along the lumen.

Preferably the rings are toroidal or annular in shape.

Preferably the internal form is one or more discrete elements linked to one another.

Preferably the internal form comprises a plurality of reinforcing ribs spaced regularly along the lumen.

Preferably each reinforcing rib comprises one turn of a helical reinforcing wire.

Preferably one turn of the helical reinforcing wire comprises one complete revolution about the lumen of the tube.

Preferably one turn of the helical reinforcing wire comprises the wire disposed between adjacent crests of the internal form.

Preferably the tubular body is flexible as defined by passing the test for increase in flow resistance with bending according to ISO 5367:2000(E) (Fourth edition, 2000, Jun. 1).

Preferably a terminal end of the tube is integrated with a nasal prong, the nasal prong being adapted for insertion into a user's nare as a nasal interface for delivering breathing gases to a user.

Preferably the internal form is a mesh.

Preferably the internal form is a conductive wire suitable for heating or sensing a property of gases within the tube.

Preferably the internal form is electrically conductive, preferably the internal form is an electrically powered heater.

Preferably the internal form comprises electrically conductive members or electrically powered heaters or sensors (such as flow or temperature or humidity or pressure sensors).

Preferably the tube further comprises a heater, more preferably an electrically powered heater (such as a heater wire or heater circuit).

Preferably the tube is a breathing tube.

Preferably the internal form comprises of one or more separate components.

Preferably the internal form comprises one or more components.

Preferably the tube comprises one or more internal forms.

In a third aspect, the invention may be said to broadly consist of a nasal cannula arrangement comprising:

at least one nasal prong, the prong having a gas(es) outlet adapted to be inserted into a user's nare and a gas(es) inlet fluidly connected to the gas(es) outlet, and a corrugated gas(es) delivery tube, the tube comprising a tubular body defining a lumen and an internal form enclosed within the lumen, the internal form supportive of the tubular body, an outer-most perimeter of the internal form defining a plurality of alternating crests and troughs along a length of the tubular body, wherein the gas(es) inlet of the nasal prong is formed integrally with a terminal end of the tube so that the tube lumen is fluidly connected to the gas(es) outlet of the nasal prong.

Preferably the nasal prong is shaped to substantially conform anatomically to the interior of a user's nose or nare.

Preferably the nasal prong is curved, or otherwise shaped or configured, to avoid a user's septum.

Preferably the nasal cannula has a substantially planar or flat or contoured backing configured to rest on a user's face, preferably as a stabilizer of the prong in the nare of a user.

Preferably one or more ribs extend between a front face of the backing and the cannula, the ribs providing a contact surface for tape or other suitable retainer employed to fasten or attach the cannula to a user's face, preferably the tape comprises adhesive portions or is an adhesive tape or a contact adhesive tape.

Preferably two nasal prongs are formed integrally with a single corrugated delivery tube.

Preferably the cannula comprises a pair of nasal prongs, each prong formed integrally with, or may be attached (or attachable) or connected (or connectable) to a terminal end of a pair of gas(es) delivery tube.

Preferably the cannula arrangement is formed of a polymer, such as a thermoplastic polymer, preferably a polymer or polymers suitable for medical breathing tubes.

Preferably the cannula arrangement is formed of one or a combination of any one or more of thermoplastic elastomer(s), polypropylene based elastomer(s), liquid silicon rubber(s), or breathable thermoplastic polyurethane(s), or breathable polyamides, more preferably polymers may be those such as, but not limited to, polyolefins, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

In a fourth aspect, the invention may be said to broadly consist of a user interface comprising a pair of nasal cannula as defined by the third aspect.

Preferably the nasal prongs of each nasal cannula are disposed adjacent each other and the respective delivery tubes extend in opposite directions away from the nasal prongs.

Preferably further comprising a harness, the harness extending between and coupling the nasal cannula.

Preferably the tube is a breathing tube.

Preferably the tube is as defined by the first or second aspect, for example where the tube is fabricated by a method as defined by the first aspect or the tube as defined by the second aspect.

In a fifth aspect, the invention may be said to broadly consist of a method of fabricating a nasal cannula, the method comprising:

providing an internal form, extruding a tubular body about the internal form, the tubular body defining a lumen enclosing the internal form, and attaching a nasal cannula thereto.

Preferably the method further comprising:

i) applying a reduced pressure within (or to) the lumen, such that the reduced pressure draws the tubular body radially inward of the lumen and of an outer-most perimeter defined by the internal form, the outer-most perimeter of the internal form defining a plurality of alternating crests and troughs along a length of the tubular body, or ii) applying an extension (or stretch) to at least a part or a region of the tubular body enclosing the internal form, such that release of the extension (or stretch) returns (or allows) the extended (or stretched) part or region of the tubular body to draw radially inward of the lumen and of an outer-most perimeter defined by the internal form, the outer-most perimeter defining a plurality of alternating crests and troughs along a length of the tubular body, or iii) a combination of i) and ii).

Preferably the method comprises over-moulding a nasal prong over a terminal end of the tubular body.

Preferably the tubular body so formed is the tube as defined by the method of the first aspect or as defined by the tube of the second aspect.

Preferably a terminal end of the tube so formed by the tubular body is located in a mould or a form for moulding or forming of a nasal cannula, preferably the mould or form is closed and the nasal cannula is over-moulded or formed over the or a terminal end of the tube.

Preferably the nasal cannula is a polymer, such as thermoplastic polymers, preferably polymers suitable for medical breathing tubes.

Preferably the nasal cannula formed from is one or a combination of any one or more of thermoplastic elastomer(s), polypropylene based elastomer(s), liquid silicon rubber(s), or breathable thermoplastic polyurethane(s), or breathable polyamides, more preferably polymers may be those such as, but not limited to, polyolefins, thermoplastic elastomers, liquid silicon rubber(s), or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Preferably the tubular body is a breathable tube, or formed of or from a breathable material, such as breathable thermoplastic polyurethane(s) or breathable polyamides.

Preferably a nasal cannula mould is provided, the mould receivable of a terminal end of the tube so formed by fabrication of the tubular body, such that operation of the mould facilities moulding of the nasal cannula, a part of which is over-moulded of the tube terminal end.

Preferably the nasal cannula arrangement produced by the nasal cannula is fluid communication with a terminal end of the tube so formed by fabrication of the tubular body.

In a sixth aspect, the invention may be said to broadly consist of a securement system for a user interface and/or user interface tubing comprising:

a dermal patch defining a securement footprint, the dermal patch having a user side and an interface side, the user side of the dermal patch being configured to attach or adhere to a user's skin, and a securing patch, at least a part of the securing patch being configured to extend over a user interface and/or associated user interface tubing and affixes to the user side of the dermal patch to secure the user interface to the user, the securing patch and the dermal patch being configured so that the securing patch can be contained within or bounded by the securement footprint of the dermal patch when the securement system is applied to a patient with a suitable or compatible user interface.

Preferably wherein the dermal patch has the same or a greater surface area than the securing patch.

Preferably the securement patch is shaped or otherwise configured to accommodate geometric or other features of the user interface and/or associated user interface tubing.

Preferably the securement patch has at least one wing.

Preferably the securement patch has a pair of wings arranged at one end of the patch, the wings are configured to secure to the dermal patch on either side of a user interface and/or associated user interface tubing.

Preferably the securement patch has a tube end wing, the tube end wing being configured to extend, or for extending, under the user interface tubing and affix to the dermal patch.

Preferably the user side of the dermal patch has a dermatologically sensitive adhesive (such as a hydrocolloid for example) that attaches or adheres the dermal patch to a user's skin.

Preferably the dermal patch has a surface of sufficient area such that, the surface distributes pressure the attachment or adhering forces across the user's skin.

Preferably the dermal patch is configured to attach or adhere to a user's face.

Preferably the dermal patch is configure to attach or adhere to a user's face adjacent the user's upper lip and/or cheek.

Preferably the securement system is configured to receive and/or secure a nasal cannula and/or associated tubing, the tubing extending from one or both sides of a user's face.

Preferably the securement system is configured for use with an infant or neonatal infant.

Preferably the securement system is configured for use with a nasal cannula as defined by the third aspect.

Preferably the securement system is configured for use with a tube as defined by either the first and/or second aspect.

In a seventh aspect, the invention may be said to broadly consist of a securement system for a user interface and/or user interface tubing comprising a two-part releasable attachment or connection arrangement, the arrangement comprising a dermal patch and a user interface patch:

the dermal patch having a patient side and an interface side, the patient side of the dermal patch being attachable to the skin of a user, (such as for example by an adhesive, generally being of a dermatologically sensitive adhesive such as a hydrocolloid), the interface side of the dermal patch being provided with the first part of a two-part releasable attachment or connection system, and the user interface patch having a interface side and patient side, the patient side of the user interface patch being provided with the complimentary second part of the two-part releasable attachment or connection system, the interface side of the user interface patch being attachable or connected to the user interface and/or associated user interface tubing, for example by adhesive or may be formed as a part of the user interface or may be provided as a back surface of the user interface upon which is provided the second part of the two-part system.

Preferably the interface side of the dermal patch has one of a hook or a loop, and the second part of the second patch has the other of the hook or loop, such that the first and second parts (and patches) are releasably attachable or connectable to each other.

Preferably the first patch is locatable and/or attachable to the skin of a user's face.

Preferably the user interface patch is locatable, or attached or attachable, or is connected to, or with, a user interface.

Preferably the user interface patch is formed integrally with, or forms a part of, a user interface.

Preferably the first part of the two-part releasable attachment or connection system on the dermal patch occupies less than about 90%, or about 85%, or about 75%, or about 60% or about 50% or about 40% or about 30% or about 20% or about 10% of the interface side of the dermal patch.

Preferably the first part of the two-part releasable attachment or connection system is adhered or adherable to the user interface side of the dermal patch with a suitable adhesive.

Preferably the user side of the dermal patch has a dermatologically sensitive adhesive (such as a hydrocolloid for example) that attaches or adheres the dermal patch to a user's skin.

Preferably the dermal patch has a surface of sufficient area such that, the surface distributes pressure the attachment or adhering forces across the user's skin.

Preferably the dermal patch is configured to attach or adhere to a user's face.

Preferably the dermal patch is configured to attach or adhere to a user's face adjacent the user's upper lip and/or cheek.

Preferably the securement system is configured to receive and/or secure a nasal cannula and associated tubing, the tubing extending from one or both sides of a user's face.

Preferably the securement system is configured for use with an infant or neonatal infant.

Preferably the securement system is configured for use with a nasal cannula as defined by anyone or more of claims third.

Preferably the securement system is configured for use with a tube as defined by the first and/or the second aspect.

Preferably the securement patch defined above is applied or appliable over the user interface and affixed or affixable to the dermal patch to provide additional securement.

Preferably the first part of the two-part releasable attachment or connection system includes a substrate secured to, or for securing to, the dermal patch.

Preferably the substrate portion includes at least one slit or at least one slot with areas of the substrate portion separated by the slit or slot.

Preferably the substrate portion includes a plurality of slits or slots or both which together divide the substrate portion into a serpentine body.

Preferably the slits and/or slots are arranged in the substrate such that a first set of at least one set of slits or slots extends into the substrate from one edge of the substrate and a second set of slits or slots extends into the substrate from the other edge of the substrate, the slits or slots of a set being interleaved with the slits or slots of the other set such that a path along the substrate portion from one end to another end without crossing the slits or slots must follow a zigzag or serpentine path much longer than a direct line between the ends.

Preferably a slit or slot of the plurality of slits or slots is curved.

Preferably a plurality of the slits or slots is curved and the curved slits or slots are arranged substantially parallel.

Preferably the slits or slots are arranged in a herring bone pattern extending in from the edges of the substrate portion.

Preferably the substrate is divided into separated portions by a serpentine slit or slot.

Preferably the substrate portion is divided into portions by a spiral slit or slot.

Preferably the substrate portion is divided into sub-portions by slits or slots arranged on substantially concentric circles.

Preferably the concentric circles are centered at approximately the centre of the substrate portion.

Preferably the slit or slots divide the substrate portion into a plurality of islands, each joined to an adjacent island or islands by a narrow bridge.

Preferably the substrate portion is divided into portions by an S shaped slit.

Preferably the substrate portion is divided into portions by a T shaped slit.

Preferably the substrate portion covers at least 70% of the area of the dermal patch.

Preferably for a boundary defining the shortest path around the perimeter of the substrate, the substrate portion covers at least 80% of the area within the boundary.

In an eighth aspect, the invention may be said to broadly consist of a method of fabricating medical tubing, the method comprising:

providing an internal form encapsulated in a coating, and providing a tubular body about the internal form, the tubular body defining a lumen enclosing the internal form, the tubular body being provided about the internal form such that the coating and an internal surface of the tubular body bond together, wherein the internal form remains encapsulated.

Preferably the step of providing an internal form comprises:

providing an elongate form encapsulated within a coating suitable for application in medical tubing, and fabricating a supportive internal form for a medical tube from the coated elongate form.

Preferably the uncoated elongate form is dipped in a bath of coating material to apply the encapsulating coating.

Preferably the bath contains a molten polymer grade at a temperature above about 150° C.

Preferably the internal form is fabricated by spirally winding the elongate form into a helical form.

Preferably the method further comprising:

providing an uncoated elongate form, encapsulating the elongate form in a coating suitable for application in medical tubing.

Preferably the method further comprising:

i) applying a reduced pressure within (or to) the lumen, such that the reduced pressure draws the tubular body radially inward, or ii) applying an extension (or stretch) to at least a part or a region of the tubular body enclosing the internal form, such that release of the extension (or stretch) returns (or allows) the extended (or stretched) part or region of the tubular body to draw radially inward, or iii) or a combination of i) and ii).

Preferably the tubular body is drawn radially inward of the lumen and of an outer-most perimeter defined by the internal form, the outer-most perimeter defining a plurality of alternating crests and troughs along a length of the tubular body to form a corrugated tube.

Preferably the tubular body is provided by extrusion or by extruding a material from a die head.

Preferably the tubular body is extruded about the internal form and a reduced pressure is applied in a manner allowing an inner face of the tubular body to become at least partly attached or bonded to at least a part of the coating, preferably the reduced pressure creates a differential between the pressure in the lumen and the pressure surrounding the tubular body, more preferably the pressure within (or provided to) the lumen is less than the pressure surrounding the tubular body (or the pressure surrounding the tubular body is greater than the pressure within (or provided to) the lumen).

Preferably the tubular body is provided about the internal form at a temperature that causes the at least a portion of the coating and the tubular body to bond.

Preferably the tubular body is provided about the internal form at a temperature allowing welding of the coating and the internal form.

Preferably the tubular body at least partially fuses with the coating.

Preferably the tubular body is a single walled body.

Preferably a reduced pressure is applied at or adjacent formation of the lumen.

Preferably the reduced pressure is applied at or adjacent a die head.

Preferably the lumen experiences the reduced pressure upon exit from an extrusion die head.

Preferably the tubular body is extruded simultaneously with fabrication of the internal form from the elongate form.

Preferably the tubular body so formed is corrugated (may be axial or helical corrugations).

Preferably the crests of the corrugated tubular body so formed are defined by the outer-most perimeter of the internal form.

Preferably the troughs of the corrugated tubular body so formed are defined by inwardly drawn portions of the tubular body, inwardly drawn between the internal form(s).

Preferably the internal form is a skeleton or internal supporting structure, supportive of the tubular body.

Preferably the internal form is a continuous length, one or a series of semi-continuous lengths or a series of discrete lengths.

Preferably the internal form one or a combination of a helical spring or a helically wound element, a helically wound skeleton or a helically wound rib, annular disks, rings, or a plurality of discrete supports interconnected or inter-connectable by one or more connecting links.

Preferably the internal form is supportive or supporting of the lumen within the tube so formed.

Preferably the internal form is a helical element or member.

Preferably the internal form has a pitch that varies along a length (or sections) of the tube.

Preferably the internal form comprises a helically wound element (or member) having a pitch between adjacent turns of about 0.4 mm to about 2 mm, or about 0.5 to about 1.9, or about 0.6 to about 1.8, or about 0.7 to about 1.7, or about 0.8 to about 1.6, or about 0.9 to about 1.5, or about 1 to about 1.4, or about 1.1 mm to about 1.3 mm. More preferably, the pitch between adjacent turns is about 1 mm to about 1.5 mm.

Preferably the internal form has an outer most diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm.

Preferably the internal form is a helically wound element, the element having a diameter of about 0.05 mm to 0.3 mm, or about 0.06 to about 0.29, or about 0.07 to about 0.28, or about 0.08 to about 0.27, or about 0.09 to about 0.26, or about 0.1 to about 0.25, or about 0.11 to about 0.24, or about 0.12 to about 0.23, or about 0.13 to about 0.24, or about 0.14 to about 0.23, or about 0.15 to about 0.22, or about 0.16 to about 0.24, or about 0.17 to about 0.23, or about 0.18 to about 0.22, or about 0.19 mm to about 0.21 mm.

Preferably the internal form is of a medical grade material, preferably a medical grade stainless steel coated with a suitable material, preferably a polymer grade or a stainless steel.

Preferably the tubular body has a wall thickness of about 0.05 mm to about 0.25 mm, or about 0.06 to about 0.24, or about 0.07 to about 0.23, or about 0.08 to about 0.22, or about 0.09 to about 0.21, or about 0.1 to about 0.2, or about 0.11 to about 0.19, or about 0.12 to about 0.18, or about 0.13 to about 0.17, or about 0.14 mm to about 0.16 mm. Preferably a wall thickness of about 0.1 mm to about 0.2 mm.

Preferably the tubular body has an internal (e.g. lumen) diameter of about 1.5 mm to about 4.5 mm, or about 1.6 to about 4.4, or about 1.7 to about 4.3, or about 1.8 to about 4.2, or about 1.9 to about 4.1, or about 2 to about 4, or about 2.1 to about 3.9, or about 2.2 to about 3.8, or about 2.3 to about 3.7, or about 2.4 to about 3.6, or about 2.5 to about 3.5, or about 2.6 to about 3.4, or about 2.7 to about 3.3, or about 2.8 to about 3.2, or about 2.9 mm to about 3.1 mm.

Preferably the tubular body has an external (or outer) diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm. Preferably having an external (or outer) diameter of about 3 mm to about 5 mm.

Preferably the tubular body is corrugated, the corrugations having a depth of about 0.1 mm to about 0.5 mm.

Preferably the ratio of pitch of the internal form to outer diameter of internal form (e.g. outer-most diameter) is about 0.10 to about 0.50, more preferably the ratio is about 0.20 to about 0.35, even more the ratio is about 0.28 or about 0.29.

Preferably the ratio of the internal form diameter (e.g. diameter of actual internal form element or member) to outer diameter of internal form (e.g. outer-most diameter) is about 0.02 to about 0.10, more preferably about 0.05 to about 0.07, most preferably the ratio is 0.06.

Preferably the ratio of the corrugations depth to the external (i.e. outer) tube diameter is about 0.05 to about 0.09.

Preferably, characteristics of the tubular body contribute to desired flexibility and/or structural support required by the tube.

Preferably the tubular body is (preferably extruded from) a polymer, such as thermoplastic polymers, preferably polymers suitable for medical breathing tubes.

Preferably the tubular body is (preferably extruded from) one or a combination of any one or more of thermoplastic elastomer(s), polypropylene based elastomer(s), liquid silicon rubber(s), or breathable thermoplastic polyurethane(s), more preferably polymers may be those such as, but not limited to, polyolefin's, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Preferably the reduced pressure is applied while the tubular body is in a molten, or a semi-molten or an as yet uncured state, preferably the reduced pressure is about 0 to about −2 bar (absolute), more preferably is about 0 to about −1 bar (absolute), even more preferably down to about −0.9 bar (absolute), yet even more preferably, such reduced pressure is a pressure differential between the inside of the lumen and the region surrounding the tubular body.

Preferably the internal form is electrically conductive, preferably the internal form is an electrically powered heater.

Preferably the internal form comprises electrically conductive members or electrically powered heaters or sensors (such as flow or temperature or humidity or pressure sensors).

Preferably the tube further comprises a heater, more preferably an electrically powered heater (such as a heater wire or heater circuit).

Preferably the tubular body so formed is flexible as defined by passing the test for increase in flow resistance with bending according to ISO 5367:2000(E) (Fourth edition, 2000, Jun. 1).

Preferably the medical tubing is a breathing tube.

Preferably the internal form comprises of one or more separate components.

Preferably the internal form comprises one or more components.

Preferably the tube comprises one or more internal forms.

In a ninth aspect, the invention may be said to broadly consist of a method of fabricating medical tubing, the method comprising:

i) providing an internal form,
ii) providing a tubular body about the internal form, the tubular body defining a lumen enclosing the internal form, and applying a reduced pressure within (or to) the lumen, or applying an extension (or stretch) to at least a part or a region of the tubular body enclosing the internal form, or
iii) or a combination of i) and ii).

Preferably applying a greater reduced pressure or a greater extension (or stretch) or a combination of both draws the tubular body radially inward of the lumen along a length of the tubular body and of an outer-most perimeter defined by the internal form when the greater reduced pressure is applied or the extension (or stretch) is released or both, the outer-most perimeter of the internal form then defining a plurality of alternating crests and troughs Preferably the internal form is encapsulated in a coating, the tubular body being provided about the internal form such that the coating and an internal surface of the tubular body bond together, wherein the internal form remains encapsulated.

In a tenth aspect, the invention may be said to broadly consist of a medical tube comprising:

a tubular body, the body defining a lumen extending between open terminal ends of the body, an internal form enclosed within the lumen and supportive of the tubular body, and a coating encapsulating the internal form, the coating securing the internal form to the tubular body.

Preferably the coating and the tubular body are welded along the tube.

Preferably the coating and the tubular body are welded at discrete locations along the tube.

Preferably the coating and the tubular body are welded substantially continuously along the length of the tube.

Preferably wherein an outer-most perimeter of the internal form defines a plurality of alternating crests and troughs along a length of the tubular body.

Preferably the crests of the corrugated tubular body are defined by the outer-most perimeter of the internal form.

Preferably the troughs of the corrugated tubular body are defined by inwardly drawn portions of the tubular body, inwardly drawn between the internal form.

Preferably the internal form is a continuous length, one or a series of semi-continuous lengths or a series of discrete lengths.

Preferably the internal form is one or a combination of a helical spring or a helically wound element, a helically wound skeleton or a helically wound rib, annular disks, rings, or a plurality of discrete supports interconnected or inter-connectable by one or more connecting links.

Preferably wherein the internal form is supporting of the tubular body defining the lumen within.

Preferably the internal form is a helical element or member.

Preferably the internal form has a pitch that varies along a length (or sections) of the tube.

Preferably the internal form is a skeleton or internal supporting structure, supportive of the tubular body.

Preferably the tubular body is substantially unsupported in the troughs from the internal form and supported in the crests by the internal form.

Preferably the wall of the tubular body is suspended between adjacent crests.

Preferably the tubular body is (preferably extruded from) a polymer, such as thermoplastic polymers, preferably polymers suitable for medical breathing tubes.

Preferably the internal form is a helically wound rib, or ribbing element.

Preferably the internal form is a helically wound strip, the coating encapsulating the strip.

Preferably the internal form is a helically wound metallic wire, the coating encapsulating the wire.

Preferably wherein the coating provides a surface that readily bonds with the tubular body.

Preferably the internal form is a helically wound element (or member) having a pitch between adjacent turns of about 0.4 mm to about 2 mm, or about 05 to about 1.9, or about 0.6 to about 1.8, or about 0.7 to about 1.7, or about 0.8 to about 1.6, or about 0.9 to about 1.5, or about 1 to about 1.4, or about 1.1 mm to about 1.3 mm. More preferably, the pitch between adjacent turns is about 1 mm to about 1.5 mm.

Preferably the internal form has an outer most diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm.

Preferably the internal form is a helically wound element, the element having a diameter of about 0.05 mm to 0.3 mm, or about 0.06 to about 0.29, or about 0.07 to about 0.28, or about 0.08 to about 0.27, or about 0.09 to about 0.26, or about 0.1 to about 0.25, or about 0.11 to about 0.24, or about 0.12 to about 0.23, or about 0.13 to about 0.24, or about 0.14 to about 0.23, or about 0.15 to about 0.22, or about 0.16 to about 0.24, or about 0.17 to about 0.23, or about 0.18 to about 0.22, or about 0.19 mm to about 0.21 mm. Preferably having a diameter of about 0.1 mm to about 1.5 mm.

Preferably the internal form is of a medical grade material, preferably a medical grade stainless steel.

Preferably the tubular body has a (wall) thickness of about 0.05 mm to about 0.25 mm, or about 0.06 to about 0.24, or about 0.07 to about 0.23, or about 0.08 to about 0.22, or about 0.09 to about 0.21, or about 0.1 to about 0.2, or about 0.11 to about 0.19, or about 0.12 to about 0.18, or about 0.13 to about 0.17, or about 0.14 mm to about 0.16 mm. Preferably a wall thickness of about 0.1 mm to about 0.2 mm.

Preferably the tubular body has an internal diameter (e.g. the lumen) of about 1.5 mm to about 4.5 mm, or about 1.6 to about 4.4, or about 1.7 to about 4.3, or about 1.8 to about 4.2, or about 1.9 to about 4.1, or about 2 to about 4, or about 2.1 to about 3.9, or about 2.2 to about 3.8, or about 2.3 to about 3.7, or about 2.4 to about 3.6, or about 2.5 to about 3.5, or about 2.6 to about 3.4, or about 2.7 to about 3.3, or about 2.8 to about 3.2, or about 2.9 mm to about 3.1 mm. Preferably having an external (or outer) diameter of about 3 mm to about 5 mm.

Preferably the tubular body is corrugated, the corrugations having a depth of about 0.1 mm to about 0.5 mm.

Preferably the ratio of pitch of the internal form to outer diameter of internal form (e.g. outer-most diameter) is about 0.10 to about 0.50, more preferably the ratio is about 0.20 to about 0.35, even more the ratio is about 0.28 or about 0.29.

Preferably the ratio of the internal form diameter (e.g. diameter of actual internal form element or member) to outer diameter of internal form (e.g. outer-most diameter) is about 0.02 to about 0.10, more preferably about 0.05 to about 0.07, most preferably the ratio is 0.06.

Preferably the ratio of the corrugations depth to the external (i.e. outer) tube diameter is about 0.05 to about 0.09.

Preferably, characteristics of the tubular body contribute to desired flexibility and/or structural support required by the tube.

Preferably the tubular body has an external (or outer) diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm.

Preferably the tubular body is (preferably extruded from) one or a combination of thermoplastic elastomers, polypropylene based elastomers, liquid silicon rubber(s), or breathable thermoplastic polyurethanes, more preferably polymers may be those such as, but not limited to, polyolefin's, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Preferably the internal form is a plurality of rings spaced longitudinally along the lumen.

Preferably the rings are toroidal or annular in shape.

Preferably the internal form is one or more discrete elements linked to one another.

Preferably the internal form comprises a plurality of reinforcing ribs spaced regularly along the lumen.

Preferably each reinforcing rib comprises one turn of a helical reinforcing wire.

Preferably one turn of the helical reinforcing wire comprises one complete revolution about the lumen of the tube.

Preferably one turn of the helical reinforcing wire comprises the wire disposed between adjacent crests of the internal form.

Preferably the tubular body is flexible as defined by passing the test for increase in flow resistance with bending according to ISO 5367:2000(E) (Fourth edition, 2000, Jun. 1).

Preferably a terminal end of the tube is integrated with a nasal prong, the nasal prong being adapted for insertion into a user's nare as a nasal interface for delivering breathing gases to a user.

Preferably the internal form is a mesh.

Preferably the internal form is a conductive wire suitable for heating or sensing a property of gases within the tube.

Preferably the internal form is electrically conductive, preferably the internal form is an electrically powered heater.

Preferably the internal form comprises electrically conductive members or electrically powered heaters or sensors (such as flow or temperature or humidity or pressure sensors).

Preferably the tube further comprises a heater, more preferably an electrically powered heater (such as a heater wire or heater circuit).

Preferably the tube is a breathing tube.

Preferably the internal form comprises of one or more separate components.

Preferably the internal form comprises one or more components.

Preferably the tube comprises one or more internal forms.

In an eleventh aspect, the invention may be said to broadly consist of a medical tube comprising:

a tubular body, the body defining a lumen extending between open terminal ends of the body, and an internal form enclosed within the lumen and supportive of the tubular body.

Preferably an outer-most perimeter of the internal form defines a plurality of alternating crests and troughs along a length of the tubular body.

Preferably the internal form is encapsulated in a coating, the coating securing the internal form to the tubular body.

In a twelfth aspect, the invention may be said to broadly consist of a nasal cannula arrangement comprising:

at least one nasal prong, the prong having a gas(es) outlet adapted to be inserted into a user's nare and a gas(es) inlet fluidly connected to the gas(es) outlet, the prong being shaped to follow the anatomical curvature of a user's nare.

Preferably the nasal prong is shaped to avoid contact with the septum of a user at the base of a user's nose.

Preferably the nasal prong is shaped to avoid contact with the internal structure of a user's nose.

Preferably the nasal prong is shaped to substantially align the flow of breathing gas(es) through the gas(es) outlet with a user's upper airways.

Preferably the nasal prong is shaped to extend generally upwardly and rearwardly into a user's nares, the nasal prong having a curvature that includes at least two inflection points.

Preferably the nasal prong defines a lumen that extends between the gas(es) inlet and the gas(es) outlet, the shape of the lumen changing from generally circular at the gas(es) inlet to generally elliptical at the gas(es) outlet.

Preferably the prong is shaped to maximize the cross-sectional area of the lumen.

Preferably the interface further includes a support that extends along a user's upper lip.

Preferably the interface comprises two nasal prongs spaced symmetrically about a user's sagittal plane, the prongs extending inwardly below the user's nose from a base on a common support disposed along a user's upper lip.

Preferably the nasal prongs extend from the support toward the user's septum and curve around the corners of a user's nostrils upwardly and rearwardly into the user's nares, each prong extending along a generally inclined posterior trajectory and passing through two mediolateral points of inflection that orientate the gas(es) outlet with respect to the user's upper airway passages.

Preferably the prongs may have a shaped trajectory fitting the anatomical shape of the user's nostril. More preferably, i) in a first portion (or phase) of such a prong, the trajectory moves horizontally towards the midline of the face, ii) in a second portion (or phase) of the prong, the trajectory curves upwards directly into the nostril towards the crown of the head, iii) in a third potion (or phase) of the prong, the trajectory rolls backwards into the head following the anatomical curvature of the nostril, and iv) in a fourth portion (or phase), the trajectory tilts horizontally towards the centre of the cannula to align the flow outlet with the user's upper airway.

Preferably the prongs have a cross-section that varies along the central trajectory. For example, the cross-sections may be generally circular at the base (i.e. in the region of the first portion) of the trajectory and become generally elliptical towards the end of the trajectory or prong (e.g. in the region of the fourth portion).

Preferably the cross-sectional diameter generally decreases along the trajectory from the first portion (or phase) to the end of the fourth portion (or phase).

Preferably the nasal cannula further comprises a contoured backing or facial pad configured to rest on a user's face.

Preferably the backing or facial pad is pre-formed to be of a contour that is substantially curved to fit a user's face or upper lip region.

Preferably each prong is receivable of independent flow from a gas source.

In a thirteenth aspect, the invention may be said to broadly consist of a nasal cannula arrangement comprising:

at least one nasal prong, the prong having a gas(es) outlet adapted to be inserted into a users nare and a gas(es) inlet fluidly connected to the gas(es) outlet, and a gas(es) delivery tube, the tube comprising a tubular body defining a lumen and an internal form enclosed within the lumen, the internal form supportive of the tubular body, wherein the gas(es) inlet of the nasal prong is formed integrally with a terminal end of the tube so that the tube lumen is fluidly connected to the gas(es) outlet of the nasal prong.

Preferably an outer-most perimeter of the internal form defines a plurality of alternating crests and troughs along a length of the tubular body, Preferably the prong is shaped to follow the anatomical curvature of a user's nare.

Preferably the nasal prong is curved, or otherwise shaped or configured, to avoid a user's septum.

Preferably the nasal cannula has a contoured backing or facial pad configured to rest on a user's face, preferably as a stabilizer of the prong in the nare of a user.

Preferably one or more ribs extend between a front face of the backing or facial pas and the cannula, the ribs providing a contact surface for tape or other suitable retainer employed to fasten or attach the cannula to a user's face, preferably the tape comprises adhesive portions or is an adhesive tape or a contact adhesive tape.

Preferably wherein two nasal prongs are formed integrally with a single corrugated delivery tube.

Preferably the cannula arrangement is formed of a liquid silicon rubber or a polymer, such as a thermoplastic polymer, preferably a polymer or polymers suitable for medical breathing tubes.

Preferably the cannula arrangement is formed of one or a combination of any one or more of thermoplastic elastomer(s), polypropylene based elastomer(s), liquid silicon rubber(s), or breathable thermoplastic polyurethane(s), more preferably polymers may be those such as, but not limited to, polyolefin's, thermoplastic elastomers, breathable polyester elastomers, or breathable thermoplastic elastomers, for example thermoplastic elastomer families, such as styrene block copolymers, copolyester elastomers, or thermoplastic polyolefin elastomers or thermoplastic polyurethane elastomers, breathable polyester elastomer, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Preferably, such a cannula may be used in combination with the tube as defined by any one of the aspects above.

In a fourteenth aspect, the invention may be said to broadly consist of a user interface comprising a pair of nasal cannula as defined by the thirteenth aspect.

Preferably, in such a user interface, the nasal prongs are disposed adjacent each other and the respective delivery tubes extend in opposite directions away from the nasal prongs.

Preferably, such a user interface further comprising a harness, the harness extending between and coupling the nasal cannula.

Preferably the tube is a breathing tube.

Preferably, in such a user interface, the tube is as defined by anyone of the above aspects.

Preferably, in such a user interface, the prong is glued or otherwise adhered to the tube.

In a fifteenth aspect, the invention may be said to broadly consist of a nasal cannula arrangement comprising:

at least one nasal prong, the prong having a gas outlet adapted to be inserted into a user's nare and a gas inlet fluidly connected to the gas outlet, the at least one nasal prong comprising a backing, the backing configured to rest on a user's face, wherein a lip extends about at least a part of the perimeter of a rear surface of the backing, the rear surface configured for receiving or retaining a user interface patch, such that in use, the user interface patch may be releasably attachable or connectable to, or with, a dermal patch affixed to a user's face.

Preferably the lip is a barrier.

Preferably the lip is deformable.

Preferably the lip extends at least about the perimeter of a region substantially adjacent to a prong associated with the backing.

Preferably the lip is a series of one or more separate lips.

Preferably the one or more separate lips are adjacent, or adjoining or overlapping lip portions.

Preferably the lip is an endless lip extending about the perimeter of the rear surface of the backing.

Preferably, in use, the lip substantially forms a fluid seal, or barrier to fluid, between the rear surface of the backing and a cannula facing surface of the user interface patch.

Preferably the backing is substantially planar or flat or contoured (such as a pre-formed curve) backing configured to rest on a user's face.

Preferably the backing assists as a stabilizer of the prong(s) in the nare(s) of a user.

Preferably the at least one backing extends laterally outward from the at least one nasal prong, away from the septum of a user.

Preferably the cannula is further defined by any one of the aspects above.

Preferably the cannula is operational with the securement system as in the aspects above.

Preferably the user interface patch receivable or retainable on the rear surface of the backing (or backing component) as defined by any one of the aspects above.

Preferably the at least the lip(s) is hydrophobic.

Preferably the at least the lip(s) comprises at least one outer perimeter lip portion and at least one inner perimeter lip portion, each of said lips provided for contacting with a user's face.

Preferably the gas inlet of the cannula is fluidly connected to or with the tube as defined in any one of the aspects above.

In a sixteenth aspect, the invention may be said to broadly consist of a part of a releasable fastener that includes a substrate portion supporting a distributed mechanical fastener across its surface, the substrate portion being flexible but substantially non-stretchable, the substrate portion being divided into multiple areas by at least one slit or at least one slot, such that the substrate may substantially conform to an underlying compound curved surface by independent bending of different divided portions of the substrate.

Preferably the substrate portion includes a plurality of slits or slots or both which together divide the substrate portion into a serpentine body.

Preferably the slits and/or slots are arranged in the substrate such that a first set of at least one set of slits or slots extends into the substrate from one edge of the substrate and a second set of slits or slots extends into the substrate from the other edge of the substrate, the slits or slots of a set being interleaved with the slits or slots of the other set such that a path along the substrate portion from one end to another end without crossing the slits or slots must follow a zigzag or serpentine path much longer than a direct line between the ends.

Preferably a slit or slot of the plurality of slits or slots is curved.

Preferably a plurality of the slits or slots is curved and the curved slits or slots are arranged substantially parallel.

Preferably the slits or slots are arranged in a herring bone pattern extending in from the edges of the substrate portion.

Preferably the substrate is divided into separated portions by a serpentine slit or slot.

Preferably the substrate portion is divided into portions by a spiral slit or slot.

Preferably the substrate portion is divided into sub-portions by slits or slots arranged on substantially concentric circles.

Preferably the concentric circles are centered at approximately the centre of the substrate portion.

Preferably the slit or slots divide the substrate portion into a plurality of islands, each joined to an adjacent island or islands by a narrow bridge.

Preferably the substrate portion is divided into portions by an S shaped slit.

Preferably the substrate portion is divided into portions by a T shaped slit.

Preferably the substrate portion covers at least 70% of the area of the dermal patch.

Preferably a boundary defining the shortest path around the perimeter of the substrate, the substrate portion covers at least 80% of the area within the boundary.

In a sixteenth aspect, the invention may be said to broadly consist of a user interface assembly comprising:

a securement system for the user interface and/or a component associated with the user interface (e.g. such as a tube or tubing), and a tube connected to the user interface providing at least a part of a breathing circuit for a user of the interface, wherein the securement system comprises a two-part releasable attachment (or connection) arrangement, the arrangement comprising:

a dermal patch and a user interface patch, the dermal patch having a patient side and an interface side, the patient side of the dermal patch being attachable to the skin of a user, (e.g. by an adhesive, generally being of a dermatologically sensitive adhesive such as a hydrocolloid), the interface side of the dermal patch being provided with the first part of a two-part releasable attachment or connection system, and the user interface patch having a interface side and patient side, the patient side of the user interface patch being provided with the complimentary second part of the two-part releasable attachment or connection system, the interface side of the user interface patch being attachable (or connectable) to the user interface and/or the component associated with the user interface (e.g. a tube or tubing), and wherein the tube comprises:

a tubular body, the body defining a lumen extending between open terminal ends of the body, an internal form enclosed within the lumen and supportive of the tubular body, and a coating encapsulating the internal form, the coating securing the internal form to the tubular body.

Preferably the interface is a nasal cannula.

Preferably the interface includes one or a pair of nasal prongs.

Preferably the interface is comprises a securement system.

Preferably the tube is a medical breathing tube.

Preferably the interface is a nasal cannula arrangement comprising: at least one nasal prong, the prong having a gas outlet adapted to be inserted into a user's nare and a gas inlet fluidly connected to the gas outlet, the at least one nasal prong comprising a backing, the backing configured to rest on a user's face, wherein a lip extends about at least a part of the perimeter of a rear surface of the backing, the rear surface configured for receiving or retaining the user interface patch, such that in use, the user interface patch may be releasably attachable or connectable to, or with, the dermal patch affixed to a user's face.

Preferably the lip is a barrier.

Preferably the lip is deformable.

Preferably the lip extends at least about the perimeter of a region substantially adjacent to a prong associated with the backing.

Preferably the lip is an endless lip extending about the perimeter of the rear surface of the backing.

Preferably the lip is a series of one or more separate lips.

Preferably the one or more separate lips are adjacent or adjoining or overlapping lip portions.

Preferably, in use, the lip substantially forms a fluid (e.g. liquid) seal, or barrier to fluid, between the rear surface of the backing and a cannula facing surface of the user interface patch.

Preferably the backing is substantially planar or flat or contoured (such as a pre-formed curve) backing configured to rest on a user's face.

Preferably the backing assists as a stabilizer of the prong (s) in the nare(s) of a user.

Preferably the at least one backing extends laterally outward from the at least one nasal prong, away from the septum of a user.

It should be appreciated the various embodiments of tube as described above may be utilised in combination with a user interface or nasal cannula, such as for example those described herein.

It should be appreciated the various embodiments of securement system as described above may be utilised in combination with a user interface or nasal cannula, such as for example those described herein.

It should be appreciated the various embodiments of a user interface assembly as described herein may be utilised in combination with the tubes as also described herein.

The term comprising as used in the specification and claims means 'consisting at least in part of'. When interpreting each statement in the specification and claims that includes the term 'comprising', features other than that or those prefaced by the term may also be present. Related terms such as 'comprise' and 'comprises' are to be interpreted in the same manner.

This disclosure may also be said to broadly consist in the parts, elements and features referred to or indicated in the specification of the application and/or statements of disclosure, individually or collectively, and any or all combinations of any two or more said parts, elements, features or statements of disclosure, and where specific integers are mentioned herein which have known equivalents in the art to which this disclosure relates, such known equivalents are deemed to be incorporated herein as if individually set forth.

The disclosure consists in the foregoing and also envisages constructions of which the following gives examples only.

BRIEF DESCRIPTION OF THE DRAWINGS

These and other features, aspects and advantages of the present disclosure will now be described with reference to the drawings of preferred embodiments, which embodiments are intended to illustrate and not to limit the disclosure, and in which figures:

FIG. 6 is a perspective view of a nasal interface incorporating a pair of reinforced medical tubes each coupled to a nasal prong.

FIG. 11 is a front elevation of the nasal interface of FIG. 7 shown in cross-section.

FIG. 36A illustrates the outline of a dermal patch according to some embodiments.

FIGS. 36B to 36R illustrate various embodiments of a fastener substrate portion for securing to the dermal patch of FIG. 36A.

DETAILED DESCRIPTION OF THE PREFERRED EMBODIMENT

Medical tubing (i.e., breathing tubes) is subjected to various constraints. Some of the constraints may be performance driven, such as weight, flexibility and flow characteristics. Other constraints may be mandated by regulatory authorities, where compliance is necessary before the tube may be used in medical applications. Mandated constraints may include an assessment of the structural integrity of the tube and the biocompatibility or sterility (for hygiene purposes) of the tubing components. One such constraint is bending induced flow resistance, which may be defined according to the relevant test provided in ISO 5367:2000(E) (Fourth edition, 2000, Jun. 1).

Biocompatibility of materials can be useful, for example materials which can interact or come into contact with breathing gases or other fluids, and which do not leach or impart material to breathing gases or other fluids which may be consumed or ingested by a user or patient. Sterility may also be useful for helping ensure there is no or minimal (if any) transfer or disease to a user or patient.

Accordingly, a multitude of criteria are considered during the design and testing of medical tubes, which is reflected in the variety of tubing available in the medical field. The specialist requirements and peculiarities of different medical procedures and applications may also contribute to the variety of medical tubing available. The specific nature of different medical applications means that a tube that is particularly well suited to a specific procedure may not satisfy the criteria for a different medical application.

The application specific configuration of medical tubing can complicate and restrict the associated design process. Furthermore, the stringent regulations regarding component use often confine medical practitioners to strict compliance with component guidelines and instructions.

Tubing

Figure 1:
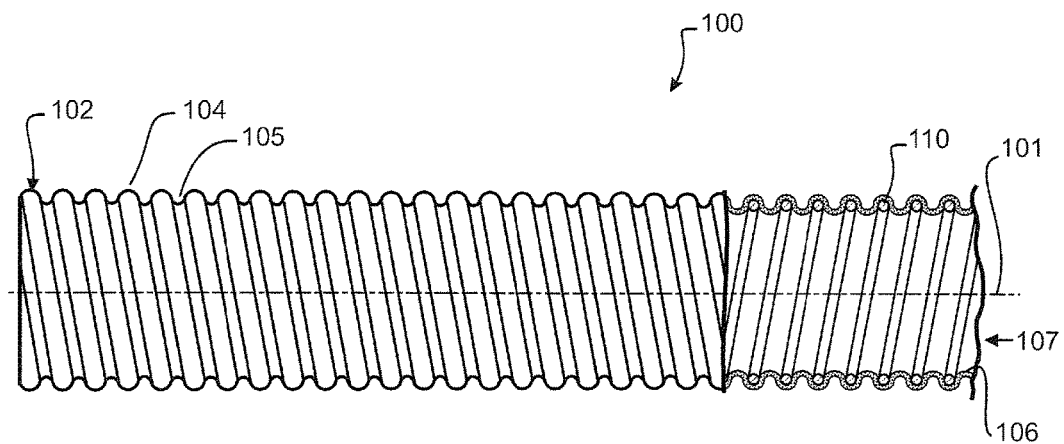
FIG. 1 is a side elevation of a corrugated medical tube with one end of the tube shown in cross section to depict an arrangement of a tubular body about an internal form.
Figure 2:
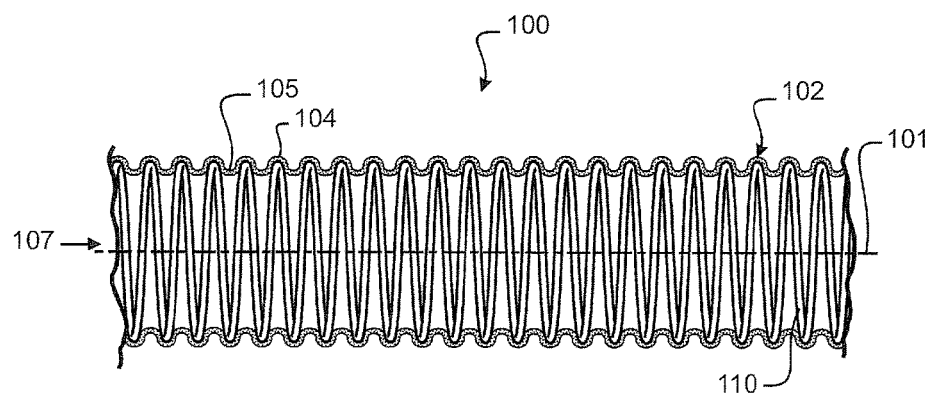
FIG. 2 is a side elevation of a medical tube shown in cross section with the tubular body cut away to reveal a continuous helical internal form.

A medical tube 100 is generally illustrated in FIG. 1. In a first embodiment, the medical tube 100 is corrugated. However, the tube may also be produced or fabricated with a smooth outer surface (e.g. FIG. 24B), or a generally smooth inner surface (e.g. FIGS. 3B, 3C). In one illustrated embodiment the tube 100 comprises a tubular body 102. The body 102 defines a lumen 107 that extends between open terminal ends of the body 102. An internal form 110 is enclosed within the lumen 107. The internal form is supportive of the tubular body. An outer-most perimeter of the internal form defines a plurality of alternating crests and troughs along a length of the tubular body.

The illustrated tube 100 has a corrugated profile that comprises a plurality of crests 104 and troughs 105. The crests 104 and troughs 105 extend around the circumference of the tube 100 and alternate along the tubular body 102 (or walls thereof) (i.e., in a direction generally parallel to a longitudinal axis 101 of the tube 100).

The tubular body 102 defines the lumen 107 that extends between terminal ends of the tube 100. For medical applications, the passage of gases through the tube 100 is confined to the lumen 107, with the tubular body 102 defining an outer boundary of the passageway. The tube 100 preferably has an opening disposed adjacent either terminal end. Ideally, the opening is arranged generally coaxial with the lumen (i.e., aligned with the longitudinal axis 101 in the illustrated embodiment) to reduce flow disturbances within the tube 100.

The illustrated tube 100 also comprises the internal form 110 that the tubular body 102 is disposed over, about or around. The tubular body 102 encloses the internal form 110 within the lumen of the tube 100. The internal form 110 provides a skeleton that defines the general shape and contributes to the structural characteristics of the tube 100. Preferably, an inner face or surface of the tubular body 102 is secured to the internal form 110. The tubular body 102 and the internal form 110 may be secured together by shrink fitting the tubular body 102 over the internal form 110 (e.g. FIG. 3D), applying the tubular body 102 over the internal form in a molten, semi-molten or an as yet uncured state, causing the inner surface of the tubular body 102 to fuse and bind (or bond) to the inner form 110 (e.g. FIG. 3C), or even providing a tubular body with at least an inner wall layer and an outer wall layer with the internal form sandwiched between them (e.g. FIG. 3B).

The internal form 110 preferably defines a skeletal substructure that is arranged about the longitudinal axis 101 of the tube 100 and that supports the tubular body 102. The tubular body 102 is disposed over the internal form 110 and the corrugations in the tubular body 102 reflect the structure of the reinforcing skeleton provided by the internal form 110. The crests 104 of the tube corrugation correspond to reinforcing ribs (i.e., the shape of the internal form 110) that support the tubular body 102. The troughs 105 in the tube corrugation preferably are unsupported sections of the tubular body 102, which are suspended between adjacent reinforcing ribs.

The internal form 110 such as those illustrated in FIGS. 1, 2, 3B-3D, 24A, 24B, comprises a continuous helical skeleton that has a similar structure to a coil spring. The skeleton produces a helical corrugation in the tubular body 102 that is visible in the left-hand portion of FIG. 1. The internal form 110 is continuously secured to the tubular body 102 at the crests 104 of the corrugation in the illustrated embodiment. The tubular body 102 conforms to the contour of the internal form 110, wrapping about each reinforcing rib. In the illustrated embodiment, the contact interface between each reinforcing rib and the tubular body 102 may exceed half of the circumferential surface of the rib.

Figure 3A:
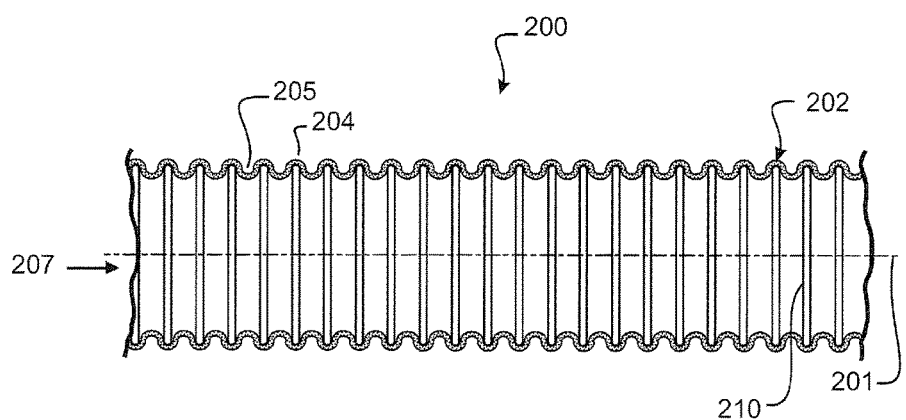
FIG. 3A is a side elevation of a medical tube shown in cross section with the tubular body cut away to reveal a plurality of independent rings that represent a discrete internal form.

FIG. 3A illustrates another embodiment of a medical tube 200. The medical tube 200 includes a body 202 that defines a lumen 207 that extends between open terminal ends of the body. In this embodiment, an internal form 210 comprises a plurality of rings spaced along a longitudinal axis 201 of the tube 200. Each ring 210 provides a circumferential reinforcing rib positioned coincident with a crest 204 in the tubular body 202. The individual rings constitute the reinforcing skeleton of the illustrated internal form 210. Accordingly, the tube 200 has a circumferential corrugation with discrete crests 204 and troughs 205 extending along the tube 200 about the longitudinal axis 201. Adjacent rings may be linked to resist narrowing of the lumen when the tube is twisted (i.e., when a torsional force is applied). The rings may be formed from washers or discs with an aperture to allow flow therethrough. Preferably the rings are toroidal or annular in shape.

Figure 24A:
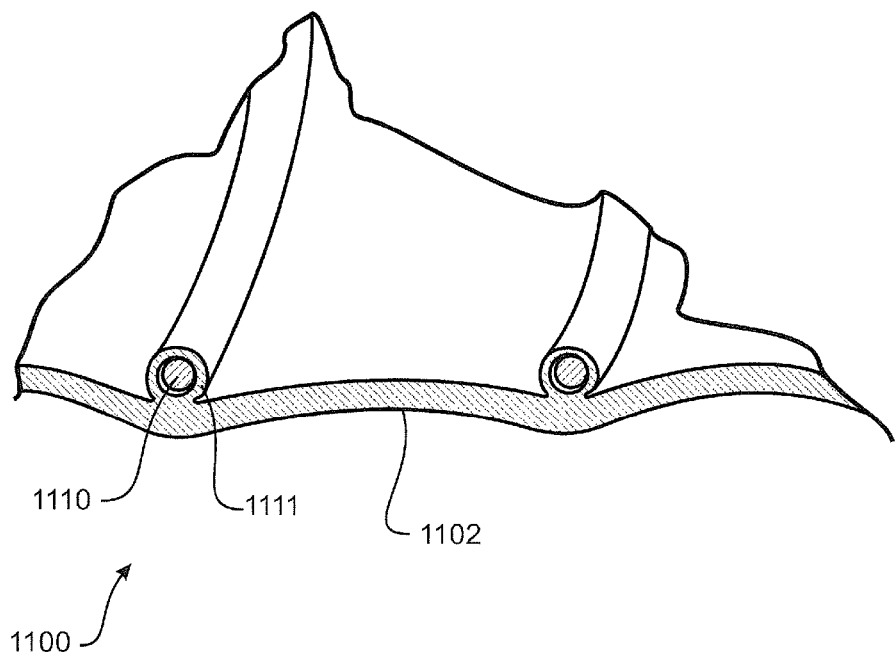
FIG. 24A is a close up perspective view of a sectioned medical tube with the corrugated tubular body cut away to reveal a coated helical internal form.
Figure 24B:
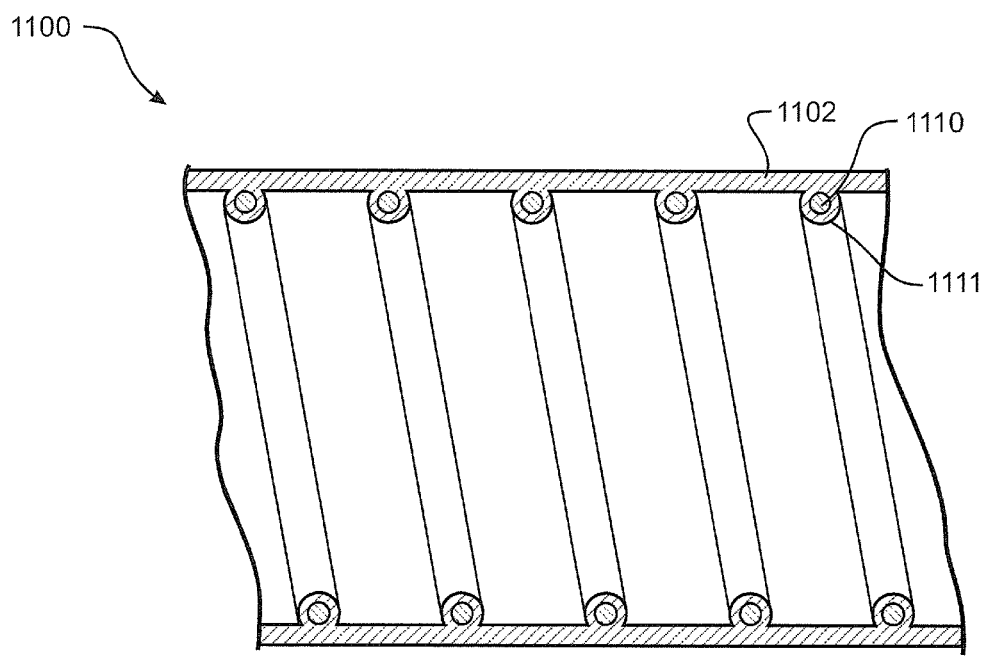
FIG. 24B is a close up perspective view of a sectioned medical tube with the smooth tubular body cut away to reveal a coated helical internal form.
Figure 25A:
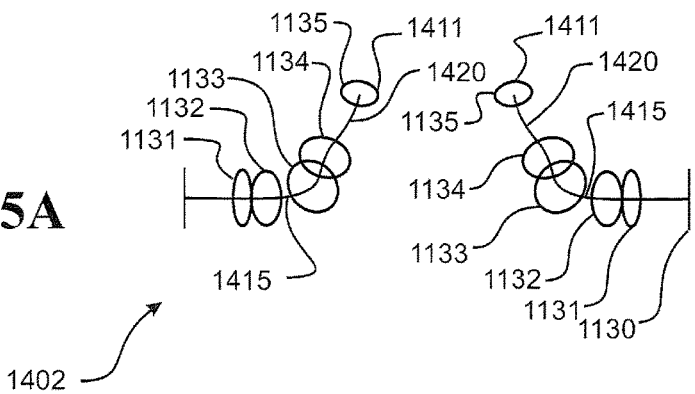
FIG. 25A is a schematic front elevation of a pair of nasal prongs illustrating the shape of the prong and the internal lumen.
Figure 25B:
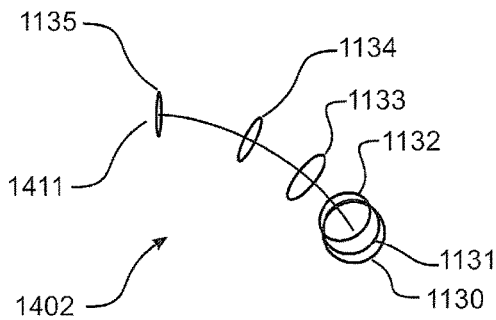
FIG. 25B is a schematic side elevation of a pair of nasal prongs illustrating the shape of the prong and the internal lumen.
Figure 25C:
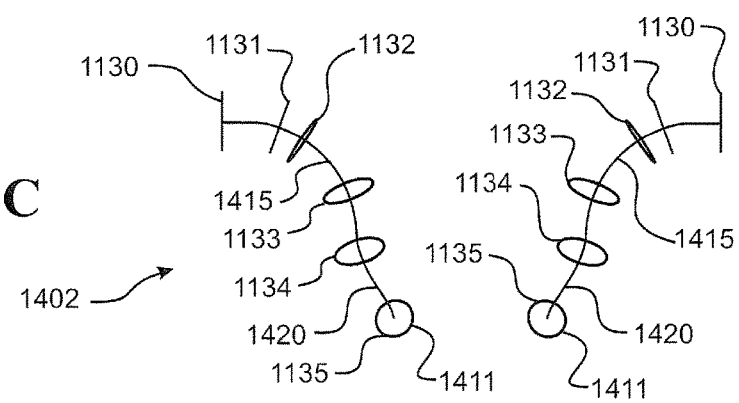
FIG. 25C is a schematic front elevation of a pair of inverted nasal prongs illustrating the shape of the prong and the internal lumen.
Figure 25D:
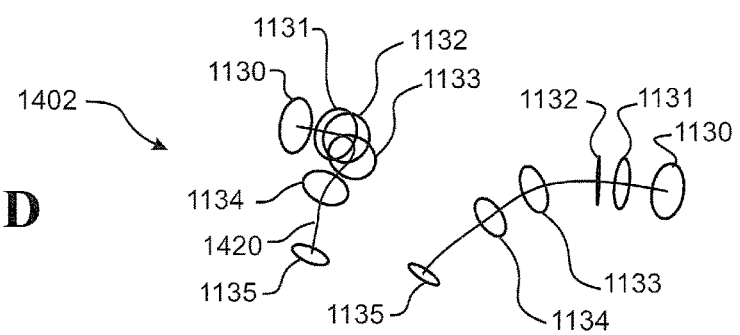
FIG. 25D is a schematic perspective view of a pair of inverted nasal prongs illustrating the shape of the prong and the internal lumen.
Figure 26A:
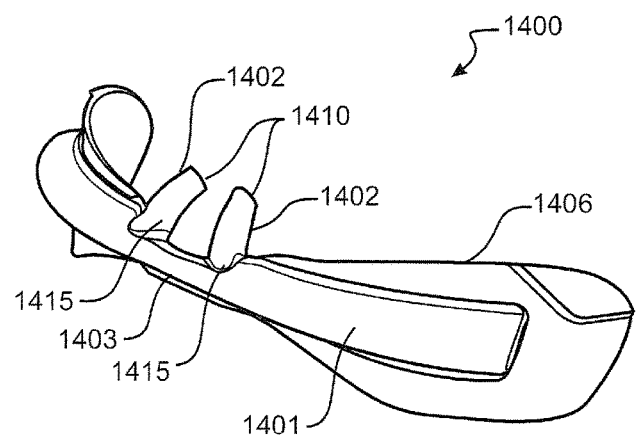
FIG. 26A is a perspective elevation of a nasal interface with curved backing components.
Figure 26B:
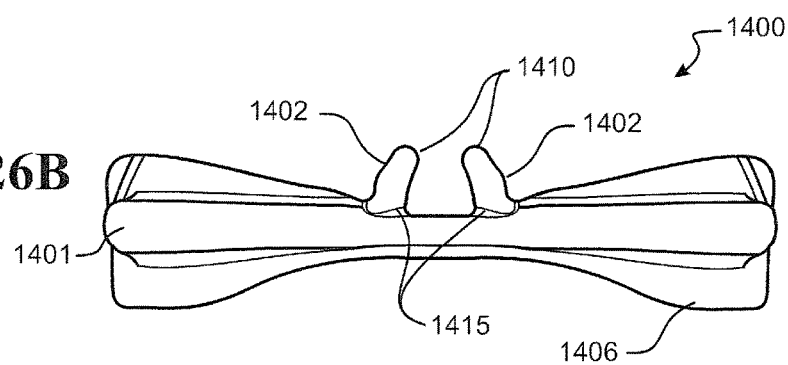
FIG. 26B is a front elevation of a nasal interface with curved backing components.
Figure 26C:
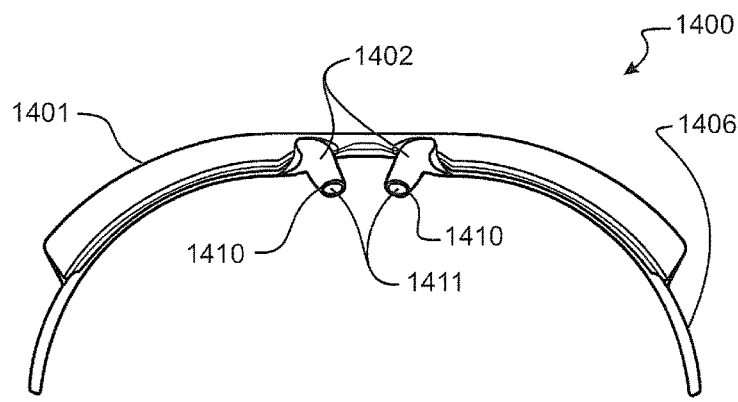
FIG. 26C is a top elevation of a nasal interface with curved backing components.
Figure 26D:
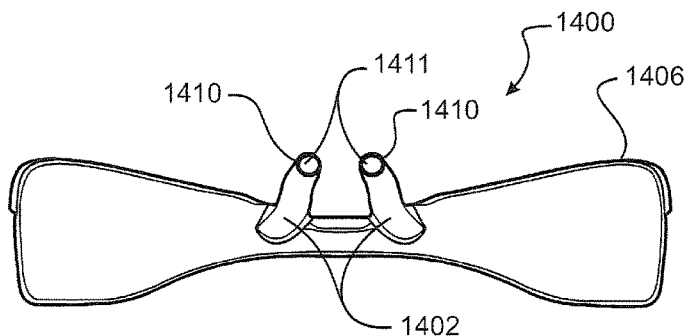
FIG. 26D is a rear elevation of a nasal interface with curved backing components.

Another embodiment of tube 1100 is illustrated in FIG. 24B. The tube 1100 has a similar construction to the corrugated tube 100 illustrated in FIG. 1, comprising a tubular body 1102 and an internal form 1110. However, the tubular body 1102 of the tube 1100 illustrated in FIG. 24B defines a smooth or non- or un-corrugated outer wall.

The internal form may have an outer coating as illustrated in the sectioned tube in FIGS. 24A and 24B. The coating illustrated in FIGS. 24A and 24B is about 35 microns thick and the tube wall is about 150 microns thick. The coating 1111 fully encapsulates the internal form 1110. In an alternate form it may also be advantageous to partially coat the internal form, such as coating discrete sections over of the length of the internal form 1110.

The internal form 1110 may be coated to increase the strength of the bond formed with the tubular body 1102, improve biocompatibility or sterility within the tube and/or isolate the internal form from the contents of the tube (such as to prevent corrosion of the internal form). Preferably the coating is sufficiently thin that it does not negatively impact on the mechanical properties of the internal form, such as reducing elasticity or flexibility.

Figure 3B:
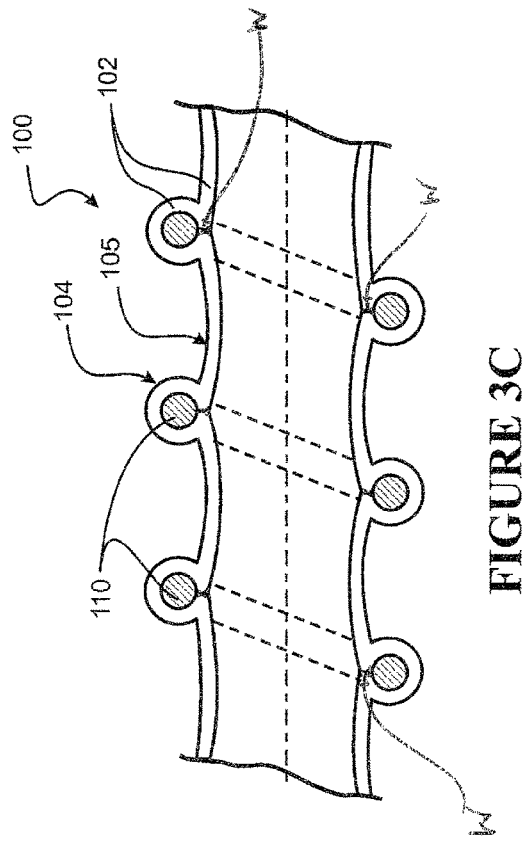
FIG. 3B is a side elevation of a medical tube shown in cross section illustrating a sandwich wall structure about an internal form.

The tube of FIG. 3B is of a generally sandwich construction the tube is made by inserting a thin walled polymer tube into the centre of an internal form, such as a coil spring. This assembly is then passed through a crosshead tubing extrusion die which extrudes a molten and similarly thin walled polymer tube over the outside of the assembly. The molten outer tube is brought in contact with the inner tube by means of draw-down of the extruded melt, and/or a pressure differential which may be a vacuum applied between the two layers, or a positive pressure applied to the inside of the inner tube or the outside of the outer tube or a combination of all these. Contact of the molten outer tube with the inner tube causes bonding between the two, and once cooled this leaves a tube consisting of an inner and an outer wall of a tubular body. The internal form (e.g. coil spring wire reinforcement) remains sandwiched between the two wall layers.

Such a tube may be formed to have a fairly smooth bore to provide low resistance to flow, while the exterior wall layer of the tube is corrugated to aid with tubular body flexibility. The internal form is locked in place mechanically by the sandwich effect. Therefore, pre-coated internal forms may not be required to achieve this adhesion to the tube wall, although that option exists. This tube may be two thin layers of tubing of similar material bonded together with the internal form (e.g. spring) locked into position away from the gas path. This provides a very flexible yet strong, crush and kink resistant tube. Mechanically locking the spring in place helps maintain the integrity of the tubing construction under axial stress, and not having the spring in the gas path reduces the biocompatibility or sterility requirements of internal form components.

Figure 3C:
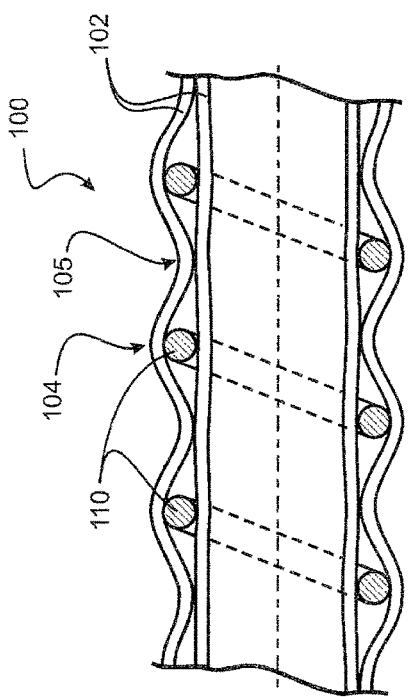
FIG. 3C is a side elevation a further embodiment where an internal form is embedded in the wall.

The tube of FIG. 3C is of a generally embedded construction. The tube of this embodiment is made by an internal form (such as a coil spring) being passed through a crosshead extrusion die which extrudes a polymer tube (tubular body) over the outside of the internal form (e.g. spring). Using a haul-off speed to achieve draw-down combined with either an internal vacuum or external positive pressure (or both) the polymer is sucked between the coils of the internal form (e.g. spring) to the point where the internal form is enclosed and locked in place mechanically. The tubular body formed is of a generally corrugated form (flexible) and does not require pre-coated internal forms to achieve adhesion, although that option exists. The tubular body is of a sufficient temperature that once the internal form is surrounded, the tubular body may come into contact with itself and self-weld to itself from the heat of extrusion. In this respect, weld lines or welded regions are shown as, W in FIG. 3C.

Figure 3D:
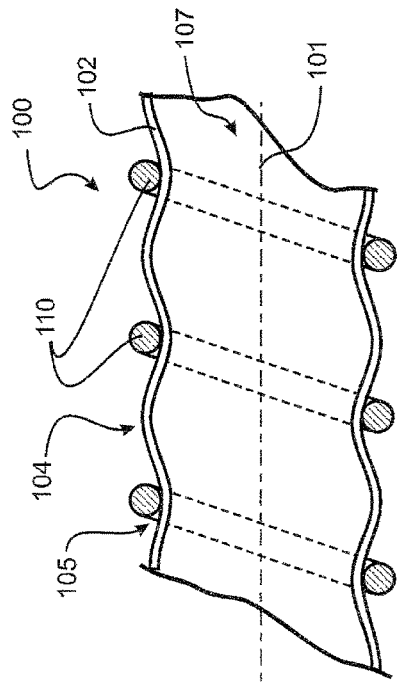
FIG. 3D is a side elevation a further embodiment where a tubular body is heat shrunk onto an internal form.

The tube of FIG. 3D is of a generally heat shrunk construction. The tube is made by placing an internal form (e.g. a coil spring) within a length of a tubular body that is thin walled and formed of a heat shrinkable tubing or energy. Heat (or energy appropriate to cause a material shrinkage) is then applied which causes the tubular body to shrink down and cling tightly to the internal form (e.g. spring), and in the open spaces along the wall between subsequent wall sections supported by the internal form the shrinkage causes corrugations to form. This leaves a corrugated tube with an internal form (e.g. wire) reinforcement. Corrugations result in good flexibility. If the inner surface or face of the tubular body is pre-coated with a suitable adhesive the internal form and tube wall will be further attached or connected to each other.

Figure 3E:
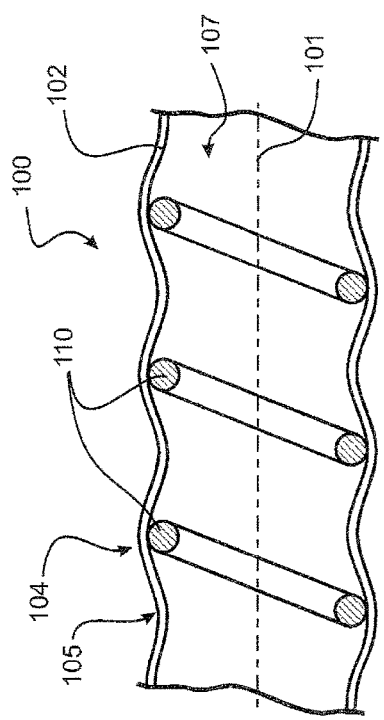
FIG. 3E is a side elevation a further alternative embodiment where an internal form operates to retain the tubular body in a desired form.

The tube of FIG. 3E is of a further alternative form. The tubular body can be formed (e.g. by extrusion) and then pulled or drawn through or within internal form 110. The internal form 110 can therefore substantially surround the tubular body (i.e. internal form becomes an form which is external of the tubular body). See for example FIG. 3E. The internal form 110 performs to support or retain the tubular body 102 in a desired form, shape or configuration. As with some of the other embodiments described herein the internal form 110 performs to define a series of alternating crests and troughs, a perimeter of the internal form defining the troughs 105. The region of the crests 104 between the supported sections (by the internal form 110) not being directly supported by the internal form 110. An advantage of this construction and configuration is further reduced need for the internal form 110 to be pre-coated for biocompatibility or sterility (e.g. hygiene) reasons such a form 110 may however be pre-coated to reduce corrosion or other effects from environmental conditions.

Some advantages of coating the internal form with a suitable material include:
- improving the overall strength and durability of the tube by more securely fixing the internal form to the tubular body.
- reinforcing the tubular body to improve resistance to swelling and degradation caused by exposure to chemicals.
- improving biocompatibility or sterility by increasing the range of permissible materials that can be used for the internal form as the coating presents a biocompatible (or sterile) barrier or layer of material around the internal form itself (also allowing the internal form to be colored to improve aesthetics and/or product recognition).
- protecting the internal form from the contents of the tube (to reduce corrosion and/or other degradation of the internal form).

Coating the internal form with a suitable material may assist in mitigating any tendency of the internal form to separate from the tubular body when the bond is stressed, as may happen when certain materials swell from exposure to certain chemicals (such as oils, alcohols and/or detergents) or in breathable materials when exposed to water vapor or aqueous solutions.

In various embodiments (e.g. FIGS. 1, 2, 3, 24A and 24B) the internal form supports the tubular body and resists narrowing and constriction of the tube lumen. The tubular body is beneficially formed from, formed of, or comprises a suitable polymer, such as a thermoplastic elastomer, a propylene based elastomer, a liquid silicon rubbers (LSR), a breathable thermoplastic polyurethane, or a breathable polyamide. Polymers may be those such as, but not limited to, polyolefins, thermoplastic elastomers, or breathable thermoplastic elastomers, for example, thermoplastic elastomer families, such as styrene block copolymers, copolyester elastomers, or thermoplastic polyolefin elastomers or thermoplastic polyurethane elastomers, or breathable polyamides. Use of breathable materials for forming the tubular body may also be utilized, thereby providing further benefits of breathability for such medical tubing or circuit. Particularly suitable polymer materials are those with a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90. Such materials may also be used for constructing of the nasal cannula arrangement as described in further detail below.

The tubular body may be formed from, formed of, or comprise a variety of thermoplastic polyurethanes, thermoplastic polyester elastomers or liquid silicon rubbers (LSR), including breathable grades. Advantageously, the material grades selected have beneficial mechanical properties (such as durability, tear resistance and high elasticity) and may optionally provide for good clarity so that any pooling of water within the tube can be detected.

The coating may be formed from the same material as the tubular body or a different material. Advantageously, the coating 1111 may be chemically compatible with the tubular body 1102 so that the coating 1111 and the tubular body 1102 may be welded together to form a bond linking the internal form 1110 to the tubular body 1102. The internal form may be fabricated from suitable polymers of other materials that are chemically compatible with the materials of the tubular body 1102. In one form, the coating 1111 may be a non-breathable material (even though the tubular body 1102 may be), so that the internal form 1110 is isolated from any moisture in the lumen of the tube. Advantageously, both the tubular body and the coating may be formed from, formed of, or comprise durable thermoplastic polyurethanes (TPU's). Where the tubular body is formed from, formed of, or comprises thermoplastic polyurethane, the coating may alternatively be formed from, formed of, or comprise a variety of polymers. Advantageously, the polymer grade selected for the coating is tough and has good wear resistance to enable the internal form to be manipulated after coating (such as being wound into a helical form).

Further, the tubular body can be extruded or otherwise formed such that the wall is of a minimal thickness to reduce the weight of the tube, further improving the flexibility characteristics of the tube. The internal form 110 can be fabricated from an elastic material, such as a suitable metal or polymer, to accommodate further bending.

Advantageously, the minimal wall thickness of the tubular body embodiment helps to facilitate the improved tube flexibility. Further, such a characteristic benefits those tubes formed of breathable materials, the breathability of such medical tubing being enhanced by the reduced or minimal wall thickness. Such a combination of reduced or minimal wall thickness and breathable material usage, in combination, may be particularly advantageous when used as part of a medical breathing circuit or system.

The construction of the tube enhances extensibility by accumulating an ancillary length of tubular body suspended in the troughs between the reinforcing ribs of the internal form 110.

As shown in an alternative embodiment FIG. 3E, extensibility is provided by the ancillary length of tubular body suspended in the crests between the troughs formed by internal form 110 acting in tubular body.

The ancillary length of wall permits the pitch of the internal form to fluctuate, so that the tube can stretch and compress longitudinally without significantly narrowing the lumen. Buckling and straightening of the ancillary length allows the tube to stretch and compress longitudinally with minimal tensile or compressive deformation or stress in the tube wall itself.

Flexibility of the tube also is improved by allowing the spacing between adjacent reinforcing ribs to vary about the tube circumference to accommodate bending. Circumferentially altering the rib spacing permits the internal form to simultaneously extend and condense on opposing sides of the tube to accommodate bends in the lumen without pinching or kinking the tube while still meeting the requirements for flexibility defined by ISO 5367:2000(E) (Fourth edition, 2000, Jun. 1).

In addition, the internal form may be electrically conductive. The electrically conductive internal form may facilitate a number of optional additional features for operation or use of such a tube. For example, the internal form can be (or may comprise) an electrically powered heater. For example, the internal form may comprise of one or more components.

In another embodiment, the internal form can comprise one or more electrically conductive members, electrically powered heaters or sensors (e.g., flow sensors, temperature sensors, humidity sensors, pressure sensors, or the like).

In some embodiments, the tube can comprise a heater, such as an electrically powered heater (e.g., a heater wire, heater circuit, or the like).

Provision of heating or heaters may assist in the maintenance of humidity of gas(es) passing through the tube and other related components. Heating may also alleviate problems associated with "rain-out." Provision of sensors advantageously assists in providing information feedback systems to help with associated heater control systems or information feedback to user monitor or monitoring systems.

It should also be appreciated the internal form 110 may be provided of a variable or varying pitch along a length of tubular body.

In yet further aspects of the invention, one or more internal forms 110 may be provided. In this manner, double helix forms of internal forms, or other configurations may be provided for supporting the tube, yet maintaining flexibility and extensibility of such a constructed tube.

The construction of medical tubing as previously described, and for example as illustrated in FIG. 1-3E, 24A, or 24B is particularly applicable for user interfaces where a short dedicated length of tube couples the interface to a breathing system. The flexibility and extensibility of the tubing is capable of compensating for patient movement, while the internal form 110 resists narrowing of the gas lumen (e.g., pinching, kinking and crushing) from forces attributable to this movement.

The tubing may be utilized for both adult and neonatal applications but is well suited for neonatal interfaces, where the dedicated tubing is smallest. For example, a neonatal interface tube according to the illustrated construction may have an internal diameter of tubular body (or lumen diameter) of about 1.5 mm to about 4.5 mm, an external diameter in the order of about 1.6 mm to about 4.6 mm and a wall thickness of about 0.05 mm to about 0.25 mm. Preferably, the internal diameter is about 2.4 mm to about 3 mm, the external diameter about 2.6 mm to about 3.4 mm and the wall thickness about 0.1 mm to about 0.2 mm.

The internal diameter of tubular body (or lumen diameter) may be about 1.5 mm to about 4.5 mm, or about 1.6 mm to about 4.4 mm, or about 1.7 mm to about 4.3 mm, or about 1.8 mm to about 4.2 mm, or about 1.9 mm to about 4.1 mm, or about 2.0 mm to about 4.0 mm, or about 2.1 mm to about 3.9 mm, or about 2.2 mm to about 3.8 mm, or about 2.3 mm to about 3.7 mm, or about 2.4 mm to about 3.6 mm, or about 2.5 mm to about 3.5 mm, or about 2.6 mm to about 3.4 mm, or about 2.7 mm to about 3.3 mm, or about 2.8 mm to about 3.2 mm, or about 2.9 mm to about 3.1 mm. The internal diameter (or lumen diameter) may be about 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, or 4.5 mm.

The external diameter of the tubular body may be about 1.6 mm to about 4.6 mm, or about 1.7 mm to about 4.5 mm, or about 1.8 mm to about 4.4 mm, or about 1.9 mm to about 4.3 mm, or about 2.0 mm to about 4.2 mm, or about 2.1 mm to about 4.1 mm, or about 2.2 mm to about 4.0 mm, or about 2.3 mm to about 3.9 mm, or about 2.4 mm to about 3.8 mm, or about 2.5 mm to about 3.7 mm, or about 2.6 mm to about 3.6 mm, or about 2.7 mm to about 3.5 mm, or about 2.8 mm to about 3.4 mm, or about 2.9 mm to about 3.3 mm. The external diameter may be about 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm or 4.6 mm. Preferably is about 3 mm to about 5 mm.

The wall thickness of the tubular body may be is about 0.05 mm to about 0.25 mm, or about 0.06 mm to about 0.24 mm, or about 0.07 mm to about 0.23 mm, or about 0.08 mm to about 0.22 mm, or about 0.09 mm to about 0.21 mm, or about 0.10 mm to about 0.20 mm, or about 0.11 mm to about 0.19 mm, or about 0.12 mm to about 0.18 mm, or about 0.13 mm to about 0.17 mm, or about 0.14 mm to about 0.16 mm. The wall thickness may be about 0.05 mm, 0.06 mm, 0.07 mm, 0.08 mm, 0.09 mm, 0.10 mm, 0.11 mm, 0.12 mm, 0.13 mm, 0.14 mm, 0.15 mm, 0.16 mm, 0.17 mm, 0.18 mm, 0.19 mm, 0.20 mm, 0.21 mm, 0.22 mm, 0.23 mm, 0.24 mm or 0.25 mm. Preferably is about 0.1 mm to about 0.2 mm.

The tubular body may have a corrugation depth of about 0.1 mm to about 0.5 mm.

A corrugation depth may be defined by the distance between a point of minimum radius from the longitudinal axis (mid-line) of the tubular body to a point of maximum radius from the longitudinal axis (mid-line) of the tubular body.

In one embodiment of the invention, the ratio of pitch of the internal form to outer diameter of internal form (e.g. outer-most diameter) is about 0.10 to about 0.50, more preferably the ratio is about 0.20 to about 0.35, even more the ratio is about 0.28 or about 0.29.

In another embodiment, the ratio of the internal form diameter (e.g. diameter of actual internal form element or member) to outer diameter of internal form (e.g. outer-most diameter) is about 0.02 to about 0.10, more preferably about 0.05 to about 0.07, most preferably the ratio is 0.06.

In yet a further embodiment, the ratio of the corrugations depth to the external (i.e. outer) tube diameter is about 0.05 to about 0.09.

Further, another embodiment may require that physical characteristics of the tubular body contribute to desired flexibility and/or structural support required by the tube.

Tubing of this size is viable for dedicated neonatal applications because the peak inspiratory flow requirements of a new born may be satisfied despite the restrictive gas flow lumen. The small size and weight of the tubing reduces pressure on the infant's face and reduces the visual intrusiveness of the interface. The flexibility and weight of the tubing increases user comfort and simplifies fitting and adjustment of the interface by a physician.

The internal form preferably is fabricated from a stainless steel wire, most preferably grade 302, 304 or 316, or other suitably elastic material with appropriate biocompatibility or sterility characteristics that can be wound into a helical skeleton of suitable size to support the tubular body. Ideally, the outer diameter of the helical skeleton is about 1.7 mm to about 4.4 mm, while the wire used to construct the skeleton may have a diameter of about 0.05 mm to about 0.3 mm. The pitch of the helical skeleton is preferably in the order of about 0.4 mm to about 1.8 mm to provide the desired tube flexibility, but may be about 1 mm to about 1.5 mm. Preferably the outer diameter of the helical skeleton is about 2.4 mm to about 3.4 mm, the diameter of the wire is about 0.15 mm to about 0.2 mm, and the pitch of the helical skeleton is about 0.8 mm to about 1.4 mm.

The outer diameter of the internal form (e.g. helical skeleton) may be about 1.7 mm to about 4.4 mm, or about 1.8 mm to about 4.3 mm, or about 1.9 mm to about 4.2 mm, or about 2.0 mm to about 4.1 mm, or about 2.1 mm to about 4.0 mm, or about 2.2 mm to about 3.9 mm, or about 2.3 mm to about 3.8 mm, or about 2.4 mm to about 3.7 mm, or about 2.5 mm to about 3.6 mm, or about 2.6 mm to about 3.5 mm, or about 2.7 mm to about 3.4 mm, or about 2.8 mm to about 3.3 mm, or about 2.9 mm to about 3.2 mm. The outer diameter of the helical skeleton may be about 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, or 4.4 mm.

The diameter of the internal form (e.g. wire used to construct the skeleton) may be about 0.05 mm to about 0.30 mm, or about 0.06 mm to about 0.29 mm, or about 0.07 mm to about 0.28 mm, or about 0.08 mm to about 0.27 mm, or about 0.09 mm to about 0.26 mm, or about 0.10 mm to about 0.25 mm, or about 0.11 mm to about 0.24 mm, or about 0.12 mm to about 0.23 mm, or about 0.13 mm to about 0.22 mm, or about 0.14 mm to about 0.21 mm, or about 0.15 mm to about 0.20 mm, or about 0.16 mm to about 0.19 mm. The diameter of the wire used to construct the skeleton may be about 0.05 mm, 0.06 mm, 0.07 mm, 0.08 mm, 0.09 mm, 0.10 mm, 0.11 mm, 0.12 mm, 0.13 mm, 0.14 mm, 0.15 mm, 0.16 mm, 0.17 mm, 0.18 mm, 0.19 mm, 0.20 mm, 0.21 mm, 0.22 mm, 0.23 mm, 0.24 mm or 0.25 mm, 0.26 mm, 0.27 mm, 0.28 mm, 0.29 mm, or 0.30 mm. Preferably is about 0.1 mm to about 0.4 mm.

The pitch of the internal form (e.g. helical skeleton) may be about 0.40 mm to about 1.80 mm, or about 0.45 mm to about 1.75 mm, or about 0.50 mm to about 1.70 mm, or about 0.55 mm to about 1.65 mm, or about 0.60 mm to about 1.60 mm, or about 0.65 mm to about 1.55 mm, or about 0.70 mm to about 1.50 mm, or about 0.75 mm to about 1.45 mm, or about 0.80 mm to about 1.40 mm, or about 0.85 mm to about 1.35 mm, or about 0.90 mm to about 1.30 mm, or about 0.95 mm to about 1.25 mm, or about 1.00 mm to about 1.2 mm, or about 1.05 mm to about 1.15 mm. The pitch of the helical skeleton may be about 0.40 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, 1.0 mm, 1.05 mm, 1.1 mm, 1.15 mm, 1.2 mm, 1.25 mm, 1.3 mm, 1.35 mm, 1.4 mm, 1.45 mm, 1.5 mm, 1.55 mm, 1.6 mm, 1.65 mm, 1.7 mm, 1.75 mm, or 1.8 mm. Preferably is about 1 mm to about 1.5 mm.

In various forms of the invention, the internal form may be provided to the tubular body having a variable or varied pitch. In this manner, the pitch of the internal form can be of a varied pitch once a part of the constructed tube. Varied pitch may have particular advantages, including increased regions of strength/support or flexibility. Such systems may also be useful in supporting even thinner walled tubular bodies.

In yet a further embodiment, varied pitch allows variance of the density of internal form per unit length of the tube. Such a construction may be useful where the internal form or parts of the internal form is provided as a heating source or sensors for or of gases passing through the lumen.

The internal form 110 may comprise a single continuous wind of wire or multiple winds linked end on end to form a helical skeleton, element or rib. Alternatively, the internal form may comprise a plurality of discrete rings. The rings may be linked longitudinally along the tube. A wire, elongate polymer or other suitable coupling (including a plurality of wires or elongate polymers) may extend along the lumen of the tube to link the rings. Multiple links may be spaced about the circumference of the rings.

For neonatal applications, the tubing provides an alternative to the transparent PVC tubing typically used to support and supply breathing gases to a nasal cannula. Preferably, the user interface is supported independently of the interface tubing (e.g., dedicated dermal pads) so that movement of the tubing is not restricted and the tube may be more pliable.

Tubing Fabrication Methods

In addition to that previously described, a medical tube may be fabricated by providing a tubular body about an internal form (or in alternative embodiments, by an internal form about a tubular body). The tubular body defines a lumen that generally encloses the internal form. During fabrication, in one embodiment, a reduced pressure may be applied within (or to) the lumen such that the reduced pressure draws the tubular body radially inward of the lumen and of an outer-most perimeter defined by the internal form. The outer-most perimeter of the internal form may define a plurality of alternating crests and troughs along a length of the tubular body. The tube may also be produced with a smooth outer surface as illustrated in FIG. 24B. In another embodiment, during fabrication, an extension (or stretch) may be applied to at least a part or a region of the tubular body enclosing the internal form, such that release of the extension (or stretch) returns (or allows) the extended (or stretched) part or region of the tubular body to draw radially inward of the lumen and of an outermost perimeter defined by the internal form, the outer-most perimeter defining a plurality of alternating crests and troughs along a length of the tubular body.

In yet a further embodiment, a combination of both applying a reduced pressure in the lumen and an extension (or stretch) to the tubular body may be implemented for fabricating the tube.

Figure 4:
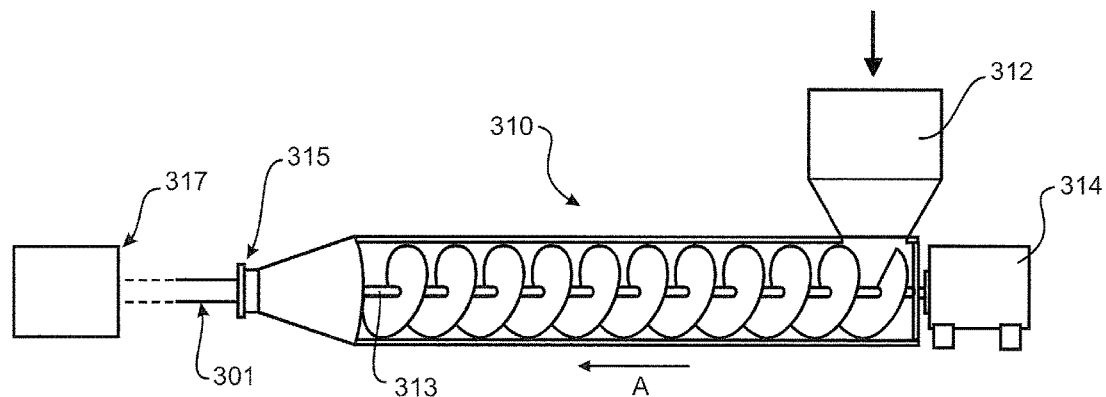
FIG. 4 is a schematic representation of apparatus for forming medical tubing, which apparatus includes a hopper, a feed screw and a die head.
Figure 5:
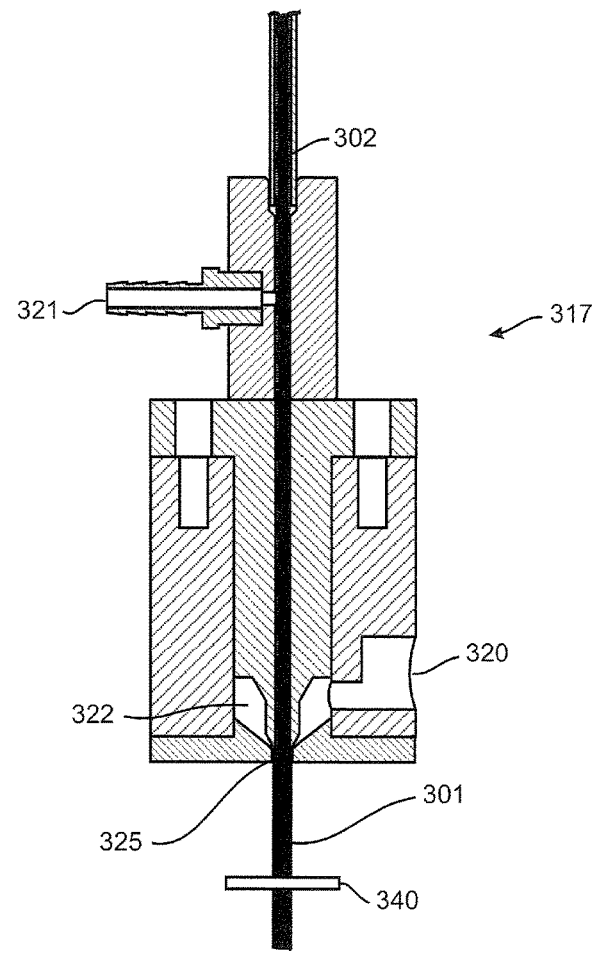
FIG. 5 is a schematic representation of the die head used for forming a reinforced medical tube.
Figure 7:
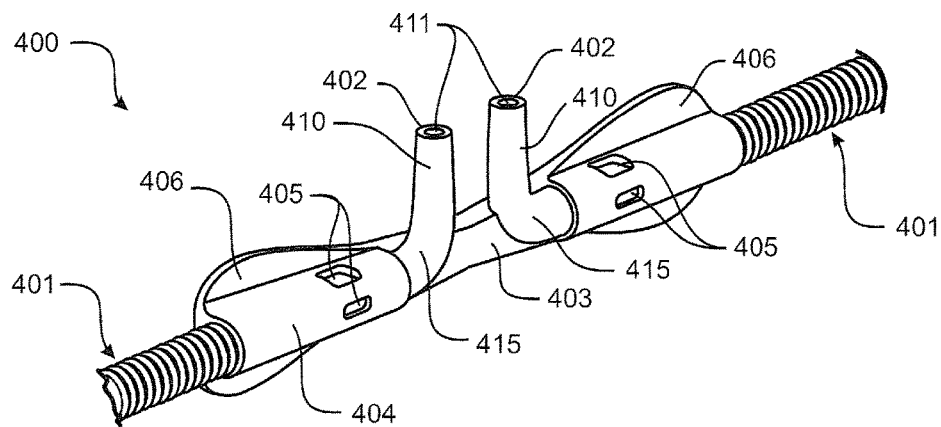
FIG. 7 is a perspective view of the nasal interface of FIG. 6 incorporating a backing component to stabilize the interface in position and to receive a headgear attachment.
Figure 8:
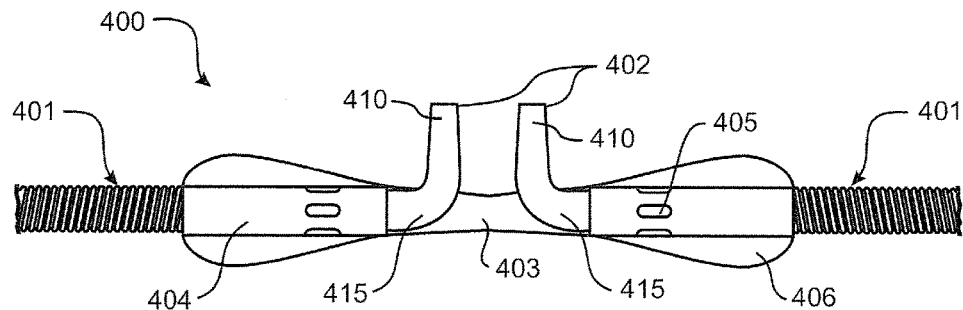
FIG. 8 is a front elevation of the nasal interface of FIG. 7.
Figure 9:
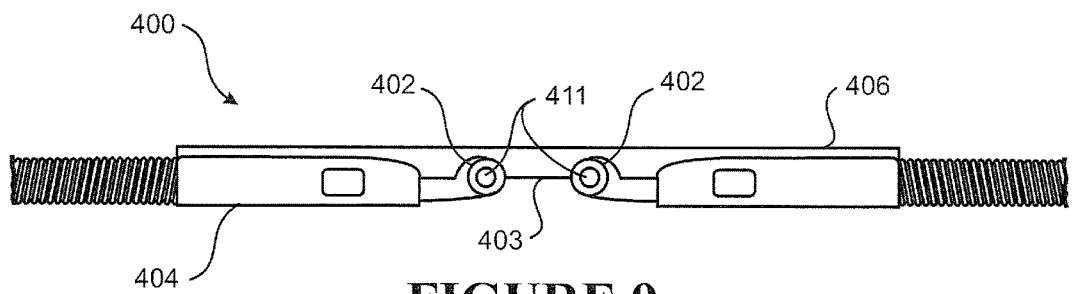
FIG. 9 is a top elevation of the nasal interface of FIG. 7.
Figure 10:
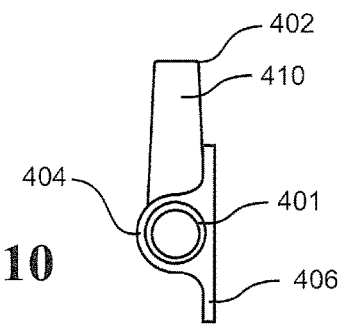
FIG. 10 is a side elevation of the nasal interface of FIG. 7.

An apparatus for fabricating reinforced medical tubing is illustrated in FIGS. 4 and 5. The illustrated apparatus comprises an extruder 310 and an associated die head 317. Raw material (typically thermoplastic beads, but could be any other form of raw material as a master batch) is fed into the extruder, where it is heated, and pressed or passed through the die head 317 to form the tubular body of a medical tube 301, such as the tubes discussed above. The tube 301 is subsequently advanced through an air wipe 340 where compressed air is passed over the tube 301 to cool the tubular body.

An apparatus for gripping or applying the extension (or stretch) to the tubular body can be utilized. In such manner the tubular body is allowed to stretch over or about the internal form, and then on release of the extension (or from the stretched condition) come into a gripping relationship with the internal form, and thus taking the shape of the outer-most perimeter defined by the internal form.

The potential materials that may be used to form the tubular body include thermoplastic elastomers, propylene based elastomers, thermoplastic breathable polyester elastomers, liquid silicon rubbers (LSR) and breathable thermoplastic polyurethane, or breathable polyamide, such as those with Shore A of about 30 to about 90, as discussed above.

The raw material for the tubular body is fed into a top mounted hopper 312, for example. The hopper 312 funnels the raw material into the barrel of the extruder 310 under the influence of gravity or another suitable feeder system. A feed screw 313 is housed within the extruder barrel and advances the material along the barrel toward the die head 317. The feed screw 313 is coupled to a rotational drive 314, which rotates the screw about its longitudinal shaft.

The material is heated to a molten or semi-molten state inside the barrel. The barrel may be actively heated or the friction generated as the material moves along the barrel may be sufficient to melt the material.

A suitable extruder for fabricating medical tubing is supplied by Welex. A Welex extruder equipped with a 30-40 mm diameter screw and typically a 12-16 mm annular die head with gap of 0.5-1.0 mm has been found to be suitable for producing low cost tubes quickly. Similar extrusion machines are provided by American Kuhne (Germany), AXON AB Plastics Machinery (Sweden), AMUT (Italy), and Battenfeld (Germany and China), for example.

To facilitate co-extrusion of the tube components, the raw material for the tubular body may be fed tangentially into the die head 317. The tubular body then can be extruded over the internal form as the internal form is advanced through the die head 317, with the molten or semi-molten tubular body being laid over the internal form. The molten tubular body preferably adheres to the internal form as it cools, securing the tube components together.

In the illustrated embodiment, the die head 317 (illustrated in FIG. 5) is adapted for arrangement normal to the barrel of the extruder 310, with a side port 320 positioned adjacent the extruder outlet 315. The molten or semi-molten material exiting the extruder 310 is fed into the side port 320 in the die head 317 and released into a circumferential chamber 322. The circumferential chamber 322 exits in a nozzle 325 through which the internal form 302 is drawn. The pressure created by the extruder 310 forces the material through a constriction 325 about the internal form 302 so that the tubular body 301 is extruded directly over the internal form. Preferably, the internal form is continuously advanced through the die head 317 at a substantially constant rate (although the rate of advance may be modulated to alter the thickness along the tubular body at a constant rate of extrusion).

Suction is applied to the interior of the die head through a vacuum port 321. The suction reduces the pressure within the lumen of the tube following extrusion, causing the molten or semi-molten tubular body to be drawn in about the internal form and creating a corrugation in the outer surface of the tube. Preferably the material of the tubular body is still sufficiently glutinous from the extrusion process to adhere about the internal form.

Application of the reduced pressure within or to the lumen of the tubular body may be by application of, for example, a vacuumous or reduced pressure to the passage of the lumen. Alternatively, the reduced pressure may be a relative or comparatively reduced pressure. For example, the pressure surrounding the tubular body may be increased such that the pressure within the lumen is then relatively less than the pressure surrounding the tubular body. In this manner, the tubular body experiences a pressure differential that encourages the tubular body to be drawn (or pushed) radially inward. The pressure within the lumen and outside of the tubular body may therefore be any suitable pressure such that the lumen is of a comparatively lesser pressure than the pressure surrounding the tubular body. Accordingly, the internal surface of the lumen is then drawn or pushed (by the pressure differentially) into contact with the internal form, thus forming or taking the shape of the outermost perimeter of the internal form in the embodiments illustrated in FIGS. 1, 2, 3 and 24A. Portions of the tubular body may be unsupported by internal form and may be drawn further radially inward than the outermost perimeter of the internal form, thus further accentuating the shape defined by the internal form.

Where the internal form is coated (for example as used in the tubes of FIGS. 24A and 24B), the coating may have to be shielded from any source of excessive heat to avoid damage. In one particular embodiment, the internal form may be fabricated from a metallic wire formed from medical grade stainless steel (although non medical grade materials may also be used with an encapsulating coating that presents a biocompatible layer or sterility and corrosion barrier). The wire can be encapsulated in a suitable coating by drawing the wire through a material bath. The raised temperature of the coating material in the bath may also partially sterilize the wire by killing any biological contaminants.

For example, coating the wire with a suitable polymer grade may involve drawing the wire through a bath of molten polymer at temperatures in excess of 150° C., but may for example be more than 180° C. or about 200° C. (temperatures sufficient to enable a polymer melt to coat the surface of an internal form). The wire may then be fabricated into an internal form when the coating has cooled sufficiently. The internal form may fabricated by spirally winding the coated wire about a mandrel.

In other examples, the internal form may be coated or encapsulated via a dip process through a bath containing polymer or through an extrusion die head applying polymer to the internal form.

Other Applications

It is anticipated that the present embodiments will find other medical applications to which it is particularly suited. For example, applications involving medical tubing that are desired to be lightweight and highly flexible with sufficient resistance to crushing, pinching and kinking may also include the delivery and exhaust limbs of a surgical humidification system, including those applications where the use of breathable medical tubing is preferred.

User Interface

Figure 12:
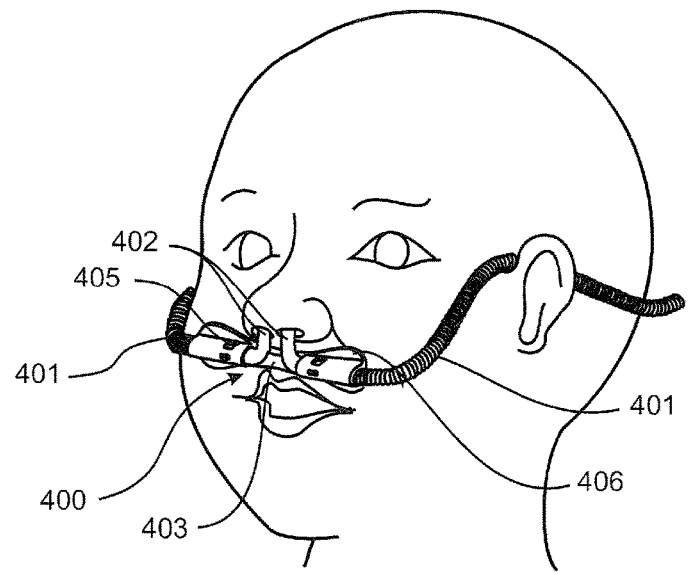
FIG. 12 is a perspective view of the nasal interface of FIG. 7 in position on an infant's head.

The tube may be incorporated into a user interface, such as a nasal cannula, for delivering breathing gases to a user. A nasal interface incorporating the tube is illustrated in FIGS. 6 to 12. The illustrated interface 400 comprises a pair of nasal prongs 402. Each prong 402 is coupled to the terminal end of a tube 401. The other end of the tubes 401 can be coupled to a supply conduit to interconnect the prongs 402 to a respiratory system. The tubes 401 may be coupled to individual supply conduits or alternatively merged (e.g., by a Y coupling or other suitable connector, such as a manifold, for example) to form a single junction with a supply conduit and to facilitate delivery of breathing gases to the interface 400. An embodiment of the user interface 400 is illustrated in FIG. 12 fitted to an infant.

Each prong 402 defines a lumen that extends between a user end 410 and a tube end 415 of the prong 402. The tube end 415 of the prong 402 couples the prong 402 to the interface tube 401. The user end 410 of the prong 402 is configured to deliver respiratory gases to a user's nare and incorporates an aperture 411 for this purpose. The aperture 411 can be arranged concentrically with the terminal end of the prong 402 so that there is minimal disturbance to flow exiting the prong 402. The tube end of the prong 402 can be anatomically shaped and/or conform closely to a user's nare, with the terminal end of the prong 402 (i.e., the end incorporating the aperture 411) being curved away from the septum, for example, to reduce the likelihood of irritation.

The user end 410 and the tube end 415 of the prong 402 are connected by an arcuate elbow joint. The user end 410 and the tube end 415 are disposed generally normal in the illustrated embodiment, with the elbow joint passing through approximately 90°. Beneficially, in one form the elbow joint can have a smooth transition (corresponding to a greater radius of curvature) between the adjacent sections of the prong 402 to minimize flow disturbances within the prong 402.

The interface tube 401 couples to the tube end 415 of the prong 402. Preferably the prong 402 is moulded over the tube 401 to create an integrated component. In the illustrated embodiment, the tube 401 and the tube end section 415 of the prong 402 are arranged concentrically with the prong 402 extending about the tube 401. Preferably the majority of the tube end section 415 is formed over the tube 401 to increase the contact surface area and strengthen the joint between the prong 402 and the tube 401.

The prongs 402 preferably are held in spaced relation. A backing or harness 403 is coupled to both prongs 402 in the illustrated embodiment. The backing 403 preferably retains the prongs 402 in fixed spaced relation. Different interface 400 sizes may be produced to accommodate variations in nasal spacing.

The illustrated backing 403 also includes a housing 404 that generally encloses or captures at least a portion of the tube end 415 of the prong 402. The housing 404 incorporates a coupling 405 that can be used to affix headgear for retaining the interface 400 in position. A pair of outriggers 406 project outwardly from the backing 403 on either side of the tube 401. The outriggers 406 increase a contact surface between the interface 400 and a patient, which distributes the interface retention force over a greater area and reduces the pressure applied to a user's face.

The user side face of the backing 403 and outriggers 406 (i.e., the side that rests against the face of a user) may be contoured to reflect anticipated anatomical structures. The backing 403 and the outriggers 406 also may be formed from a flexible material to allow the structure to adapt to a particular individual's face.

Outriggers may comprise a portion that enables a user (or carer) to more easily pull or tear-off the outriggers 106 from a user's skin or from dermal patches. Such tabs may improve the ease of application/removal of an interface from a user.

Figure 13:
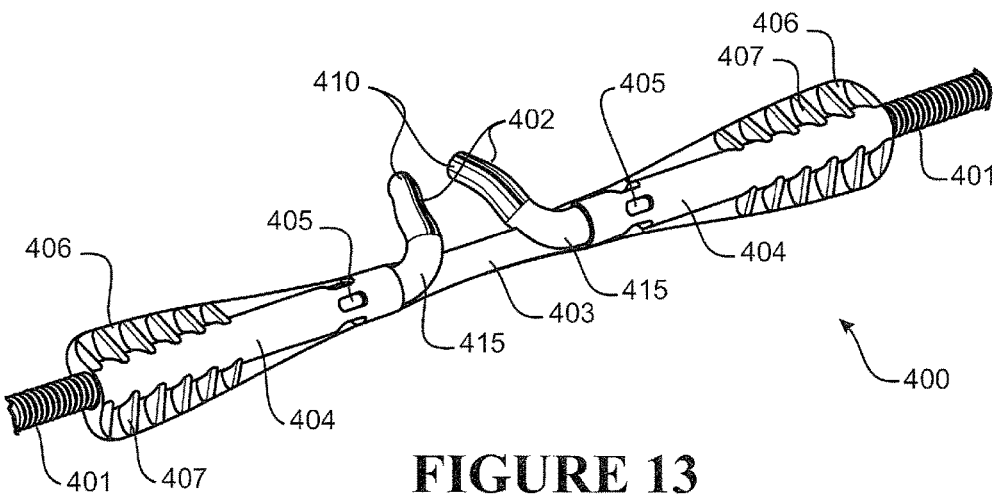
FIG. 13 is a perspective view of a nasal interface incorporating a pair of reinforced medical tubes each coupled to a nasal prong, wherein the respective nasal prongs are secured to a harness that includes a plurality of ribs and a pair of headgear attachments.
Figure 14:
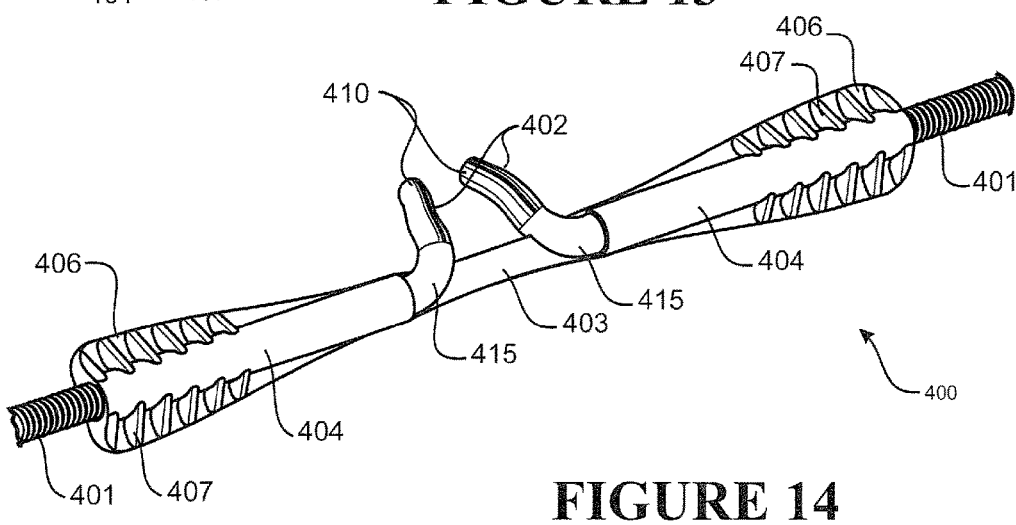
FIG. 14 is a perspective view of a nasal interface incorporating a pair of reinforced medical tubes, each coupled to a nasal prong, the respective nasal prongs are secured to a harness that includes a plurality of ribs.

The housing 404 may incorporate ribbing 407, which is illustrated in FIGS. 12 and 13, between a front face of the outriggers 406 and the portion of the housing 404 that connects with the prong 402 and the interface tube 401. The ribbing 407 increases the interface contact surface available for medical taping to adhere when fastening the interface 400 to a user. The ribbing 407 may also increase the torsional stiffness of the outriggers, which helps stabilize the prong 402 position.

The prongs 402, the backing 403 and the outriggers 406 preferably are fabricated from a suitable polymer. Preferably, the individual cannula (e.g., the prong 402 and the tube 401) are fabricated by over moulding the prong 402 about the exterior of the tube 401. The over moulding process generally involves inserting a terminal end of the pre-formed tube 401 into a suitable mould and restraining the tube 401 while the material used to fabricate the prong is injected into the mould about the tube exterior. Advantageously, both of the prongs 402, the backing 403 and the outriggers 406 are fabricated in a single over moulding process to form a complete integrated interface.

Figure 27A:
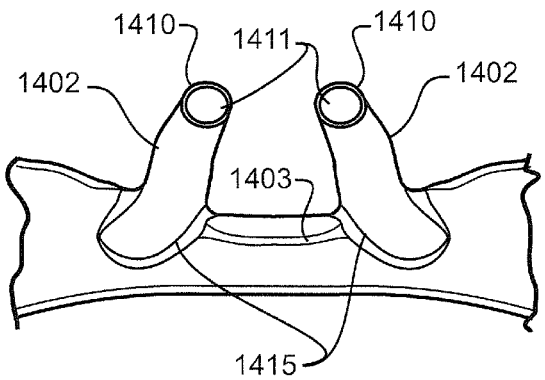
FIG. 27A is a close up of the nasal prongs illustrated in FIG. 17D.
Figure 27B:
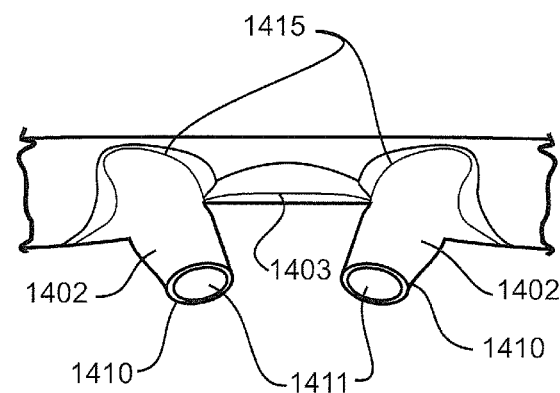
FIG. 27B is a close up of the nasal prongs illustrated in FIG. 17C.

Configuration or design of the prongs may take various forms. In one preferred embodiment, the prongs and/or cannula that are over-moulded with the delivery tube may be as described in US Patent Publication No. 2010/0192957, which is hereby incorporated by reference in its entirety.
Prongs The geometry of another preferred form of nasal prong is illustrated schematically in FIGS. 25A to 25D, in combination with a common base support and facial support pads in FIGS. 26A to 26D and in close up in FIGS. 27A and 27B. The numerated features of the prongs illustrated in these features are identified with similar numerals (but prefixed to differentiate the particular embodiments) as the same features present in the previous Figures (FIGS. 6 to 13).

The geometry of the prongs 1402 in FIGS. 25A to 25D is illustrated with swept lines 1420, that represent the prong trajectory, and ellipses 1130 to 1135, that represent the shape and orientation of the lumen within each prong at a particular trajectory. Each prong 1402 follows a swept path that is shaped to follow the anatomical geometry/curvature/contours of a user's nare. The prongs are moulded or formed to follow the anatomical shape and curvature of a user's nare. Advantageously the prongs may maximize clearance between the prong and the internal structure of the nostril by anatomically matching the nostril path.

In one preferred form the prongs are premoulded or preformed according to the anatomical shape of a nare, in contrast to prongs which are of a material that is conformable to the anatomical shape of a nare.

The geometry of the illustrated prongs is described below with respect to how the interface is held on a user's face when in use. The interface is arranged so that the prongs 1402 are arranged generally symmetrical about the sagittal plane of a user. Each prong extends from a base 1415 disposed on a common support that extends along a user's upper lip. The prongs 1402 are spaced apart on the support to avoid the user's septum. The spacing between the prongs 1402 at the base 1415 is selected to present the greatest clearance between the prong and the user's septum (at the base of the nose) for the range of facial sizes that each interface accommodates (i.e. for a particular interface size).

The initial phase of each prong trajectory 1420 prior to the base 1415 is represented by the ellipses 1130 and 1131 (the first phase). During this phase the prongs extend substantially coaxial with the respective breathing tubes. Both trajectories 1420 sweep a path that generally extends along the user's upper lip, toward the septum from either side of the sagittal plane. The prongs 1402 sweep through a slight rearward or posterior curve (toward the user's coronal plane) with respect to the user's upper lip, as illustrated by the rotation of the lumen (represented by the changing orientation of the ellipses 1130, 1131 and 1132). The internal flow path defined by the shape of the lumen remains generally circular during this phase.

From the base 1415 each prong 1402 sweeps upwardly or superiorly toward the crown of the user's head (away from the transverse plane) and rearwardly or posteriorly (toward the user's coronal plane) with respect to the user's upper lip. Between the ellipses 1131 and 1133 (the second phase) the lumen of the prongs smoothly transitions from a generally mediolateral orientation along the user's upper lip to a predominantly inclined posterior orientation directing gas flow toward an upper portion of the back of a user's head. The lumen of the prong reduces slightly during this phase, becoming more elliptical to take advantage of the space available within the nostril.

In the third phase (between the ellipses 1133 and 1134) the prongs continue along an inclined posterior trajectory toward the upper back of a user's head (away from the transverse plane and toward the coronal plane), with a smooth reduction in the rate of incline (the superior component of the prongs trajectory 1420 causing the lumen to move away from the transverse plane). During this phase the prongs 1402 have negligible convergence (or mediolateral component) toward the sagittal plane. The prong lumen reduces further during this phase, becoming increasingly elliptical.

In the final phase (between the ellipses 1134 and 1135) the prongs 1402 continue along an inclined posterior trajectory with some mediolateral convergence toward to sagittal plane. The mediolateral convergence of the prongs 1402 begins at the illustrated trajectory inflection point at the start of the fourth phase (or slightly prior) adjacent the ellipse 1134. There is a second inflection point adjacent the final ellipse 1135 that reduces convergence of the prongs and orientates the prong outlet 1411 posteriorly (toward the coronal plane) with a slight mediolateral component toward the sagittal plane (represented by the orientation of the final ellipse 1135 in FIG. 25B).

The incline rate of the prong trajectories 1420 continues to decrease during the fourth phase, until the respective trajectories 1420 are substantially parallel with the transverse plane at the prong outlet 1411 (represented by ellipse 1135). The mediolateral and superior-inferior adjustments of the prong trajectories 1420 adjacent the final ellipse 1135 position the prong outlet 1411 generally in alignment with the passage of the upper airway to reduce soft tissue irritation caused by the exiting breathing gases. The prong lumen is elliptical at the outlet 1411, with the major elliptical axis arranged in a generally transverse plan. The outlet 1411 directs breathing gases upwardly or superiorly toward the crown of the user's head (away from the transverse plane) and rearwardly or posteriorly (toward the user's coronal plane).

The shape of the prongs 1402 illustrated in FIGS. 13, 14 and 25 to 27 (both the trajectory and lumen) avoid contact with the septum area of a user, thereby reducing the risk of injury to the tissue in this area. The prongs improve user comfort and treatment efficacy by aligning the prong outlet with the user's upper airways. The shape of the lumen maximizes the cross sectional area of the prong along its length, taking advantage of the anatomically available space in a patient's nare to minimize flow resistance. The prong lumen has a shape that avoids sealing in the user's nare.

An independent source of gases can be provided to each prong. In this manner, where a pair of prongs is used, one prong may supply breathing gas, while the other prong may provide medicament gases, such as those gases used to improve respiratory therapy or respiratory of a user.

Such anatomical prongs may have a shaped trajectory that fits the anatomical shape of the user's nostril. In a first portion (or phase) of such a prong, the trajectory moves horizontally towards the midline of the face. In a second portion (or phase) of the prong, the trajectory curves upwards directly into the nostril towards the crown of the head. In a third potion (or phase) of the prong, the trajectory rolls backwards into the head following the anatomical curvature of the nostril. And, in a fourth portion (or phase), the trajectory tilts horizontally towards the centre of the cannula to align the flow outlet with the user's upper airway.

Such anatomically shaped prongs have cross-sections that vary along the central trajectory. For example, the cross-sections are generally circular at the base of the trajectory and become generally elliptical towards the end of the trajectory or prong. Further, the cross-sectional diameter generally decreases along the trajectory from the first portion (or phase) to the end of the fourth portion (or phase).

The prongs are preferably fabricated from a soft compliant material to further reduce trauma to soft tissue in the nare. One example of a potential material is a biocompatible thermoplastic elastomer or liquid silicon rubber (LSR).

A nasal interface 1400 incorporating the prongs 1402 is illustrated in FIGS. 26A to 26D, 27A and 27B. The interface comprises the nasal prongs 1402, a common support that extends along a user's upper lip beneath the nose and supports the prongs 1402, a backing or harness 1403, a pair of outriggers or facial pads 1406 and integral tubing 1401, all spaced generally symmetrically about the sagittal plane. The prongs 1402 include a base 1415 and a user end 1410. The interface is formed as an integral or unitary component with the tubing 1401 linking directly to the base 1415 of the prongs 1402. The open distal end of each integrated tube 1401 is configured to receive a suitable breathing tube (such as tube 100). The breathing tube may be adhered or otherwise fixed to the interface tubing 1401. The facial pads 1406 are anatomically shaped with a distribution and scale of curvature that reflects the facial geometry of the intended user. The anatomical shape of the facial pads 1406 gives the interface a positive engagement with a user's face at a predetermined position where the contour of the facial pads 1406 matches the user's facial contour. The pre-shaped facial pads 1406 compliment the anatomical nasal prongs 1402 by improving the accuracy and speed with which the prongs 1402 can be placed and retained within a user's nares.

Pre-shaping or contouring the facial pads 1406 to the user's facial features reduces the pressure applied to the user's face by any retention mechanism (adhesive tape, headgear or other means). This reduces the likelihood of pressure sores. The positive engagement promoted by the anatomical shape of the facial pads 1406 increases the stability of the interface 1400 and the prong 1402 and therefore improves comfort and efficacy of the treatment being administered.

In a further embodiment, there is provided a nasal cannula arrangement 2000 comprising at least one nasal prong 2001, the or each prong 2001 having a gas outlet 2002 adapted to be inserted into a user's nare (or nares) and a gas inlet 2003 fluidly connected to the gas outlet 2001. A tube 2012 can be connected to the gas inlet 2003. The at least one nasal prong 2001 comprises a backing 2004, the backing 2004 configured to rest on a user's face, and where a lip 2005 extends about at least a part of the perimeter of a rear surface 2006 of the backing 2004. The rear surface 2004 is configured for receiving or retaining a user interface patch 2007. In use, the user interface patch 2007 may be releasably attachable or connectable to, or with, a dermal patch 2008 that is or can be affixed to a user's face.

Lips

The lip 2005 may generally perform as a barrier, which may provide for a seal, such as for example a fluid-tight seal. However, it will be appreciated the provision of the lip 2005 as a physical barrier, and not necessarily in a fluid-tight seal, may itself be sufficient to prevent a majority of fluids (such as nasal or oral mucus, or breast-milk or fluids used to wash the user's face) from seeping under the backing 2004 to the rear surface 2006.

Advantageously, the lip 2005 operates to prevent a majority of fluids from seeping under the backing 2004 to the rear surface 2006. Such seepage may otherwise impair the adhesion or connection between the user interface patch 2007 and a user's face or a dermal patch 2008 that is applied to a user's face. Such a series of patches providing a securement system for positioning of the cannula relative to the user's nares, or for facilitating the positioning of the nasal cannula in a preferred position or location. Such fluid seepage may alternatively become clogged in the user interface patch 2007 or interface facing surface of the dermal patch; such patch surfaces then may become odorous or generally slimy or unhealthy. Such impairment should preferably be avoid where possible, being unpleasant for users or their carers or perhaps even impacting on the ability for such a nasal cannula to otherwise remain in a preferred position. The provision of such a lip 2005 about the rear surface 2006 of the backing 2004 attempts to minimize one or more of such detrimental impacts.

According to this embodiment, the lip 2005 may be deformable. For example, the lip 2005 may be shaped such that a portion of the lip coming into contact with a user's face or a dermal patch 2008 is able to bend or flex. In this manner, when a pressure is applied to the lip 2005, such as by the force of engagement between the user interface patch 2007 and a dermal patch 2008, the lip 2008 can be allowed deform to more effectively conform to the shape to which it is contacting, improving the likelihood of a more effective seal or barrier to fluids.

Such a lip 2005 may extend at least about the perimeter (or a part of the perimeter) of the backing 2004, for example about a region that is substantially adjacent to an associated prong. For example, a majority of fluids to which the lip 2005 is configured to keep out from the rear of the backing are generated in the nasal or oral region of the user. That is, nasal mucus exiting the nare(s) of the user's nose, or oral mucus exiting a user's mouth which may dribble back toward the cannula's backing (depending on the positioning of the user's head), or even breast-milk leakage from an infant's mouth during breast feeding that then dribbles in to the region around the nasal cannula arrangement 2000. Further, bathing of an infant or user's face may generate fluids that dribble to the region about or around the cannula 2000.

All of these fluids (and others not necessarily mentioned above) may impact on the effectiveness of a securement patch system used for securing or positioning of the cannula on a user's face. Further, the negative impact generated by odours or mucus (or slime) clogging of the securement system patches is undesirable.

Accordingly, in one embodiment, a priority is to provide a lip 2005 about at least the region of the rear surface 2006 of the backing 2004 that extends from near or adjacent to the prong 2001 or nare of the user, to a region laterally away therefrom. In such an instance, the lip 2005 may not extend wholly about the perimeter of the backing.

Figure 35:
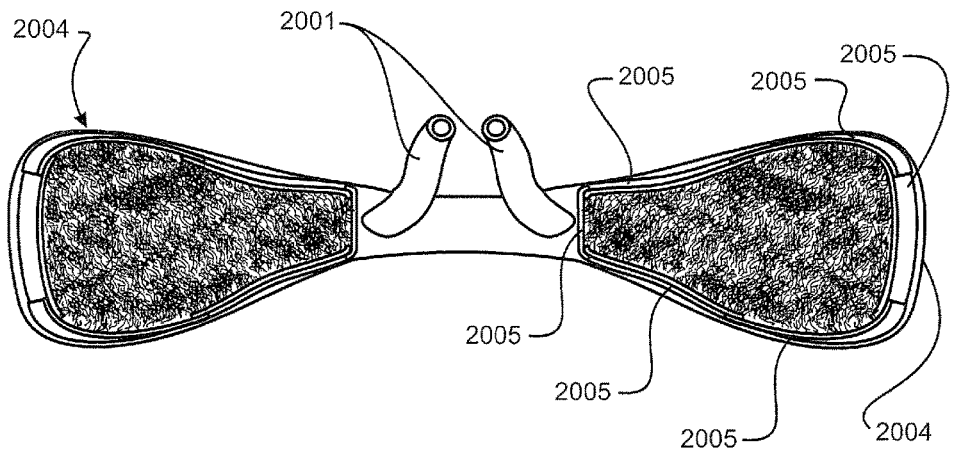
FIG. 35 is a rear view of an alternative nasal cannula arrangement of FIGS. 28 to 34 illustrating a series of segmented lips.

In other embodiments, the lip may be formed from a series of smaller or segmented lip portions that may or may not adjoin one another to help form a barrier or seal. For example, as shown in FIG. 35, a series of segmented lips may be provided that together extend partially, or wholly, about the perimeter of the rear surface 2006 of the backing 2004. The lip 2005 may be created or formed by a series of one or more separate lips, such as those shown by FIG. 35. Further, such segmented lip potions may be adjacent to one another, adjoining one another or even overlapping of one another in forming the lip 2005.

In this manner, together the lips may form a barrier or seal to intrusion by fluids.

However, it will be appreciated the lip 2005 could be provided to extend wholly about the perimeter of the backing. In such a case, the lip 2005 would be an endless lip.

The lip or lips may be formed (or treated to be) of a hydrophobic character or attributes, thereby further helping to reduce liquids from passing the lip barrier.

The lip potion in contact with a user's skin may be of a spoon shape. For example, the lip may have a profile effectively providing for a pair of parallel spaced apart lips, an outer perimeter lip and an inner perimeter lip of the lip as a whole. In this way, a set of lips each contact the skin of the user, helping to provide a more effective barrier or seal to liquids. It will also be appreciated that a series of parallel lips may be utilised.

As described previously, the backing 2004 may take the form of a substantially planar or flat or even contoured (such as a pre-formed curve as shown by FIGS. 28-34) backing that is configured to rest on a user's face. The backing 2004 may generally extend laterally outward from the at least one nasal prong 2001, away from the septum of a user. Such a backing 2004 can assist in operating as a stabilizer of the prong(s) 2001 in the nare(s) of a user. In this respect, such a backing 2004 may comprise of the various rib features as described in other embodiments.

It will also be appreciated the nasal cannula 2000 of this embodiment can have a pair of prongs 2001 for inserting into the nares of a user, each prong 2001 having an adjacent or associated backing 2004. Where a pair of prongs 2001 is provided, the prongs may be independent of each other, or may utilize a harness to structurally join the prongs together for additional stability, as previously described in other embodiments.

The cannula 2000 of this embodiment may additionally comprise the various features of fluidly connected (or integrally formed) tubing 100, 200, 400, 1100 as described herein, and/or may utilize the securement system 500, 600 of user interface patches and dermal patches as described herein, and/or may allow for the gas inlet to be fluidly connected to the reinforce medical tubing 100, 200, as described herein. Further, it will be appreciated the prongs 2001 may be any of those prong shapes or configurations as previously described herein, including the anatomically shaped prongs referred to by FIGS. 25A-27B.

One embodiment of the nasal cannula 2000 is as shown by FIGS. 28-34.

Figure 28:
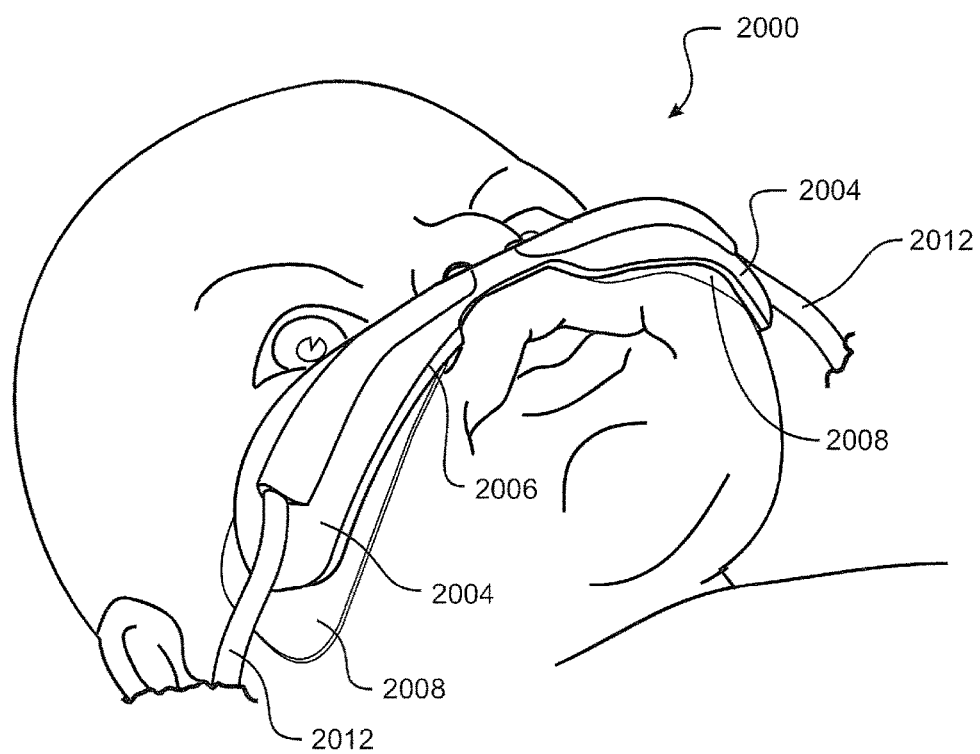
FIGS. 28 and 29 show a nasal cannula arrangement in use with a backing component comprising a lip.
Figure 29:
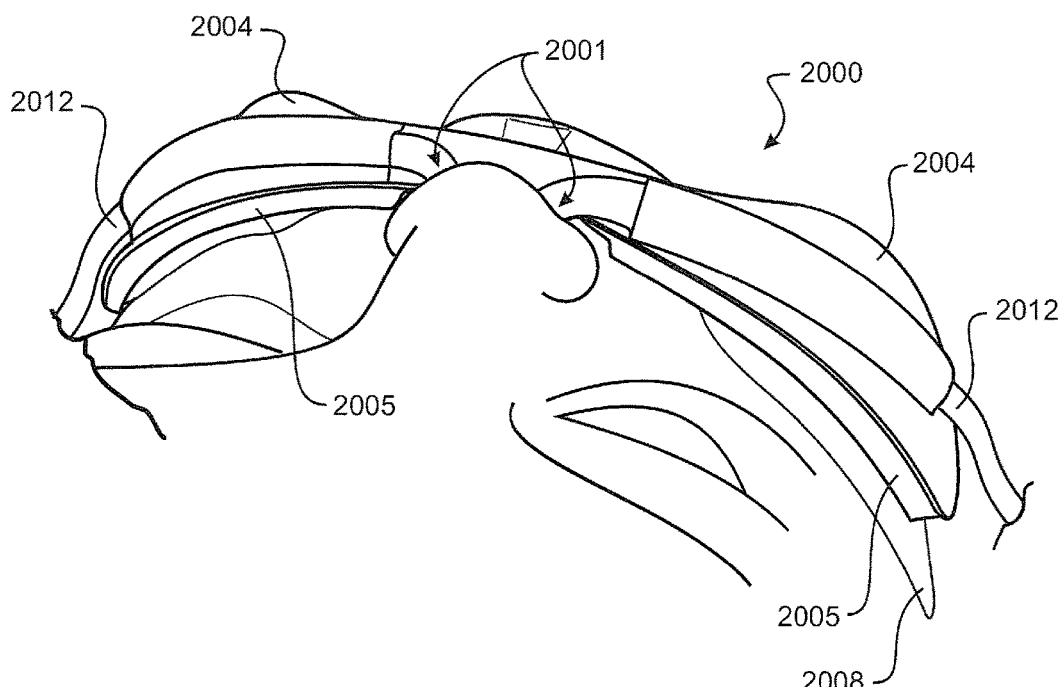
Figure 30:
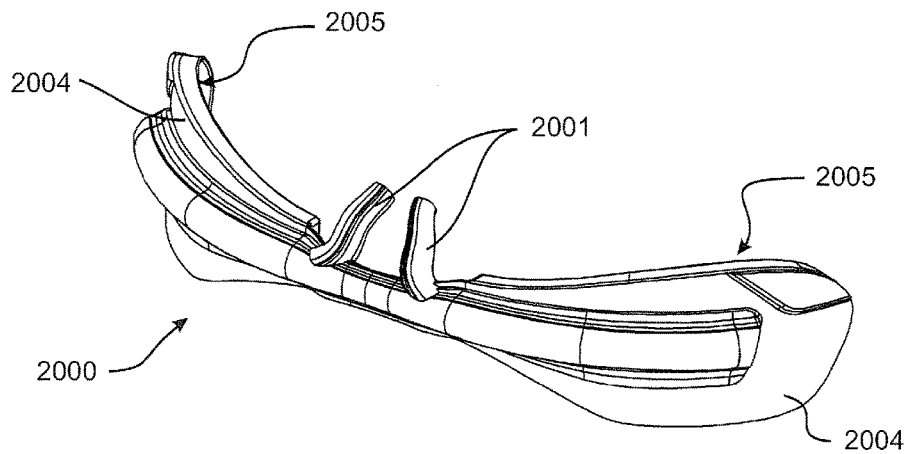
FIG. 30 is a front perspective view of a nasal cannula arrangement with a backing component comprising a lip.

FIGS. 28 and 29 show a cannula arrangement 2000 with backing 2004 in connection with a dermal patch 2008 affixed to a user's face. The lip 2005 is shown in contact with the dermal patch 2008, thereby providing a barrier to fluids that may otherwise leak to the underside of backing 2004 and the rear surface 2006 to which a user interface patch 2007 is retained. As shown, the user interface patch 2007 is located in-board of lip 2005.

FIGS. 30-34 show a nasal cannula 2000 in more detail.

Figure 31:
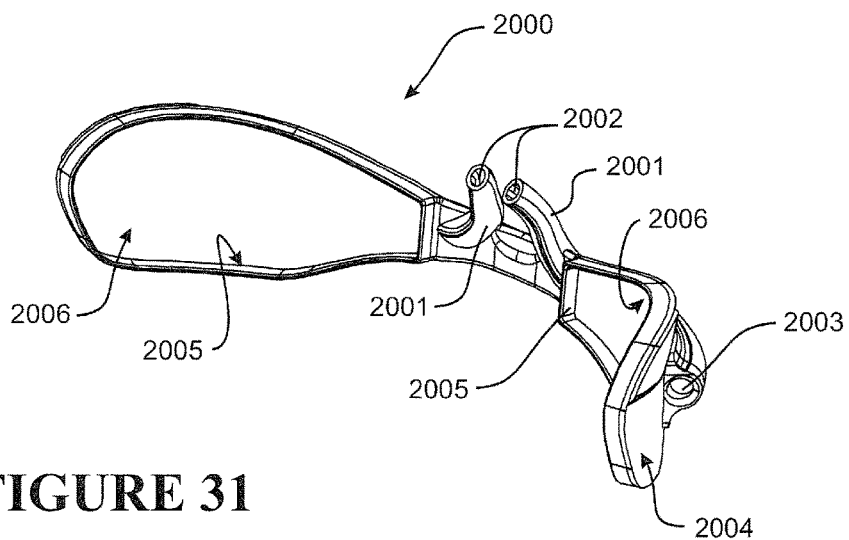
FIG. 31 is a rear perspective view of a nasal cannula arrangement with a backing component comprising a lip.
Figure 34:
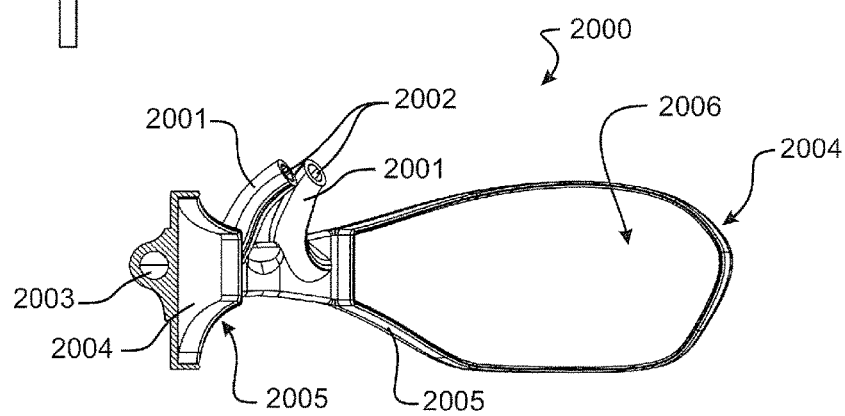
FIG. 34 is a side rear perspective view of the nasal cannula arrangement of FIGS. 30-33.

As shown by FIGS. 31 and 34, the rear surface 2006 can be initially provided without a user interface patch, i.e. the surface 2006 is configured to receive or retain a user interface patch 2007. Such a user interface patch 2007 may be connected to the rear surface 2006 by an adhesive or other suitable connection. Once the patch is then in position, it is ready to be connected to or receive a dermal patch.

Figure 32:
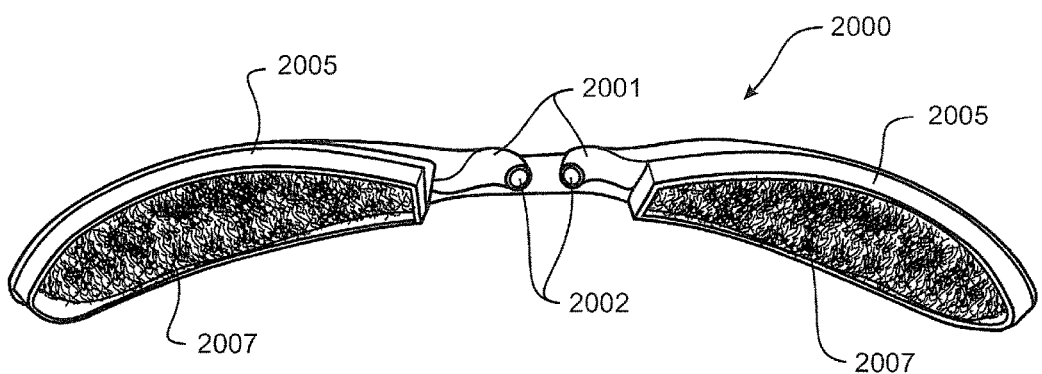
FIG. 32 is a top rear perspective view of a nasal cannula arrangement with a backing component comprising a lip and a user interface patch on a rear surface of the backing component.

In one form, the user interface patch may be one part of a two-part connection system, for example the loops of a hook and loop system. In such an instance, the interface facing surface of a dermal patch 2008 would comprise of hooks that are engageable with the loops of the user interface patch. See FIG. 32 illustrating rear surface 2006 retaining a user interface patch with loops ready for connection to the hooks of a dermal patch.

Figure 33:
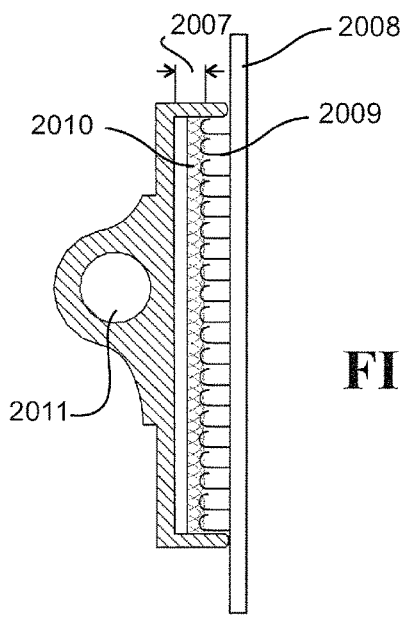
FIG. 33 is a cross sectional view through the nasal cannula arrangement of FIG. 32 when user interface patch is in connection with a dermal patch.

FIG. 33 shows a section through a cannula 2000 with the hooks 2009 of a dermal patch engaged with the loops 2010 of a user interface patch. Also shown is lumen 2011 or gas passage pathway for gas being supplied to the gas inlet of the cannula for delivery to the gas outlet 2002 of prongs 2001.

Securement System

Figure 15:
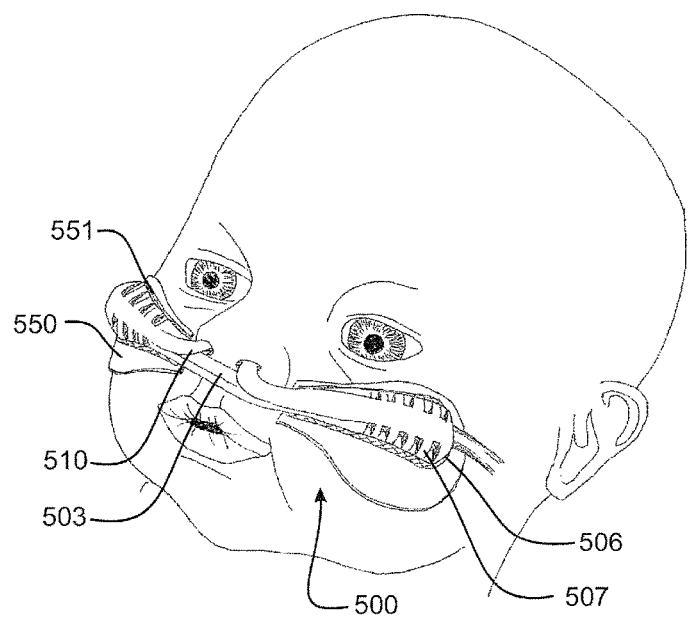
FIG. 15 shows a nasal cannula positioned in an operative position on the face of a user, the cannula positioned according to an embodiment of the seventh aspect.
Figure 16:
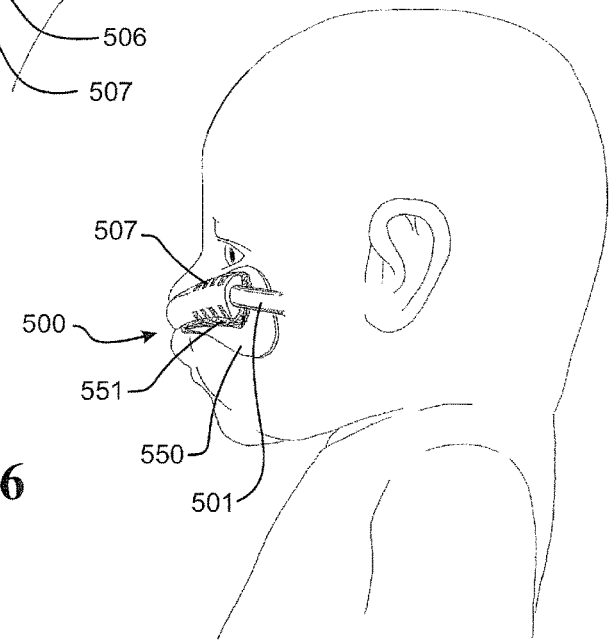
FIG. 16 is a side view of the nasal cannula arrangement of FIG. 15.
Figure 17:
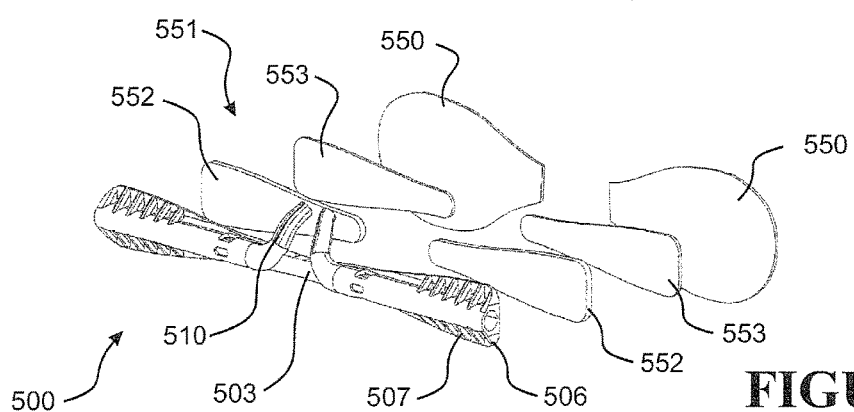
FIG. 17 shows an embodiment according to the seventh aspect and its constituent assembly components.
Figure 19:
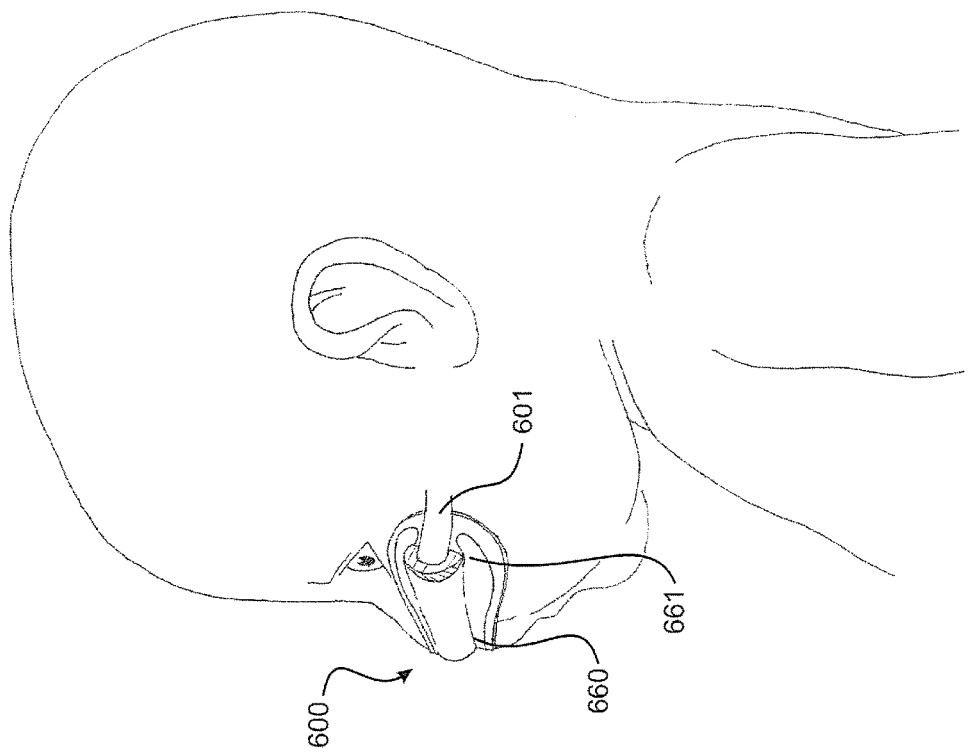
FIG. 19 is a side view of the nasal cannula arrangement of FIG. 18.
Figure 18:
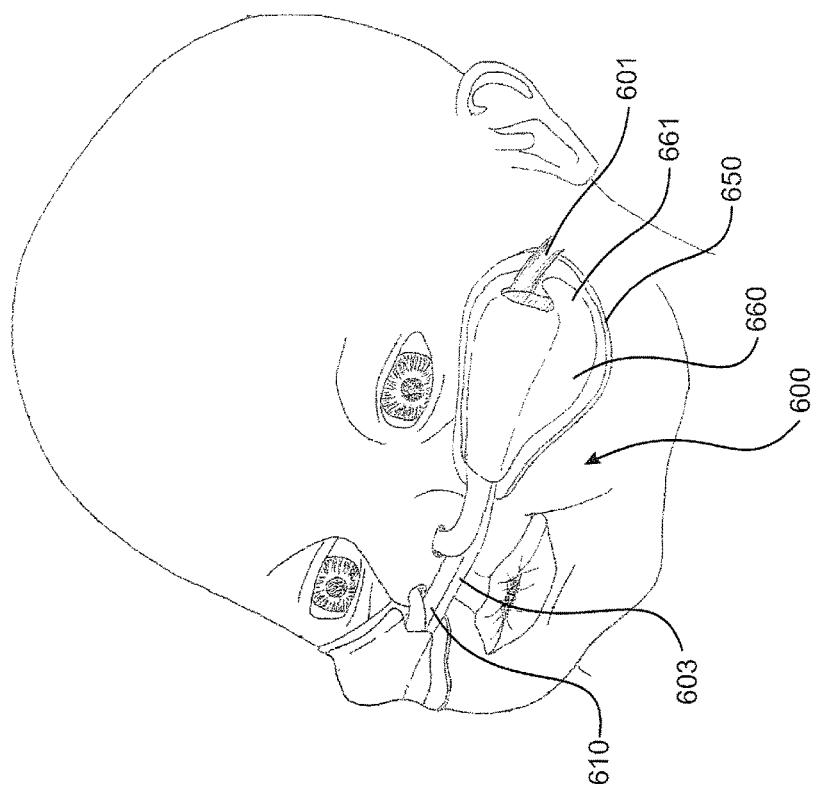
FIG. 18 shows a nasal cannula positioned in an operative position on the face of a user, the cannula positioned according to an embodiment of the sixth aspect.
Figure 20:
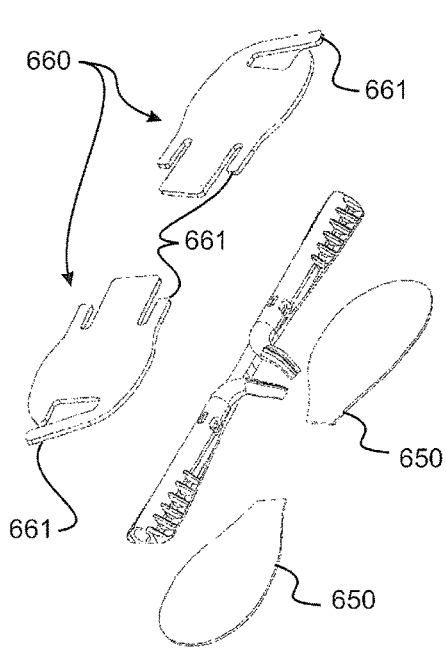
FIG. 20 shows an exploded perspective view of an embodiment according to the sixth aspect and its constituent assembly components.
Figure 21:
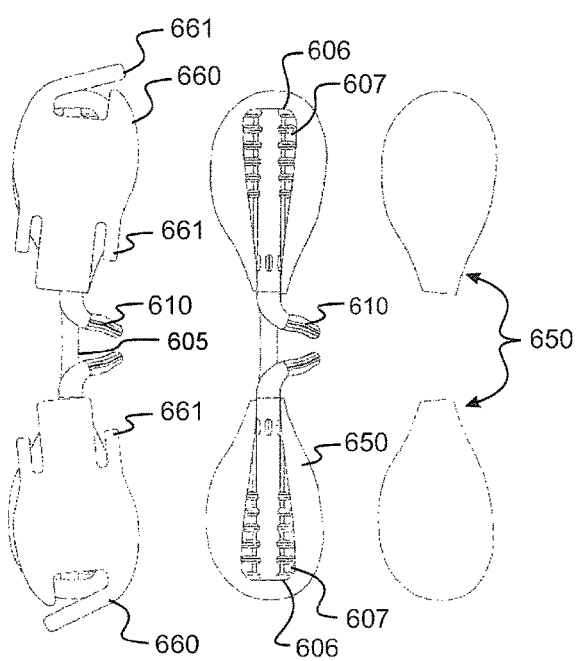
FIG. 21 shows the relative layers of an embodiment according to the sixth aspect, from right to left (user not shown).

A securement system for securing a user interface and/or user interface tubing to a patient is illustrated in FIGS. 15 to 17. The securement system 500 is illustrated supporting a nasal cannula on an infant's face. The securement system includes a backing or harness 503. A pair of outriggers 506 project outwardly from the backing 503. The backing 503 includes a housing. The housing may incorporate ribbing 507. The securement system secures prongs and each prong defines a lumen that extends between a user end 510 and a tube end of the prong.

Beneficially, the system provides for a generally more rapid and improved or simplified ease of installation of a user interface into an operational position on a user. Further, these benefits may also contribute to improved or simplified ease of application of alternative user interfaces or removal of a user interface from a user when cycling a user between different therapies (such as gas treatments, e.g. CPAP or high-flow applications).

Certain user interfaces may be provided specifically for interaction or accommodation with the system of the described embodiments. Alternatively, non-modified user interfaces can be accommodated by the described embodiments and can also be positioned relatively easily and with a minimum of time involved in an installation procedure.

In various embodiments provided by the securement system, such a system may provide for quick location of an interface to a user, and may provide for the secured positioning of the interface.

The ease with which a user interface may be positioned for a user is particularly useful. Providing a system whereby a carer (e.g. nurse) is able to apply the securement system with a single hand or single handedly, particularly where the interface user is an infant, is particularly advantageous.

In addition, in another embodiment, the securement system provides for a first level of securement of a user interface to a user. For example, such a first level of securement may be that as shown by FIGS. 15 to 17. Where a user requires additional or heightened security of user interface positioning or securement, a secondary level of interface securement can be utilized. Such an additional level may include application of an over patch, such as that provided, for example, by patch 660. Such a patch 660 may be an adhesive patch and can be installed over the top of the user interface and/or tubing and adhered to a portion of the dermal patch 550.

The securement system 500 comprises a two-part releasable attachment or connection arrangement 551. The releasable connection arrangement 551 acts between a pair of patches that are affixed to the patient and the user interface respectively.

The first patch is a dermal patch 550 that is adhered or otherwise attached to the patient's skin. The dermal patch has a user side that faces the user's skin and an interface side that faces the user interface. The user side of the dermal patch 550 may be attached to the skin of a user by a dermatologically sensitive adhesive, such as a hydrocolloid. The user interface side of the dermal patch is provided with the first part 553 of the two-part releasable attachment or connection system 551.

The second patch is a user interface patch 552. The user interface patch 552 also has a patient side and an interface side. The patient side of the user interface patch 552 is disposed adjacent the dermal patch when the system 500 is engaged. The complimentary second part of the two-part releasable attachment or connection system 553 is affixed to the patient side of the user interface patch 552, so that the respective parts of the two-part releasable attachment or connection system 551 are easily engagable when the patches 550, 552 are brought together. The interface side of the user interface patch 552 is affixed to the user interface. The user interface patch may be integrated with or suitably adhered to the user interface.

A part or corner of the user interface patch 552 may include a region that does not attach to the dermal patch 550. The general purpose of this is to allow a region (or tab) that can be more easily gripped by a user or carer for removing or detaching the interface from the dermal patch. For example, the backing 2004 may also comprise of such a corner region.

The two-part releasable attachment or connection arrangement 551 may comprise a hook and loop material (such as Velcro™), a magnet or an array of magnets disposed on the respective patches with the poles suitably arranged, an adhesive arrangement that is activated when the patches are urged together or another suitable releasable suitable coupling. The interface side of the dermal patch 550 may have one of a hook or a loop material, and the patient side of the user interface patch 552 may have the other of the hook or loop material, such that the dermal and user interface patches are releasably attachable or connectable to each other.

When we refer to a hook and loop material, we mean any one of a wide variety of area type mechanical fasteners. For example, the Velcro™ product range includes hook and loop product where the hook component includes upstanding nylon hooks (formed as cut loops through a woven backing web) which engage with any complimentary loop pile material. The Velcro™ range also includes extruded hook products, typically of a smaller size and which mate with "fluffy" non-woven fiber backing materials. These hook materials are designed to work with a range of loop substrates and in some cases, these hook materials act as loop substrates as well. Other similar systems include the Dual-Lock™ recloseable fastener system from 3M of St Paul, Minn. USA. The common feature of these releasable fastening systems is that they engage at any part of the contact between the two parts of the system. Precise alignment of individual connectors is not required because a multitude of connectors are distributed across the area of the product. A wide range of releasable fastener systems within this field may be used in the releasable attachment system for providing releasable attachment between the dermal patch and the user interface.

The first part of the two-part releasable attachment or connection system may be adhered to the user interface side of the dermal patch with a suitable adhesive and occupy up to 100% or less than about 90%, or about 85%, or about 75%, or about 60% or about 50% or about 40% or about 30% or about 20% or about 10% of the interface side surface area of the dermal patch.

According to some embodiments, the dermal patch 550 is a generally planar pad having a thickness much less than both its width and its length. In some embodiments, the pad has an overall oval shape, but may take other shapes.

The pad includes a first part 553 of the two-part releasable attachment system 551. In some embodiments, the construction of the dermal patch is such that the first part 553 of the releasable attachment system comprises a substrate and multitude of fastener elements (with effective hooks, effective loops or other elements) provided across the area of the substrate. The substrate is secured to the body of the dermal patch. In some embodiments, the substrate is secured by adhesive or by direct bonding during forming of the dermal patch.

In some embodiments, the substrate is smaller in area than the dermal patch and is located on the dermal patch so that it does not reach any edge of the dermal patch. In this way, the edge of the substrate is spread from the edge of the dermal patch all around the perimeter of the substrate.

Patches

In some embodiments, the substrate for the first part of the two-part releasable attachment system is flexible such that the plane of the substrate may bend to follow a surface that is curved in one direction. However, the substrate is typically not also stretchable to be able to follow a surface curved in two orthogonal directions. However, the pad is of the dermal patch may be stretchable and conformable to surfaces curved in more than one direction such as may be required to conform to the contours of the location of placement on the patient.

According to some embodiments, this difficulty is alleviated by providing a first part 553 of the two-part releasable attachment in a form wherein the portion of substrate is divided by at least one slit or at least one slot into regions such that that different parts of the substrate portion may bend independently and thus the overall form of the substrate portion may deform to substantially match a surface curved in two directions. This will be the case even though the substrate portion is only curved in one direction at any individual location on the substrate portion.

Examples of such forms are illustrated in FIGS. 36B to 36R. The outline of the pad of the dermal patch is illustrated in FIG. 36A. This configuration is particularly useful for the type of shapes where compound curves are most problematic, which is shapes where two or more bends in the substrate are more likely to intersect. Typically, these shapes which are fat, dumpy, stout, short and fat or short and stout, rather than elongate. For example, shapes of this type will have a short perimeter relative to the area. If they have concaves or hollows in the perimeter, then considering a virtual perimeter that is the shortest enclosing path outside the shape, the shapes will exhibit a small ratio of the square of the length of this virtual perimeter to the area of the shape. For example, the lowest ratio is exhibited by a circle at approximately 12.6:1, a square has a ratio of approximately 16:1, a two-by-one rectangle has a ratio 18:1. Whereas more elongated shapes have higher ratios, for example a five-by-one rectangle has a ratio of the square of the length of the perimeter to the area of 29:1. In some embodiments, the improvements that will be described with reference to FIGS. 36B to 36R are advantageously used for patch shapes having a ratio of the length square of the shortest enclosing perimeter to the area inside the perimeter of less than 25. In other embodiments, the improvements that will be described with reference to FIGS. 36B to 36R are advantageously used for releasable attachment substrate portions having a ratio of the length of the square of the shortest enclosing perimeter to the coverage area of the substrate less than 25.

The substrate may be formed as multiple disconnected parts as in the variation of FIG. 36A-36R, however the preferred form is for the substrate to be a single continuous part.

In some embodiments, the releasable attachment substrate portion covers substantially all of the area of the dermal patch 550. In other embodiments, the substrate portion covers most of the area of the dermal patch, for example, 50% or more of the area, 60% or more of the area, 70% or more of the area, or 80% or more of the area of the dermal patch.

Referring to FIG. 36A, in some embodiments, the dermal patch 550 includes a general elliptical or oval body 3602 with a small lateral extension 3600 at one end. In preferred embodiments, this shape has no sharp corners. Rounded or radiused corners or curved edges are less readily lifted inadvertently than sharp corners are. In many of the example embodiments of fastener substrate, the fastener substrate includes an overall shape generally matching the overall shape of the dermal patch 550, including extending into the extended portion 3600.

In the illustrated embodiments of FIGS. 36B, 36F, 36G and 36H, the substrate portion does not extend entirely to the edges of the dermal patch 550. Around at least part of the edge, a narrow zone remains between the edge of the dermal patch and the edge of the substrate. This narrow zone may extend around the full perimeter of the substrate. In some embodiments, such as the embodiment of 36B, this zone between the edge of the dermal patch 550 and the edge of the substrate may be broader at some locations than at other locations. For example, in FIG. 36B, a broader zone 3615 is provided at the end intended to be placed further from the nose. This provides for retention of the attachments in the zone nearer the nose, but allows the user to initiate peeling for release of the releasable fastener at the zone further from the nose. A similar arrangement of substrate size and location on the dermal patch could be provided for the other examples of FIGS. 36C to 36R. For example, in each case, the example configuration could be constructed to a smaller area of the dermal patch and located closer to the nasal end of the dermal patch.

The other illustrated embodiments may also be sized to not extend to the edges of the dermal patch. Generally, in the embodiments of FIGS. 36B to 36R, the substrate portion comprises a squat overall shape, which occupies a high percentage of the area within a stretched perimeter (the shortest path enclosing the shape). Generally, the substrate portion is formed as one body, but might be formed of a small number of bodies (for example two bodies) closely interleaved, such as in FIG. 36R. Within this body, the substrate is divided into multiple portions and/or into elongate shapes by at least one slot of slit such that adjacent parts (or sub portions) of the substrate portion are opposed a cross the slit, slot or gap. Depending on the arrangements of slot, slit, gap (or slots, slits or gaps) the substrate may allow the underlying dermal patch to stretch in one or more directions in addition to curving or forming a compound curve. Referring then to the different substrate shapes and configurations, some of the salient features and characteristics will be described.

In each case, certain aspects of the embodiment are described. Many variations may be constructed using these aspects. The aspects of one embodiment may be readily combined with aspects of other embodiments. The arrangements of slits or slots may be oriented in other directions, or may be mirrored or reversed.

The substrate 3603 of FIG. 36B is essentially serpentine. The substrate has an end adjacent the first end 3304 of the dermal patch and a second end adjacent or toward the second end 3305 of the dermal patch. The substrate is formed in a series of switch back loops divided by slits 3306. The slits 3306 may be angled perpendicular to a line between ends 3304 and 3305 or at some other angle. For example, the slots 3306 may be angled such that the upper end of each slit is closer to the first end 3304 than the lower end of each slit, or vice versa that the lower end of each slit is closer to the first end 3304 than the upper end of each slit. There may be at least three slits, at least four slits, or at least five slits. The serpentine shape may provide a shortest uncut path between the first end of the substrate portion and the second end of the substrate portion that is at least twice the actual linear distance between these locations.

The series of slits in the serpentine shape provide alternating portions of the serpentine path, which may bend in different directions to allow the substrate to substantially conform to an underlying compound curve surface. For example, the loop back portions 3307 may bend independently of the straight portions 3308 and the outer surface of the pad of the dermal patch may be allowed to bend to be convex in two orthogonal directions.

The serpentine shape of the substrate 3603 includes curved or radiused corners. The curved or radiused corners are less readily lifted, for example, by inadvertent contact, than sharp corners. Similar modifications may be made to any of the embodiments illustrated in FIGS. 36B to 36R.

The substrate portion of FIG. 36C is broadly similar to the substrate portion of FIG. 36B. This substrate portion 3309 is pictured entirely covering the dermal patch. One end fills the first end 3304 of the dermal patch while the other end reaches to the other end 3305 of the dermal patch. A series of alternating slits 3310 reaching from alternating edges of the substrate portion to leave a serpentine body extending between the ends 3304 and 3305. The substrate portion illustrated in FIG. 36C exhibits essentially the same flexing characteristics as the substrate portion of FIG. 36B.

The substrate portion of FIG. 36D shares essentially the same construction with the substrate portion in FIG. 36C except that the substrate portion 3311 in FIG. 36D includes slits 3312 which are further from the nasal end 3304 at the upper ends than the lower ends, whereas the slits 3310 of the substrate portion in FIG. 36C are closer to the nasal end 3304 at their upper ends than at their lower ends.

Other similar serpentine shapes are provided by substrate portion 3313 in FIG. 36G and substrate portion 3318 in FIG. 36H. In each of these cases, narrow slots are provided to separate the substrate portion into a series of adjacent islands 3321 and 3322 respectively along the length of the substrate portion. The slots 3318, 3319 are wider than slits of the previously described embodiments. A series of narrow bridges 3323 and 3324 respectively join between the islands 3321 and 3322 such that the patch forms a continuous serpentine structure. The continuous serpentine structure or the single piece structure improves the ease with which the substrate portion may be located on the dermal patch.

In the embodiment of FIG. 36G, the slots 3319 are oriented substantially orthogonal to a line between ends 3304 and 3305 of the dermal patch. In FIG. 36H, the slots 3320 are oriented with their upper ends closer to the nasal end 3304 than their lower ends—similar to FIG. 36C. In these embodiments, the width of each bridge 3323, 3324 is much smaller than the length of the slots. For example, on average, the width of the bridge portion may be less than 0.2, or less than 0.1 of the average length of the slots.

Other serpentine embodiments will be described below with reference to FIGS. 36M, 36O and 36E.

Another arrangement of substrate including a series of islands connected by bridges is illustrated in FIG. 36F. In this embodiment, the substrate portion 3325 includes islands 3326 and slots 3327. Bridges 3328 connect between the islands. In the illustrated form, the bridges of FIG. 36F are located along the centerline between ends 3304 and 3305. This arrangement might be described as having a central member with a series of leaf portions extending from both sides of the member. In the illustrated embodiment, the slots 3327 extend inward equal distance from each edge. The slots are oriented substantially perpendicular to the line between ends 3304 and 3305. The slots 3327 extend inward from the edge in alignment on opposite sides of the axis. Alternatively, they could be staggered. As with FIGS. 36H and 36B to 36D, the slots 3327 could be oriented at a non-orthogonal angle to the line between ends 3304 and 3305.

In the arrangements of FIGS. 36B, 36C, 36D, and 36F to 36H, the slots or slits are oriented substantially parallel to each other. In the arrangement of FIG. 36E, a series of slits 3329 and 3330 extend in from opposite sides of the substrate portion. In this embodiment, a first group of slits 3329 are oriented in a non-parallel angle with respect to a second group of slits 3330. In particular, in the illustrated embodiment, slits 3329 have their upper end further from the end 3304 of the dermal patch than their lower end, while slits 3330 have their upper end closer to end 3304 than their lower end. In some embodiments, the slits 3329 and 3330 pass the centerline of the substrate portion (the centerline extending from end 3304 to 3305) such that there is no straight linear path between ends 3304 and 3305 that is uncut by a slit 3329 or 3330. The slits 3329 and 3330 form a herring bone pattern.

The embodiments described with reference to FIGS. 36B to 36H have been essentially regular patterns. FIG. 36I illustrates an embodiment with a less regular pattern. In this embodiment, the substrate portion 3331 covers substantially the entire surface of the dermal patch and is divided by an irregular arrangement of slit or slits. For example, slit 3333 extends from one edge adjacent end 3304 in approximately an S shape creating a series of interleaved fingers from either side of the substrate portion 3331. A second slit 3333 extends from an edge of the substrate adjacent end 3305 of the dermal patch. The form of this slit includes a corner or a dog leg and divides at an intersection 3334 into a cross slit 3335. Slits 3332 and 3333 divide the area of the substrate portion 3331 into regions or zones of approximately equal width, with interleaved fingers and long joining portions. In this embodiment, the slits are largely internal to the substrate portion 3331 and only connect to edges of the substrate portion 3331 at two locations.

Similar arrangements of interleaved fingers are apparent in the substrate portion 3336 of FIG. 36J and the substrate portion 3337 of FIG. 36R. In the substrate portion 3336 of FIG. 35J, a single narrow slot 3337 having a small width extends from an edge of the substrate adjacent end 305 in a tortuous path along the length of the substrate portion to end adjacent edge 3304. In this embodiment, the single slot 3337 meets the edge of substrate 3336 at only one location. The slot 3337 divides the substrate portion 3336 into two major portions, each of which includes a series of fingers 3338 and 3339 respectively. The fingers 3339 and 3338 interleave. The location of the slot 3337 and the orientation of long legs 3340 between loop back portions 3341 provides the fingers 3339 and 3338 oriented along a direction that is transverse but at an angle to a line between ends 3304 and 3305.

In an alternative embodiment as illustrated in FIG. 36R, a single serpentine slot 3342 extends from an upper edge of the substrate portion 3337 to a lower edge of the substrate portion 3337. The slot 3342 extends on a serpentine path including straight portions 3343 and loop back ends 3344. This divides the substrate portion 3337 into two laterally separated portions, each of which includes at least one elongate finger 3345. The fingers of one portion are interleaved with the finger or fingers of the other portion. In this embodiment, the interleaved fingers are oriented substantially parallel with a line extending between ends 3304 and 3305.

Another embodiment including a single slot or slit is illustrated in FIG. 36K. In this embodiment, single slit 3346 extends from an edge location adjacent end 3305 in a generally spiral configuration to end at location approximately centered within the substrate portion 3347. The spiral slit 3346 divides the substrate portion 3347 into a single continuous spiral of substrate material. In some embodiments, multiple spirals slits could commence at difference locations around the perimeter of the substrate portion 3347 dividing the substrate portion into multiple interleaved spirals of substrate material.

The embodiment of FIG. 36Q includes substantially continuously curved slits compared with the embodiments of FIGS. 36B to 36J and 36R which use predominately straight slits, albeit in some cases with curved portions. FIGS. 36K to 36P illustrate other substrate portion embodiments with curved slits.

In the embodiments of FIGS. 36K and 36L, the substrate portion 3348 and 3349 respectively are each divided by a plurality of curved slits 3350 arranged, in each case, essentially on the loci of a series of concentric circles. Some of the slits 3350 reach from edges of the substrate portions 3348 and 3349.

Other slots 3351 commence and end within the body of the substrate portion 3348 and 3359. For example, in the substrate portion 3348, slits 3351 each describe an arc through greater than 315° but less than 360°, creating circular and ring-shaped portions within the substrate portion of 3348 which connect to other portions of the substrate portion 3348 via narrow bridges. Slits 3351 in substrate portion 3349 operate similarly to create circular and ring-shaped portions connected by narrow bridges.

In FIG. 36K, the arrangement of slits 3350 and 3351, and in particular the bridges between portions thus divided by the slits is such that tortuous paths of continuous uncut material are provided between end 3305 and end 3304 of the substrate portion and the centre 3352 of the substrate portion. Whereas in FIG. 36L, the arrangement of the curved slits 3350 and the substantially circular slits 3351 is such that the bridges are substantially aligned and more direct paths are provided between at least one end 3305 of the substrate portion and the centre 3352 of the substrate portion.

Another series of embodiments is illustrated in FIG. 36N to 36P. In this series, the substrate portions 3353, 3354, 3355 and 3356 respectively are each divided by a series of narrow curved slots, with each slot extending into the body of the substrate portion from either the upper or lower edge of the substrate portion. The series of curved slots in each substrate portion are arranged in parallel. In some embodiments, the spacing between the curved slots is substantially consistent along the length of the substrate portion. In some embodiments, the slots extend across the majority of the width of the substrate portion, but not entirely across the width of the substrate portion. For example, it may extend across greater than 70%, greater than 80% or greater than 90% of the width of the substrate portion. The slots may have radiused corners at their closed end.

In the arrangement in FIG. 36M, the series of slots extend from alternating sides of the substrate portion with slots 3357 and 3358 extending from an upper edge of the substrate portion and slots 3359 and 3360 extending from a lower edge of the substrate portion. This divides the substrate portion into an essentially tortuous length. In this embodiment, the curve of each substrate slot is such that the upper and lower ends of each slot are further away from the end 3304 than the mid portions are.

In the embodiment of FIG. 36N, all four curved slots 3361 extend from the same edge of the substrate portion. This is reminiscent of a comb, with a series of fingers extending in the same direction form a single back bone. As for the embodiment 36N, in this example, the slots are curved such that their upper and lower ends are further from the first end 3304 of the dermal patch than their mid-portions are.

FIG. 36O illustrates a further embodiment similar to the embodiment in FIG. 36N. In FIG. 36O, the curved slots 3362 and 3363 extend from the lower edge and upper edge respectively of the substrate portion. The series of slots 3362 is interleaved with the series of slots 3363, leaving a serpentine or convoluted continuous path along the substrate portion. In the embodiment of FIG. 36O, the upper and lower ends of each curved slot are closer to first end 3304 than are the mid-portions of each curved slot.

Another variation is illustrated in FIG. 36P. In this embodiment, curved slots 3364 will extend from the same edge of the substrate portion. They may extend from the upper edge or the lower edge. The curved slots 3364 are all essentially arranged in a parallel configuration. The curved slots have their upper ends and lower ends closer to the first end 3304 than are their mid-portions.

Another embodiment of a user interface and/or tubing securement system is illustrated in FIGS. 18 to 23. The securement system includes a backing or harness 603. A pair of outriggers 606 project outwardly from the backing 603. The backing 603 includes a housing. The housing may incorporate ribbing 607. The securement system secures prongs and each prong defines a lumen that extends between a user end 610 and a tube end of the prong, which can couple to the interface tube 601. The securement system 600 also comprises a dermal patch 650 and a securing patch 660. The securing patch 660 extends over the user interface and/or tubing and adheres to the dermal patch 650 to secure the interface and/or tubing to the patient.

The dermal patch 650 defines a securement footprint that is attached to the patient and has a similar configuration to the corresponding dermal patch 550 in the previous securement embodiment. The user side of the dermal patch 650 is configured to attach or adhere to the user's skin.

The securing patch 660 extends over the user interface and/or associated user interface tubing and affixes to the dermal patch 650 to secure the user interface to the patient. The securing patch 660 and the dermal patch 650 are configured so that the securing patch can be contained within or bounded by the securement footprint of the dermal patch when the securement system is applied to a patient with a suitable or compatible user interface. Containing the securing patch 660 within the dermal patch 650 securement footprint can reduce the likelihood of unnecessary contact with the patient's skin and the potential for irritation. Ideally, the dermal patch 650 has the same or a greater surface area than the securing patch 660.

As with the embodiment where the interface includes a two-part releasable attachment to the dermal patch, in this embodiment including a securing patch 660, the dermal patch 650 is provided with an element of the connection system for releasably connecting with the securing patch 660. For example, the dermal patch 650 may include one part of a two-part mechanical fastener system across its surface or parts of its surface, with the securing patch 660 having the other part of the fastening system.

In this manner, the dermal patch is sized to reduce the likelihood of the taping or any additional taping to extend onto the skin of the user. Avoiding or minimizing the application, or repeated application and removal, of adhesives to a user's skin is preferred. This embodiment beneficially reduces the likelihood of repeated application of adhesive, or adhesive tape, to a user's skin for the installation and placement of a user interface into an operational position. Adhesive tapes or other dermal adhesive patches (when repeatedly applied and remove), particularly for infants, create problems. Problems include, but are not limited to, skin irritation from adhesive chemicals (or adhesive removal chemicals, such as solvents) or tape materials (e.g. due to skin sensitivities), damage to user skin due to repeated application and removal of dermal patches or tapes for positioning or re-positioning of the interface for the user. Re-positioning may be required or adjustments may be needed where treatment therapies are being cycled (i.e.

changed from one type of treatment to another, and then back again). Advantageously therefore, the described embodiments provide for a system of positioning or locating of a user interface for a user, yet reducing the likelihood of the problems associated with adhesive tapes attached to the users skin.

It should be appreciated there are a number of disadvantages and problems associated with the re-positioning of an interface, particularly an infant interface. Included is "snub nosing", epidermal abrasion, or dermal allergies from traditional taping techniques for application of user interfaces (e.g. nasal cannula) to users. Such problems are also incurred during the cycling of a user between different treatment options and, traditionally, the subsequent removal of headgear or tapes or user interfaces and then the installation of new equipment and user interfaces or interface positioning headgear or other gear. Therefore, provision of a securement system which, when applied to a user, is in a ready-to-receive mode for receiving a user interface is a useful step in progressing toward reducing the problems users have previously been faced with. Further, improving the ease of installation, both in terms of complexity as well as time and effort by a carer (e.g. nurse), is of further benefit.

The securement patch may be shaped or otherwise configured to accommodate geometric or other features of the user interface and/or associated user interface tubing. The illustrated securement patches have a plurality of wings 661 that accommodate the user interface tubing and increase the contact surface of the securing patch 660 exposed to the dermal patch 650. The securing patches illustrated in FIGS. 22 and 23 each have a pair of wings arranged at one end of the patch. The wings 661 are configured to secure to the dermal patch on either side of a user interface and/or associated user interface tubing and reduce the potential for the securing patch 660 to bunch about the interface and/or tubing.

Figure 22:
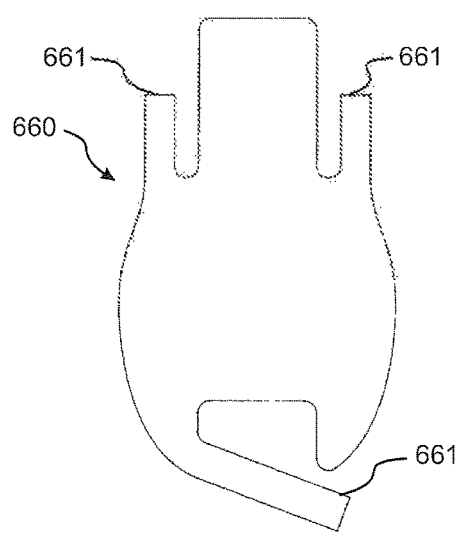
FIG. 22 illustrates one embodiment of a securing patch according to the sixth aspect.
Figure 23:
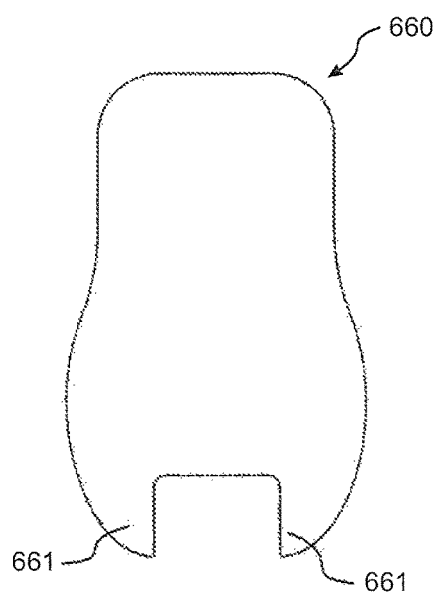
FIG. 23 illustrates another or alternative embodiment of a securing patch according to the sixth aspect.

The securement patch 661 illustrated in FIG. 22 also has a tube end wing 661. The tube end wing 661 is configured to extend under the user interface tubing and affix to the dermal patch 650 to link the ends of the securing patch 660.

Both embodiments of the securing systems can be used to secure tubing to any part of a patient's body. The embodiments illustrated in FIGS. 15 to 23 are configured to attach a user interface to a patient's face, in particular, adjacent the user's upper lip and/or cheek. The illustrated securing systems are adapted for neonatal applications.

The user side of the dermal patches 550, 650 preferably have a dermatologically sensitive adhesive (such as a hydrocolloid) that adheres the patch to a user's skin, so that application of the respective securing systems causes as little irritation as possible. The dermal patches 550, 650 preferably have sufficient surface areas to distribute the adhesive and interface retention forces over an adequate area of the user's face to reduce localized pressure build up.

The illustrated securement systems are particularly configured to receive and/or secure the nasal cannula and associated tubing disclosed previously. The tubing may extend from one or both side(s) of the user's face. Furthermore, the securing systems may be combined, so that the user interface is secured to the dermal patches by a two-part releasable attachment or connection arrangement and a securing patch arranged over the interface and/or tube.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

It should be appreciated that the various embodiments as described above and with reference to the figures can be used in combination with each other to achieve desired or beneficial results. For example the tube as described may be connected or attached to a cannula of this invention, or may be used in combination with other cannula not specifically described herein. Similarly the cannula of this invention may be used in combination with the securement system of this invention or may be used in combination or interchangeably with other retention systems. Further, the anatomically shaped prongs of this invention may be implemented in combination the tube or interface or securement system as described above or may be used in combination or interchangeably with other tubes or interfaces or securement systems. There may be particular advantages associated with combining together the various embodiments as described above.

Preferred Features

Feature SP1. A corrugated medical tube comprising: a tubular body, the body defining a lumen extending between open terminal ends of the body, and an internal form enclosed within the lumen and supportive of the tubular body, an outer-most perimeter of the internal form defining a plurality of alternating crests and troughs along a length of the tubular body.

Feature SP2. The tube in feature SP1, wherein the tubular body is an extruded tube.

Feature SP3. The tube in feature SP1 or feature SP2, wherein the tubular body is a continuous tube.

Feature SP4. The tube in any one of features SP1 to SP3, wherein the tubular body is a continuously extruded tube.

Feature SP5. The tube in any one of features SP1 to SP4, wherein the crests of the corrugated tubular body are defined by the outer-most perimeter of the internal form.

Feature SP6. The tube in any one of features SP1 to SP5, wherein the troughs of the corrugated tubular body are defined by inwardly drawn portions of the tubular body, inwardly drawn between the internal form.

Feature SP7. The tube in any one of features SP1 to SP6, wherein the internal form is a continuous length, one or a series of semi-continuous lengths or a series of discrete lengths.

Feature SP8. The tube in any one of features SP1 to SP7, wherein the internal form is one or a combination of a helical spring or a helically wound element, a helically wound skeleton or a helically wound rib, annular disks, rings, or a plurality of discrete supports interconnected or inter-connectable by one or more connecting links.

Feature SP9. The tube in any one of features SP1 to SP8, wherein the internal form is supporting of the tubular body defining the lumen within.

Feature SP10. The tube in any one of features SP1 to SP9, wherein the internal form is a skeleton or internal supporting structure, supportive of the tubular body.

Feature SP11. The tube in any one of features SP5 to SP10, wherein the tubular body is substantially unsupported in the troughs from the internal form and supported in the crests by the internal form.

Feature SP12. The tube in any one of features SP5 to SP11, wherein the wall of the tubular body is suspended between adjacent crests.

Feature SP13. The tube in any one of features SP5 to SP12, wherein the tubular body is (preferably extruded from) a polymer, such as thermoplastic polymers, preferably polymers suitable for medical breathing tubes.

Feature SP14. The tube in any one of features SP1 to SP13, wherein the tubular body is a breathable tube, or is formed of or from a breathable material, such as breathable thermoplastic polyurethane(s) or breathable polyamides.

Feature SP15. The tube in any one of features SP1 to SP14 wherein the internal form is a helically wound rib, or ribbing element.

Feature SP16. The tube in any one of features SP1 to SP15, wherein the internal form is a helically wound element having a pitch between adjacent turns of about 0.4 mm to about 2 mm, or about 0.5 to about 1.9, or about 0.6 to about 1.8, or about 0.7 to about 1.7, or about 0.8 to about 1.6, or about 0.9 to about 1.5, or about 1 to about 1.4, or about 1.1 mm to about 1.3 mm.

Feature SP17. The tube in any one of features SP1 to SP16, wherein the internal form has an outer most diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm.

Feature SP18. The tube in any one of features SP1 to SP17, wherein the internal form is a helically wound element, the element having a diameter of about 0.05 mm to 0.3 mm, or about 0.06 to about 0.29, or about 0.07 to about 0.28, or about 0.08 to about 0.27, or about 0.09 to about 0.26, or about 0.1 to about 0.25, or about 0.11 to about 0.24, or about 0.12 to about 0.23, or about 0.13 to about 0.24, or about 0.14 to about 0.23, or about 0.15 to about 0.22, or about 0.16 to about 0.24, or about 0.17 to about 0.23, or about 0.18 to about 0.22, or about 0.19 mm to about 0.21 mm.

Feature SP19. The tube in feature SP18, wherein the internal form is of a medical grade material, preferably a medical grade stainless steel.

Feature SP20. The tube in any one of features SP1 to SP19, wherein the tubular body has a thickness of about 0.05 mm to about 0.25 mm, or about 0.06 to about 0.24, or about 0.07 to about 0.23, or about 0.08 to about 0.22, or about 0.09 to about 0.21, or about 0.1 to about 0.2, or about 0.11 to about 0.19, or about 0.12 to about 0.18, or about 0.13 to about 0.17, or about 0.14 mm to about 0.16 mm.

Feature SP21. The tube in any one of features SP1 to SP20, wherein the tubular body has an internal diameter of about 1.5 mm to about 4.5 mm, or about 1.6 to about 4.4, or about 1.7 to about 4.3, or about 1.8 to about 4.2, or about 1.9 to about 4.1, or about 2 to about 4, or about 2.1 to about 3.9, or about 2.2 to about 3.8, or about 2.3 to about 3.7, or about 2.4 to about 3.6, or about 2.5 to about 3.5, or about 2.6 to about 3.4, or about 2.7 to about 3.3, or about 2.8 to about 3.2, or about 2.9 mm to about 3.1 mm.

Feature SP22. The tube in any one of features SP1 to SP21, wherein the tubular body has an external diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm.

Feature SP23. The tube in any one of features SP1 to SP22, wherein the tubular body is (preferably extruded from) one or a combination of thermoplastic elastomers, polypropylene based elastomers, liquid silicon rubbers (LSR), or breathable thermoplastic polyurethanes, or breathable polyamides, more preferably polymers may be those such as, but not limited to, polyolefins, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Feature SP24. The tube in any one of features SP1 to SP24, wherein the internal form is a plurality of rings spaced longitudinally along the lumen.

Feature SP25. The tube in feature SP24, wherein the rings are toroidal or annular in shape.

Feature SP26. The tube in any one of features SP1 to SP25, wherein the internal form is one or more discrete elements linked to one another.

Feature SP27. The tube in any one of features SP1 to SP26, wherein the internal form comprises a plurality of reinforcing ribs spaced regularly along the lumen.

Feature SP28. The tube in feature SP27, wherein each reinforcing rib comprises one turn of a helical reinforcing wire.

Feature SP29. The tube in feature SP28, wherein one turn of the helical reinforcing wire comprises one complete revolution about the lumen of the tube.

Feature SP30. The tube in feature SP28, wherein one turn of the helical reinforcing wire comprises the wire disposed between adjacent crests of the internal form.

Feature SP31. The tube in any one of features SP1 to SP30, wherein the tubular body is flexible as defined by passing the test for increase in flow resistance with bending according to ISO 5367:2000(E) (Fourth edition, 2000, Jun. 1).

Feature SP32. The tube in any one of features SP1 to SP31, wherein a terminal end of the tube is integrated with a nasal prong, the nasal prong being adapted for insertion into a user's nare as a nasal interface for delivering breathing gases to a user.

Feature SP33. The tube in any one of features SP1 to SP32, wherein the internal form is a mesh.

Feature SP34. The tube in any one of features SP1 to SP33, wherein the internal form is a conductive wire suitable for heating or sensing a property of gases within the tube.

Feature SP35. The tube in any one of features SP1 to SP34, wherein the internal form is electrically conductive, preferably the internal form is an electrically powered heater.

Feature SP36. The tube in any one of features SP1 to SP35, wherein the internal form comprises electrically conductive members or electrically powered heaters or sensors (such as flow or temperature or humidity or pressure sensors).

Feature SP37. The tube in any one of features SP1 to SP36, wherein the tube further comprises a heater, more preferably an electrically powered heater (such as a heater wire or heater circuit).

Feature SP38. The tube in any one of features SP1 to SP37, wherein the tube is a breathing tube.

Feature SP39. The tube in any one of features SP1 to SP38, wherein the ratio of pitch of the internal form to outer diameter of internal form (e.g. outer-most diameter) is about 0.10 to about 0.50, more preferably the ratio is about 0.20 to about 0.35, even more the ratio is about 0.28 or about 0.29.

Feature SP40. The tube in any one of features SP1 to SP38, wherein the ratio of the internal form diameter (e.g. diameter of actual internal form element or member) to outer diameter of internal form (e.g. outer-most diameter) is about 0.02 to about 0.10, more preferably about 0.05 to about 0.07, most preferably the ratio is 0.06.

Feature SP41. The tube in any one of features SP1 to SP38, wherein the ratio of the corrugations depth to the external (i.e. outer) tube diameter is about 0.05 to about 0.09.

Feature SP42. The tube in any one of features SP1 to SP38, wherein characteristics of the tubular body contribute to desired flexibility and/or structural support required by the tube.

Feature SPM11. A method of fabricating medical tubing, the method comprising:
providing an internal form, extruding a tubular body about the internal form, the tubular body defining a lumen enclosing the internal form.

Feature SPM12. The method in feature SPM11, further comprising:
i) applying a reduced pressure within (or to) the lumen, such that the reduced pressure draws the tubular body radially inward of the lumen and of an outer-most perimeter defined by the internal form, the outer-most perimeter of the internal form defining a plurality of alternating crests and troughs along a length of the tubular body, or
ii) applying an extension (or stretch) to at least a part or a region of the tubular body enclosing the internal form, such that release of the extension (or stretch) returns (or allows) the extended (or stretched) part or region of the tubular body to draw radially inward of the lumen and of an outer-most perimeter defined by the internal form, the outer-most perimeter defining a plurality of alternating crests and troughs along a length of the tubular body, or
iii) a combination of i) and ii).

Feature SPM13. The method in feature SPM11 or feature SPM12, wherein the tubular body is provided by extrusion or by extruding a material from a die head.

Feature SPM14. The method in any one of features SPM11 to SPM13, wherein the tubular body is extruded about the internal form and reduced pressure is applied in a manner allowing an inner face of the tubular body to become at least partly attached or bonded to at least a part of the internal form, preferably the reduced pressure differential between the pressure in the lumen and the pressure surrounding the tubular body, more preferably the pressure within (or provided to) the lumen is less than the pressure surrounding the tubular body (or the pressure surrounding the tubular body is greater than the pressure within (or provided to) the lumen).

Feature SPM15. The method in any one of features SPM11 to SPM15, wherein the tubular body is a single walled body.

Feature SPM16. The method in any one of features SPM11 to SPM16, wherein reduced pressure is applied at or adjacent formation of the lumen.

Feature SPM17. The method in feature SPM14, wherein reduced pressure is applied at or adjacent a die head.

Feature SPM18. The method in feature SPM14, wherein the lumen experiences the reduced pressure upon exit from an extrusion die head.

Feature SPM19. The method in any one of features SPM11 to SPM18, wherein the tubular body and the internal form are co-extruded.

Feature SPM110. The method in any one of features SPM11 to SPM18, wherein the tubular body so formed is corrugated.

Feature SPM111. The method in any one of features SPM11 to SPM110, wherein the crests of the corrugated tubular body so formed are defined by the outer-most perimeter of the internal form.

Feature SPM112. The method in any one of features SPM11 to SPM111, wherein the troughs of the corrugated tubular body so formed are defined by inwardly drawn portions of the tubular body, inwardly drawn between the internal form(s).

Feature SPM113. The method in any one of features SPM11 to SPM112, wherein the internal form is a skeleton or internal supporting structure, supportive of the tubular body.

Feature SPM114. The method in any one of features SPM11 to SPM113, wherein the internal form is a continuous length, one or a series of semi-continuous lengths or a series of discrete lengths.

Feature SPM115. The method in any one of features SPM11 to SPM113, wherein the internal form is a mesh.

Feature SPM116. The method in any one of features SPM11 to SPM113, wherein the internal form one or a combination of a helical spring or a helically wound element, a helically wound skeleton or a helically wound rib, annular disks, rings, or a plurality of discrete supports interconnected or inter-connectable by one or more connecting links.

Feature SPM117. The method in any one of features SPM11 to SPM116, wherein the internal form is supportive or supporting of the lumen within the tube so formed.

Feature SPM118. The method in any one of features SPM111 to SPM113 or SPM117, wherein the internal form is a helically wound element having a pitch between adjacent turns of about 0.4 mm to about 2 mm, or about 0.5 to about 1.9, or about 0.6 to about 1.8, or about 0.7 to about 1.7, or about 0.8 to about 1.6, or about 0.9 to about 1.5, or about 1 to about 1.4, or about 1.1 mm to about 1.3 mm.

Feature SPM119. The method in any one of features SPM111 to SPM113 or SPM117, wherein the internal form has an outer most diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm.

Feature SPM120. The method in feature SPM118 or feature SPM119, wherein the internal form is a helically wound element, the element having a diameter of about 0.05 mm to 0.3 mm, or about 0.06 to about 0.29, or about 0.07 to about 0.28, or about 0.08 to about 0.27, or about 0.09 to about 0.26, or about 0.1 to about 0.25, or about 0.11 to about 0.24, or about 0.12 to about 0.23, or about 0.13 to about 0.24, or about 0.14 to about 0.23, or about 0.15 to about 0.22, or about 0.16 to about 0.24, or about 0.17 to about 0.23, or about 0.18 to about 0.22, or about 0.19 mm to about 0.21 mm.

Feature SPM121. The method in feature SPM120, wherein the internal form is of a medical grade material, preferably a medical grade stainless steel.

Feature SPM122. The method in any one of features SPM11 to SPM121, wherein the tubular body has a thickness of about 0.05 mm to about 0.25 mm, or about 0.06 to about 0.24, or about 0.07 to about 0.23, or about 0.08 to about 0.22, or about 0.09 to about 0.21, or about 0.1 to about 0.2, or about 0.11 to about 0.19, or about 0.12 to about 0.18, or about 0.13 to about 0.17, or about 0.14 mm to about 0.16 mm.

Feature SPM123. The method in any one of features SPM11 to SPM122, wherein the tubular body has an internal diameter of about 1.5 mm to about 4.5 mm, or about 1.6 to about 4.4, or about 1.7 to about 4.3, or about 1.8 to about 4.2, or about 1.9 to about 4.1, or about 2 to about 4, or about 2.1 to about 3.9, or about 2.2 to about 3.8, or about 2.3 to about 3.7, or about 2.4 to about 3.6, or about 2.5 to about 3.5, or about 2.6 to about 3.4, or about 2.7 to about 3.3, or about 2.8 to about 3.2, or about 2.9 mm to about 3.1 mm.

Feature SPM124. The method in any one of features SPM11 to SPM123, wherein the tubular body has an external diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm.

Feature SPM125. The method in any one of features SPM11 to SPM124, wherein the tubular body is (preferably extruded from) a polymer, such as thermoplastic polymers, preferably polymers suitable for medical breathing tubes.

Feature SPM126. The method in any one of features SPM11 to SPM125, wherein the tubular body is (preferably extruded from) one or a combination of any one or more of thermoplastic elastomer(s), polypropylene based elastomer(s), liquid silicon rubber(s), or breathable thermoplastic polyurethane(s), or breathable polyamides, more preferably polymers may be those such as, but not limited to, polyolefins, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Feature SPM127. The method in any one of features SPM11 to SPM126, wherein the tubular body is a breathable tube, or formed of or from, a breathable material, such as breathable thermoplastic polyurethane(s) or breathable polyamides.

Feature SPM128. The method in any one of features SPM11 to SPM127, wherein the reduced pressure is applied while the tubular body is in a molten, or a semi-molten or an as yet uncured state, preferably the reduced pressure is about 0 to about −2 bar (absolute), more preferably is about 0 to about −1 bar (absolute), even more preferably down to about −0.9 bar (absolute), yet even more preferably, such reduced pressure is a pressure differential between the inside of the lumen and the region surrounding the tubular body.

Feature SPM129. The method in any one of features SPM11 to SPM128, wherein the internal form is electrically conductive, preferably the internal form is an electrically powered heater.

Feature SPM130. The method in any one of features SPM11 to SPM129, wherein the internal form comprises electrically conductive members or electrically powered heaters or sensors (such as flow or temperature or humidity or pressure sensors).

Feature SPM131. The method in any one of features SPM11 to SPM130, wherein the tube further comprises a heater, more preferably an electrically powered heater (such as a heater wire or heater circuit).

Feature SPM132. The method in any one of features SPM11 to SPM131, wherein the tubular body so formed is flexible as defined by passing the test for increase in flow resistance with bending according to ISO 5367:2000(E) (Fourth edition, 2000, Jun. 1).

Feature SPM133. The method in any one of features SPM11 to SPM132, wherein the medical tubing is a breathing tube.

Feature SPM134. The tube in any one of features SPM11 to SPM133, wherein the ratio of pitch of the internal form to outer diameter of internal form (e.g. outer-most diameter) is about 0.10 to about 0.50, more preferably the ratio is about 0.20 to about 0.35, even more the ratio is about 0.28 or about 0.29.

Feature SPM135. The tube in any one of features SPM11 to SPM134, wherein the ratio of the internal form diameter (e.g. diameter of actual internal form element or member) to outer diameter of internal form (e.g. outer-most diameter) is about 0.02 to about 0.10, more preferably about 0.05 to about 0.07, most preferably the ratio is 0.06.

Feature SPM136. The tube in any one of features SPM11 to SPM135, wherein the ratio of the corrugations depth to the external (i.e. outer) tube diameter is about 0.05 to about 0.09.

Feature SPM137. The tube in any one of features SPM11 to SPM136, wherein characteristics of the tubular body contribute to desired flexibility and/or structural support required by the tube.

Feature SP21. A medical tube comprising: a tubular body, the body defining a lumen extending between open terminal ends of the body, an internal form enclosed within the lumen and supportive of the tubular body, and a coating encapsulating the internal form, the coating securing the internal form to the tubular body.

Feature SP22. The medical tube in feature SP21, wherein the coating and the tubular body are welded along the tube.

Feature SP23. The medical tube in feature SP21 or feature SP22, wherein the coating and the tubular body are welded at discrete locations along the tube.

Feature SP24. The medical tube in feature SP22, wherein the coating and the tubular body are welded substantially continuously along the length of the tube.

Feature SP25. The medical tube in anyone of features SP21 to SP24 wherein an outer-most perimeter of the internal form defines a plurality of alternating crests and troughs along a length of the tubular body.

Feature SP26. The tube in feature SP25, wherein the crests of the corrugated tubular body are defined by the outer-most perimeter of the internal form.

Feature SP27. The tube in feature SP25 or feature SP26, wherein the troughs of the corrugated tubular body are defined by inwardly drawn portions of the tubular body, inwardly drawn between the internal form.

Feature SP28. The tube in any one of features SP21 to SP27, wherein the internal form is a continuous length, one or a series of semi-continuous lengths or a series of discrete lengths.

Feature SP29. The tube in any one of features SP21 to SP28, wherein the internal form is one or a combination of a helical spring or a helically wound element, a helically wound skeleton or a helically wound rib, annular disks, rings, or a plurality of discrete supports interconnected or inter-connectable by one or more connecting links.

Feature SP210. The tube in any one of features SP21 to SP29, wherein the internal form is supporting of the tubular body defining the lumen within.

Feature SP211. The tube in any one of features SP21 to SP210, wherein the internal form is a skeleton or internal supporting structure, supportive of the tubular body.

Feature SP212. The tube in any one of features SP25 to SP27, wherein the tubular body is substantially unsupported in the troughs from the internal form and supported in the crests by the internal form.

Feature SP213. The tube in any one of features SP25 to SP27, wherein the wall of the tubular body is suspended between adjacent crests.

Feature SP214. The tube in any one of features SP21 to SP213, wherein the tubular body is (preferably extruded from) a polymer, such as thermoplastic polymers, preferably polymers suitable for medical breathing tubes.

Feature SP215. The tube in any one of features SP21 to SP214 wherein the internal form is a helically wound rib, or ribbing element.

Feature SP216. The tube in any one of features SP21 to SP215, wherein the internal form is a helically wound strip, the coating encapsulating the strip.

Feature SP217. The tube in any one of features SP21 to SP216, wherein the internal form is a helically wound metallic wire, the coating encapsulating the wire.

Feature SP218. The tube in any one of features SP21 to SP217, wherein coating provides a surface that readily bonds with the tubular body.

Feature SP219. The tube in any one of features SP21 to SP218, wherein the internal form is a helically wound element having a pitch between adjacent turns of about 0.4 mm to about 2 mm, or about 05 to about 1.9, or about 0.6 to about 1.8, or about 0.7 to about 1.7, or about 0.8 to about 1.6, or about 0.9 to about 1.5, or about 1 to about 1.4, or about 1.1 mm to about 1.3 mm.

Feature SP220. The tube in any one of features SP21 to SP219, wherein the internal form has an outer most diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm.

Feature SP221. The tube in anyone of features SP21 to SP220, wherein the internal form is a helically wound element, the element having a diameter of about 0.05 mm to 0.3 mm, or about 0.06 to about 0.29, or about 0.07 to about 0.28, or about 0.08 to about 0.27, or about 0.09 to about 0.26, or about 0.1 to about 0.25, or about 0.11 to about 0.24, or about 0.12 to about 0.23, or about 0.13 to about 0.24, or about 0.14 to about 0.23, or about 0.15 to about 0.22, or about 0.16 to about 0.24, or about 0.17 to about 0.23, or about 0.18 to about 0.22, or about 0.19 mm to about 0.21 mm.

Feature SP222. The tube in any one of features SP21 to SP221, wherein the internal form is of a medical grade material, preferably a medical grade stainless steel.

Feature SP223. The tube in any one of features SP21 to SP222, wherein the tubular body has a thickness of about 0.05 mm to about 0.25 mm, or about 0.06 to about 0.24, or about 0.07 to about 0.23, or about 0.08 to about 0.22, or about 0.09 to about 0.21, or about 0.1 to about 0.2, or about 0.11 to about 0.19, or about 0.12 to about 0.18, or about 0.13 to about 0.17, or about 0.14 to about 0.16 mm.

Feature SP224. The tube in any one of features SP21 to SP223, wherein the tubular body has an internal diameter of about 1.5 mm to about 4.5 mm, or about 1.6 to about 4.4, or about 1.7 to about 4.3, or about 1.8 to about 4.2, or about 1.9 to about 4.1, or about 2 to about 4, or about 2.1 to about 3.9, or about 2.2 to about 3.8, or about 2.3 to about 3.7, or about 2.4 to about 3.6, or about 2.5 to about 3.5, or about 2.6 to about 3.4, or about 2.7 to about 3.3, or about 2.8 to about 3.2, or about 2.9 mm to about 3.1 mm.

Feature SP225. The tube in any one of features SP21 to SP224, wherein the tubular body has an external diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm.

Feature SP226. The tube in any one of features SP21 to SP225, wherein the tubular body is (preferably extruded from) one or a combination of thermoplastic elastomers, polypropylene based elastomers, liquid silicon rubber(s), or breathable thermoplastic polyurethanes, more preferably polymers may be those such as, but not limited to, polyolefin's, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Feature SP227. The tube in any one of features SP21 to SP226, wherein the internal form is a plurality of rings spaced longitudinally along the lumen.

Feature SP228. The tube in feature SP227, wherein the rings are toroidal or annular in shape.

Feature SP229. The tube in any one of features SP21 to SP228, wherein the internal form is one or more discrete elements linked to one another.

Feature SP230. The tube in any one of features SP21 to SP229, wherein the internal form comprises a plurality of reinforcing ribs spaced regularly along the lumen.

Feature SP231. The tube in feature SP230, wherein each reinforcing rib comprises one turn of a helical reinforcing wire.

Feature SP232. The tube in feature SP231, wherein one turn of the helical reinforcing wire comprises one complete revolution about the lumen of the tube.

Feature SP233. The tube in feature SP231, wherein one turn of the helical reinforcing wire comprises the wire disposed between adjacent crests of the internal form.

Feature SP234. The tube in any one of features SP2 to SP233, wherein the tubular body is flexible as defined by passing the test for increase in flow resistance with bending according to ISO 5367:2000(E) (Fourth edition, 2000, Jun. 1).

Feature SP235. The tube in any one of features SP21 to SP234, wherein a terminal end of the tube is integrated with a nasal prong, the nasal prong being adapted for insertion into a user's nare as a nasal interface for delivering breathing gases to a user.

Feature SP236. The tube in any one of features SP21 to SP235, wherein the internal form is a mesh.

Feature SP237. The tube in any one of features SP21 to SP236, wherein the internal form is a conductive wire suitable for heating or sensing a property of gases within the tube.

Feature SP238. The tube in any one of features SP21 to SP237, wherein the internal form is electrically conductive, preferably the internal form is an electrically powered heater.

Feature SP239. The tube in any one of features SP21 to SP238, wherein the internal form comprises electrically conductive members or electrically powered heaters or sensors (such as flow or temperature or humidity or pressure sensors).

Feature SP240. The tube in any one of features SP21 to SP239, wherein the tube further comprises a heater, more preferably an electrically powered heater (such as a heater wire or heater circuit).

Feature SP241. The tube in any one of features SP21 to SP240, wherein the tube is a breathing tube.

Feature SP242. The tube in any one of features SP21 to SP241, wherein the ratio of pitch of the internal form to outer diameter of internal form (e.g. outer-most diameter) is about 0.10 to about 0.50, more preferably the ratio is about 0.20 to about 0.35, even more the ratio is about 0.28 or about 0.29.

Feature SP243. The tube in any one of features SP21 to SP242, wherein the ratio of the internal form diameter (e.g. diameter of actual internal form element or member) to outer diameter of internal form (e.g. outer-most diameter) is about 0.02 to about 0.10, more preferably about 0.05 to about 0.07, most preferably the ratio is 0.06.

Feature SP244. The tube in any one of features SP21 to SP243, wherein the ratio of the corrugations depth to the external (i.e. outer) tube diameter is about 0.05 to about 0.09.

Feature SP245. The tube in any one of features SP21 to SP244, wherein characteristics of the tubular body contribute to desired flexibility and/or structural support required by the tube.

Feature STM21. A method of fabricating medical tubing, the method comprising: providing an internal form encapsulated in a coating, and providing a tubular body about the internal form, the tubular body defining a lumen enclosing the internal form, the tubular body being provided about the internal form such that the coating and an internal surface of the tubular body bond together, wherein the internal form remains encapsulated.

Feature STM22. The method in feature STM21 wherein the step of providing an internal form comprises providing an elongate form encapsulated within a coating suitable for application in medical tubing, and fabricating a supportive internal form for a medical tube from the coated elongate form.

Feature STM23. The method in feature STM22, wherein the uncoated elongate form is dipped in a bath of coating material to apply the encapsulating coating.

Feature STM24. The method in feature STM23, wherein the bath contains a molten polymer grade at a temperature above about 150° C.

Feature STM25. The method in any one of features STM22 to STM24, wherein the internal form is fabricated by spirally winding the elongate form into a helical form.

Feature STM26. The method in any one of features STM22 to STM25 comprising: providing an uncoated elongate form, encapsulating the elongate form in a coating suitable for application in medical tubing.

Feature STM27. The method in any one of features STM21 to STM26 comprising:
a) applying a reduced pressure within (or to) the lumen, such that the reduced pressure draws the tubular body radially inward, or
b) applying an extension (or stretch) to at least a part or a region of the tubular body enclosing the internal form, such that release of the extension (or stretch) returns (or allows) the extended (or stretched) part or region of the tubular body to draw radially inward, or
c) a combination of a) and b).

Feature STM28. The method in feature STM27, wherein the tubular body is drawn radially inward of the lumen and of an outer-most perimeter defined by the internal form, the outer-most perimeter defining a plurality of alternating crests and troughs along a length of the tubular body to form a corrugated tube.

Feature STM29. The method in any one of features STM21 to STM28, wherein the tubular body is provided by extrusion or by extruding a material from a die head.

Feature STM210. The method in any one of features STM21 to STM29, wherein the tubular body is extruded about the internal form and a reduced pressure is applied in a manner allowing an inner face of the tubular body to become at least partly attached or bonded to at least a part of the coating, preferably the reduced pressure creates a differential between the pressure in the lumen and the pressure surrounding the tubular body, more preferably the pressure within (or provided to) the lumen is less than the pressure surrounding the tubular body (or the pressure surrounding the tubular body is greater than the pressure within (or provided to) the lumen).

Feature STM211. The method in any one of features STM21 to STM210, wherein the tubular body is provided about the internal form at a temperature that causes the at least a portion of the coating and the tubular body to bond.

Feature STM212. The method in any one of features STM21 to STM211, wherein the tubular body is provided about the internal form at a temperature allowing welding of the coating and the internal form.

Feature STM213. The method in feature STM211 or STM212, wherein the tubular body at least partially fuses with the coating.

Feature STM214. The method in any one of features STM21 to STM213, wherein the tubular body is a single walled body.

Feature STM215. The method in any one of features STM21 to STM214, wherein a reduced pressure is applied at or adjacent formation of the lumen.

Feature STM216. The method in feature STM215, wherein the reduced pressure is applied at or adjacent a die head.

Feature STM217. The method in feature STM216, wherein the lumen experiences the reduced pressure upon exit from an extrusion die head.

Feature STM218. The method in any one of features STM21 to STM217, wherein the tubular body is extruded simultaneously with fabrication of the internal form from the elongate form.

Feature STM219. The method in any one of features STM21 to STM218, wherein the tubular body so formed is corrugated.

Feature STM220. The method in feature STM219, wherein the crests of the corrugated tubular body so formed are defined by the outer-most perimeter of the internal form.

Feature STM221. The method in features STM29 or STM220, wherein the troughs of the corrugated tubular body so formed are defined by inwardly drawn portions of the tubular body, inwardly drawn between the internal form(s).

Feature STM222. The method in any one of features STM21 to STM221, wherein the internal form is a skeleton or internal supporting structure, supportive of the tubular body.

Feature STM223. The method in any one of features STM21 to STM222, wherein the internal form is a continuous length, one or a series of semi-continuous lengths or a series of discrete lengths.

Feature STM224. The method in any one of features STM21 to STM223, wherein the internal form one or a combination of a helical spring or a helically wound element, a helically wound skeleton or a helically wound rib, annular disks, rings, or a plurality of discrete supports interconnected or inter-connectable by one or more connecting links.

Feature STM225. The method in any one of features STM21 to STM224, wherein the internal form is supportive or supporting of the lumen within the tube so formed.

Feature STM226. The method in any one of features STM21 to STM225, wherein the internal form comprises a helically wound element having a pitch between adjacent turns of about 0.4 mm to about 2 mm, or about 0.5 to about 1.9, or about 0.6 to about 1.8, or about 0.7 to about 1.7, or about 0.8 to about 1.6, or about 0.9 to about 1.5, or about 1 to about 1.4, or about 1.1 mm to about 1.3 mm.

Feature STM227. The method in any one of features STM21 to STM226, wherein the internal form has an outer most diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm.

Feature STM228. The method in anyone of features STM21 to STM227, wherein the internal form is a helically wound element, the element having a diameter of about 0.05 mm to 0.3 mm, or about 0.06 to about 0.29, or about 0.07 to about 0.28, or about 0.08 to about 0.27, or about 0.09 to about 0.26, or about 0.1 to about 0.25, or about 0.11 to about 0.24, or about 0.12 to about 0.23, or about 0.13 to about 0.24, or about 0.14 to about 0.23, or about 0.15 to about 0.22, or about 0.16 to about 0.24, or about 0.17 to about 0.23, or about 0.18 to about 0.22, or about 0.19 mm to about 0.21 mm.

Feature STM229. The method in anyone of features STM21 to STM228, wherein the internal form is of a medical grade material, preferably a medical grade stainless steel coated with a suitable material, preferably a polymer grade or a stainless steel.

Feature STM230. The method in any one of features STM21 to STM229, wherein the tubular body has a thickness of about 0.05 mm to about 0.25 mm, or about 0.06 to about 0.24, or about 0.07 to about 0.23, or about 0.08 to about 0.22, or about 0.09 to about 0.21, or about 0.1 to about 0.2, or about 0.11 to about 0.19, or about 0.12 to about 0.18, or about 0.13 to about 0.17, or about 0.14 mm to about 0.16 mm.

Feature STM231. The method in any one of features STM21 to STM230, wherein the tubular body has an internal diameter of about 1.5 mm to about 4.5 mm, or about 1.6 to about 4.4, or about 1.7 to about 4.3, or about 1.8 to about 4.2, or about 1.9 to about 4.1, or about 2 to about 4, or about 2.1 to about 3.9, or about 2.2 to about 3.8, or about 2.3 to about 3.7, or about 2.4 to about 3.6, or about 2.5 to about 3.5, or about 2.6 to about 3.4, or about 2.7 to about 3.3, or about 2.8 to about 3.2, or about 2.9 mm to about 3.1 mm.

Feature STM232. The method in any one of features STM21 to STM231, wherein the tubular body has an external diameter of about 1.6 mm to about 4.6 mm, or about 1.7 to about 4.5, or about 1.8 to about 4.4, or about 1.9 to about 4.3, or about 2 to about 4.2, or about 2.1 to about 4.1, or about 2.2 to about 4, or about 2.3 to about 3.9, or about 2.4 to about 3.8, or about 2.5 to about 3.7, or about 2.6 to about 3.6, or about 2.7 to about 3.5, or about 2.8 to about 3.4, or about 2.9 to about 3.3, or about 3 mm to about 3.2 mm.

Feature STM233. The method in any one of features STM21 to STM232, wherein the tubular body is (preferably extruded from) a polymer, such as thermoplastic polymers, preferably polymers suitable for medical breathing tubes.

Feature STM234. The method in any one of features STM21 to STM233, wherein the tubular body is (preferably extruded from) one or a combination of any one or more of thermoplastic elastomer(s), polypropylene based elastomer(s), liquid silicon rubber(s), or breathable thermoplastic polyurethane(s), more preferably polymers may be those such as, but not limited to, polyolefin's, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Feature STM235. The method in any one of features STM21 to STM234, wherein the reduced pressure is applied while the tubular body is in a molten, or a semi-molten or an as yet uncured state, preferably the reduced pressure is about 0 to about −2 bar (absolute), more preferably is about 0 to about −1 bar (absolute), even more preferably down to about −0.9 bar (absolute), yet even more preferably, such reduced pressure is a pressure differential between the inside of the lumen and the region surrounding the tubular body.

Feature STM236. The method in any one of features STM21 to STM235, wherein the internal form is electrically conductive, preferably the internal form is an electrically powered heater.

Feature STM237. The method in any one of features STM21 to STM236, wherein the internal form comprises electrically conductive members or electrically powered heaters or sensors (such as flow or temperature or humidity or pressure sensors).

Feature STM238. The method in any one of features STM21 to STM237, wherein the tube further comprises a heater, more preferably an electrically powered heater (such as a heater wire or heater circuit).

Feature STM239. The method in any one of features STM21 to STM238, wherein the tubular body so formed is flexible as defined by passing the test for increase in flow resistance with bending according to ISO 5367:2000(E) (Fourth edition, 2000, Jun. 1).

Feature STM240. The method in any one of features STM21 to STM239, wherein the medical tubing is a breathing tube.

Feature STM241. The method in any one of features STM21 to STM240, wherein the tube is formed by co-extruding at least one helical reinforcing element together with a tubular body, the tubular body having a continuous wall.

Feature STM242. The method in feature STM241, wherein a vacuum is applied to a lumen region of the extruded tubular body, such that, the continuous wall forms corrugations about the internal form.

Feature STM243. The method in feature STM241 or feature STM242, wherein the continuous wall being extruded is a single wall.

Feature STM244. The tube in any one of features STM21 to STM243, wherein the ratio of pitch of the internal form to outer diameter of internal form (e.g. outer-most diameter) is about 0.10 to about 0.50, more preferably the ratio is about 0.20 to about 0.35, even more the ratio is about 0.28 or about 0.29.

Feature STM245. The tube in any one of features STM21 to STM244, wherein the ratio of the internal form diameter (e.g. diameter of actual internal form element or member) to outer diameter of internal form (e.g. outer-most diameter) is about 0.02 to about 0.10, more preferably about 0.05 to about 0.07, most preferably the ratio is 0.06.

Feature STM246. The tube in any one of features STM21 to STM245, wherein the ratio of the corrugations depth to the external (i.e. outer) tube diameter is about 0.05 to about 0.09.

Feature STM247. The tube in any one of features STM21 to STM246, wherein characteristics of the tubular body contribute to desired flexibility and/or structural support required by the tube.

Feature ST31. A medical tube comprising: a tubular body, the body defining a lumen extending between open terminal ends of the body, and an internal form enclosed within the lumen and supportive of the tubular body.

Feature ST32. The tube in feature ST31, wherein an outer-most perimeter of the internal form defines a plurality of alternating crests and troughs along a length of the tubular body.

Feature ST33. The tube in feature ST31 or ST32, wherein the internal form is encapsulated in a coating, the coating securing the internal form to the tubular body.

Feature STM31. A method of fabricating medical tubing, the method comprising:
providing an internal form, providing a tubular body about the internal form, the tubular body defining a lumen enclosing the internal form, and i) applying a reduced pressure within (or to) the lumen, or ii) applying an extension (or stretch) to at least a part or a region of the tubular body enclosing the internal form, or iii) a combination of i) and ii).

Feature STM32. The method in feature STM31, wherein applying a greater reduced pressure or a greater extension (or stretch) or a combination of both draws the tubular body radially inward of the lumen along a length of the tubular body and of an outer-most perimeter defined by the internal form when the greater reduced pressure is applied or the extension (or stretch) is released or both, the outer-most perimeter of the internal form then defining a plurality of alternating crests and troughs Feature STM33. The method in features STM31 or STM32, wherein the internal form is encapsulated in a coating, the tubular body being provided about the internal form such that the coating and an internal surface of the tubular body bond together, wherein the internal form remains encapsulated.

Feature TA1. A securement system for a user interface and/or user interface tubing comprising:
a dermal patch defining a securement footprint, the dermal patch having a user side and an interface side, the user side of the dermal patch being configured to attach or adhere to a user's skin, and a securing patch, at least a part of the securing patch being configured to extend over a user interface and/or associated user interface tubing and affixes to the user interface side of the dermal patch to secure the user interface to the user, the securing patch and the dermal patch being configured so that the securing patch can be contained within or bounded by the securement footprint of the dermal patch when the securement system is applied to a patient with a suitable or compatible user interface.

Feature TA2. The securement system in feature TA1 wherein the dermal patch has the same or a greater surface area than the securing patch.

Feature TA3. The securement system in feature TA1 or feature TA2 wherein the securement patch is shaped or otherwise configured to accommodate geometric or other features of the user interface and/or associated user interface tubing.

Feature TA4. The securement system in any one of features TA1 to TA3 wherein the securement patch has at least one wing.

Feature TA5. The securement system in any one of features TA1 to TA4 wherein the securement patch has a pair of wings arranged at one end of the patch, the wings are configured to secure to the dermal patch on either side of a user interface and/or associated user interface tubing.

Feature TA6. The securement system in anyone of features TA1 to TA5 wherein the securement patch has a tube end wing, the tube end wing being configured to extend, or for extending, under the user interface tubing and affix to the dermal patch.

Feature TA7. The securement system in any one of features TA1 to TA6 wherein the user side of the dermal patch has a dermatologically sensitive adhesive (such as a hydrocolloid for example) that attaches or adheres the dermal patch to a user's skin.

Feature TA8. The securement system in any one of features TA1 to TA7 wherein the dermal patch has a surface of sufficient area such that, the surface distributes pressure the attachment or adhering forces across the user's skin.

Feature TA9. The securement system in any one of features TA1 to TA8 wherein the dermal patch is configured to attach or adhere to a user's face.

Feature TA10. The securement system in anyone of features TA1 to TA9 wherein the dermal patch is configure to attach or adhere to a user's face adjacent the user's upper lip and/or cheek.

Feature TA11. The securement system in any one of features TA1 to TA10 wherein the securement system is configured to receive and/or secure a nasal cannula and/or associated tubing, the tubing extending from one or both sides of a user's face.

Feature TA12. The securement system in any one of features TA1 to TA11 wherein the securement system is configured for use with an infant or neonatal infant.

Feature TA13. The securement system in any one of features TA1 to TA12 wherein the securement system is configured for use with a cannula as further defined by any one or more of COM1-COM17, or COMM11-COMM19, or COM21-COM216.

Feature TA14. The securement system in any one of features TA1 to TA13 wherein the securement system is configured for use with a tube as defined by any one or more of SP1-SP38, or SP21-SP241, or ST31-ST33.

Feature COM1. A nasal cannula arrangement comprising: at least one nasal prong, the prong having a gas(es) outlet adapted to be inserted into a user's nare and a gas(es) inlet fluidly connected to the gas(es) outlet, and a corrugated gas(es) delivery tube, the tube comprising a tubular body defining a lumen and an internal form enclosed within the lumen, the internal form supportive of the tubular body, an outer-most perimeter of the internal form defining a plurality of alternating crests and troughs along a length of the tubular body, wherein the gas(es) inlet of the nasal prong is formed integrally with a terminal end of the tube so that the tube lumen is fluidly connected to the gas(es) outlet of the nasal prong.

Feature COM2. The nasal cannula in feature COM1, wherein the nasal prong is shaped to substantially conform anatomically to the interior of a user's nose or nare.

Feature COM3. The nasal cannula in feature COM1 or feature COM2, wherein the nasal prong is curved, or otherwise shaped or configured, to avoid a user's septum.

Feature COM4. The nasal cannula in any one of features COM1 to COM3, wherein the nasal cannula has a substantially planar or flat or contoured backing configured to rest on a user's face, preferably as a stabilizer of the prong in the nare of a user.

Feature COM5. The nasal cannula in feature COM4, wherein one or more ribs extend between a front face of the backing and the cannula, the ribs providing a contact surface for tape or other suitable retainer employed to fasten or attach the cannula to a user's face, preferably the tape comprises adhesive portions or is an adhesive tape or a contact adhesive tape.

Feature COM6. The nasal cannula in any one of features COM1 to COM5, wherein two nasal prongs are formed integrally with a single corrugated delivery tube.

Feature COM7. The nasal cannula in any one of features COM1 to COM6, wherein the cannula comprises a pair of nasal prongs, each prong formed integrally with, or may be attached (or attachable) or connected (or connectable) to a terminal end of a pair of gas(es) delivery tube.

Feature COM8. The nasal cannula in any one of features COM1 to COM7, wherein the cannula arrangement is formed of a polymer, such as a thermoplastic polymer, preferably a polymer or polymers suitable for medical breathing tubes.

Feature COM9. The nasal cannula in any one of features COM1 to COM8, wherein the cannula arrangement is formed of one or a combination of any one or more of thermoplastic elastomer(s), polypropylene based elastomer(s), liquid silicon rubber(s), or breathable thermoplastic polyurethane(s), or breathable polyamides, more preferably polymers may be those such as, but not limited to, polyolefins, thermoplastic elastomers, or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Feature COM10. A user interface comprising a pair of nasal cannula in any one of features COM1 to COM9.

Feature COM11. The user interface in feature COM3, wherein the nasal prongs of each nasal cannula are disposed adjacent each other and the respective delivery tubes extend in opposite directions away from the nasal prongs.

Feature COM12. The user interface in feature COM4, further comprising a harness, the harness extending between and coupling the nasal cannula.

Feature COM13. The nasal cannula in any one of features COM1 to COM12, wherein the tube is a breathing tube.

Feature COM14. The nasal cannula in any one of features COM1 to COM13, wherein the tube is as defined by any one or more of SP1-SP38, or SP21-SP241, or ST31-ST33.

Feature COM15. The nasal cannula in any one of features COM1 to COM14, wherein the tube is connected to the gas inlet of the nasal prong (or both prongs) from one side (e.g. the left or the right) of the cannula.

Feature COM16. The nasal cannula in any one of features COM1 to COM14, wherein the tube is connected to the gas inlet of the nasal prongs from both sides of the cannula (e.g. both the left side and the right side)

Feature COM17. The nasal cannula in any one of features COM1 to COM16, wherein the cannula is an inant (or neonatal) nasal cannula.

Feature COMM11. A method of fabricating a nasal cannula, the method comprising: providing an internal form, extruding a tubular body about the internal form, the tubular body defining a lumen enclosing the internal form, and attaching a nasal cannula thereto.

Feature COMM12. The method in feature COMM11, further comprising:

i) applying a reduced pressure within (or to) the lumen, such that the reduced pressure draws the tubular body radially inward of the lumen and of an outer-most perimeter defined by the internal form, the outer-most perimeter of the internal form defining a plurality of alternating crests and troughs along a length of the tubular body, or ii) applying an extension (or stretch) to at least a part or a region of the tubular body enclosing the internal form, such that release of the extension (or stretch) returns (or allows) the extended (or stretched) part or region of the tubular body to draw radially inward of the lumen and of an outer-most perimeter defined by the internal form, the outer-most perimeter defining a plurality of alternating crests and troughs along a length of the tubular body, or iii) a combination of i) and ii).

Feature COMM13. The method in feature COMM11 or feature COMM12, wherein the method comprises overmoulding a nasal prong over a terminal end of the tubular body.

Feature COMM14. The method in any one of features COMM11 to COMM13, wherein a terminal end of the tube so formed by the tubular body is located in a mould or a form for moulding or forming of a nasal cannula, preferably the mould or form is closed and the nasal cannula is overmoulded or formed over the or a terminal end of the tube.

Feature COMM15. The method in any one of features COMM11 to COMM14, wherein the nasal cannula is a polymer, such as thermoplastic polymers, preferably polymers suitable for medical breathing tubes.

Feature COMM16. The method in any one of features COMM11 to COMM15, wherein the nasal cannula formed from is one or a combination of any one or more of thermoplastic elastomer(s), polypropylene based elastomer(s), liquid silicon rubber(s), or breathable thermoplastic polyurethane(s), or breathable polyamides, more preferably polymers may be those such as, but not limited to, polyolefins, thermoplastic elastomers, liquid silicon rubber(s), or breathable thermoplastic elastomers, for example thermoplastic elastomer families, such as styrene block copolymers, copolyester elastomers, or thermoplastic polyolefin elastomers or thermoplastic polyurethane elastomers, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Feature COMM17. The method in any one of features COMM11 to COMM16, wherein the tubular body is a breathable tube, or formed of or from a breathable material, such as breathable thermoplastic polyurethane(s) or breathable polyamides.

Feature COMM18. The method in any one of features COMM11 to COMM17, wherein a nasal cannula mould is provided, the mould receivable of a terminal end of the tube so formed by fabrication of the tubular body, such that operation of the mould facilities moulding of the nasal cannula, a part of which is over-moulded of the tube terminal end.

Feature COMM19. The method in features COMM11 to COMM18, wherein the nasal cannula arrangement produced by the nasal cannula is fluid communication with a terminal end of the tube so formed by fabrication of the tubular body.

Feature COM21. A nasal cannula arrangement comprising: at least one nasal prong, the prong having a gas(es) outlet adapted to be inserted into a user's nare and a gas(es) inlet fluidly connected to the gas(es) outlet, and a gas(es) delivery tube, the tube comprising a tubular body defining a lumen and an internal form enclosed within the lumen, the internal form supportive of the tubular body, wherein the gas(es) inlet of the nasal prong is formed integrally with a terminal end of the tube so that the tube lumen is fluidly connected to the gas(es) outlet of the nasal prong.

Feature COM22. The nasal cannula in feature COM21, wherein an outer-most perimeter of the internal form defines a plurality of alternating crests and troughs along a length of the tubular body.

Feature COM23. The nasal cannula in feature COM21 or COM22, wherein the prong is shaped to follow the anatomical curvature of a user's nare.

Feature COM24. The nasal cannula in anyone of feature COM21 to COM23, wherein the nasal prong is curved, or otherwise shaped or configured, to avoid a user's septum.

Feature COM25. The nasal cannula in anyone of features COM21 to COM24, wherein the nasal cannula has a contoured backing or facial pad configured to rest on a user's face, preferably as a stabilizer of the prong in the nare of a user.

Feature COM26. The nasal cannula in feature COM25, wherein one or more ribs extend between a front face of the backing or facial pas and the cannula, the ribs providing a contact surface for tape or other suitable retainer employed to fasten or attach the cannula to a user's face, preferably the tape comprises adhesive portions or is an adhesive tape or a contact adhesive tape.

Feature COM27. The nasal cannula in any one of features COM21 to COM26, wherein two nasal prongs are formed integrally with a single corrugated delivery tube.

Feature COM28. The nasal cannula in any one of features COM21 to COM27, wherein the cannula arrangement is formed of a liquid silicon rubber or a polymer, such as a thermoplastic polymer, preferably a polymer or polymers suitable for medical breathing tubes.

Feature COM29. The nasal cannula in any one of features COM21 to COM28, wherein the cannula arrangement is formed of one or a combination of any one or more of thermoplastic elastomer(s), polypropylene based elastomer(s), liquid silicon rubber(s), or breathable thermoplastic polyurethane(s), more preferably polymers may be those such as, but not limited to, polyolefin's, thermoplastic elastomers, breathable polyester elastomers, or breathable thermoplastic elastomers, for example thermoplastic elastomer families, such as styrene block copolymers, copolyester elastomers, or thermoplastic polyolefin elastomers or thermoplastic polyurethane elastomers, breathable polyester elastomer, even more preferably polymers of a Shore A of about 30 to about 90, or about 30 to about 80 or about 30 to about 70, or about 30 to about 60, or about 30 to about 50 or about 30 to about 40, or about 30, or about 40, or about 50, or about 60, or about 70, or about 80, or about 90.

Feature COM210. A user interface comprising a pair of nasal cannula in any one of features COM221 to COM29.

Feature COM211. The user interface in feature COM210, wherein the nasal prongs are disposed adjacent each other and the respective delivery tubes extend in opposite directions away from the nasal prongs.

Feature COM212. The user interface in feature COM211, further comprising a harness, the harness extending between and coupling the nasal cannula.

Feature COM213. The nasal cannula in anyone of features COM21 to COM212, wherein the tube is a breathing tube.

Feature COM214. The nasal cannula in anyone of features COM21 to COM213, wherein the tube is as defined by any one or more of SP1-SP38, or SP21-SP241, or ST31-ST33.

Feature COM215. The nasal cannula in anyone of features COM21 to COM24, wherein the tube is fabricated by a method as defined by any one or more of SPM11-SPM133, or STM21-STM243, or STM31-STM33.

Feature COM216. The nasal cannula in anyone of features COM21 to COM215, wherein the prong is glued or otherwise adhered to the tube.

Feature PWL1. A nasal cannula arrangement comprising: at least one nasal prong, the prong having a gas outlet adapted to be inserted into a user's nare and a gas inlet fluidly connected to the gas outlet, the at least one nasal prong comprising a backing, the backing configured to rest on a user's face, wherein a lip extends about at least a part of the perimeter of a rear surface of the backing, the rear surface configured for receiving or retaining a user interface patch, such that in use, the user interface patch may be releasably attachable or connectable to, or with, a dermal patch affixed to a user's face.

Feature PWL2. The nasal cannula in feature PWL1, wherein the lip is a barrier.

Feature PWL3. The nasal cannula in feature PWL1 or feature PWL2, wherein the lip is deformable.

Feature PWL4. The nasal cannula in any one of features PWL1 to PWL3, wherein the lip extends at least about the perimeter of a region substantially adjacent to a prong associated with the backing.

Feature PWL5. The nasal cannula in any one of features PWL1 to PWL3, wherein the lip is a series of one or more separate lips.

Feature PWL6. The nasal cannula in feature PWL5, wherein the one or more separate lips are adjacent, or adjoining or overlapping lip portions.

Feature PWL7. The nasal cannula in any one of features PWL1 to PWL6, wherein the lip is an endless lip extending about the perimeter of the rear surface of the backing.

Feature PWL8. The nasal cannula in any one of features PWL1 to PWL7, wherein, in use, the lip substantially forms a fluid (or liquid) seal, or barrier to fluid (or liquid), between the rear surface of the backing and a cannula facing surface of the user interface patch.

Feature PWL9. The nasal cannula in any of features PWL1 to PWL8, wherein the backing is substantially planar or flat or contoured (such as a pre-formed curve) backing configured to rest on a user's face.

Feature PWL10. The nasal cannula in any of features PWL1 to PWL9, wherein the backing assists as a stabilizer of the prong(s) in the nare(s) of a user.

Feature PWL11. The nasal cannula in any of features PWL1 to PWL10, wherein the at least one backing extends laterally outward from the at least one nasal prong, away from the septum of a user.

Feature PWL12. The nasal cannula in any one of features PWL1 to PWL11, wherein the cannula is further defined by any one or more of COM1-COM17, or COMM11-COMM19, or COM21-COM216.

Feature PWL13. The nasal cannula in any of features PWL1 to PWL12, wherein the cannula is operational with the securement system as defined by any one or more of TA1-TA14.

Feature PWL14. The nasal cannula in any of features PWL1 to PWL13, wherein the user interface patch receivable or retainable on the rear surface of the backing as defined by any one or more of WP1-WP15.

Feature PWL15. The nasal cannula in any of features PWL1 to PWL14, wherein the gas inlet of the cannula is fluidly connected to or with the tube as defined by any one or more of SP1-SP38, SPM11-SPM133, SP21-SP241, STM21-STM243, ST31-ST33, STM31-STM33.

Feature PWL16. The interface in any one of features PWL1 to PWL15, wherein the at least the lip(s) is hydrophobic.

Feature PWL17. The interface in any one of features PWL1 to PWL16, wherein the at least the lip(s) comprises at least one outer perimeter lip portion and at least one inner perimeter lip portion, each of said lips provided for contacting with a user's face.

Feature WP1. A part of a releasable fastener includes a substrate portion supporting a distributed mechanical fastener across its surface, the substrate portion being flexible but substantially non-stretchable, the substrate portion being divided into multiple areas by at least one slit or at least one slot, such that the substrate may substantially conform to an underlying compound curved surface by independent bending of different divided portions of the substrate.

Feature WP2. The securement system in feature WP1 wherein the substrate portion includes a plurality of slits or slots or both which together divide the substrate portion into a serpentine body.

Feature WP3. The securement system in feature WP2 wherein the slits and/or slots are arranged in the substrate such that a first set of at least one set of slits or slots extends into the substrate from one edge of the substrate and a second set of slits or slots extends into the substrate from the other edge of the substrate, the slits or slots of a set being interleaved with the slits or slots of the other set such that a path along the substrate portion from one end to another end without crossing the slits or slots must follow a zigzag or serpentine path much longer than a direct line between the ends.

Feature WP4. A securement system in any one of features WP1 to WP3 wherein a slit or slot of the plurality of slits or slots is curved.

Feature WP5. A securement system in any one of features WP1 to WP3 wherein a plurality of the slits or slots is curved and the curved slits or slots are arranged substantially parallel.

Feature WP6. A securement system in any one of features WP1 to WP3 wherein the slits or slots are arranged in a herring bone pattern extending in from the edges of the substrate portion.

Feature WP7. A securement system in feature WP1 wherein the substrate is divided into separated portions by a serpentine slit or slot.

Feature WP8. A securement system in feature WP1 wherein the substrate portion is divided into portions by a spiral slit or slot.

Feature WP9. A securement system in feature WP1 wherein the substrate portion is divided into sub-portions by slits or slots arranged on substantially concentric circles.

Feature WP10. A securement system in feature WP9 wherein the concentric circles are centered at approximately the centre of the substrate portion.

Feature WP11. A securement system in feature WP1 wherein the slit or slots divide the substrate portion into a plurality of islands, each joined to an adjacent island or islands by a narrow bridge.

Feature WP12. A securement system in feature WP1 wherein the substrate portion is divided into portions by an S shaped slit.

Feature WP13. A securement system in feature WP1 wherein the substrate portion is divided into portions by a T shaped slit.

Feature WP14. A securement system in any one of features WP1 to WP13 wherein the substrate portion covers at least 70% of the area of the dermal patch.

Feature WP15. A securement system in any one of features WP1 to WP14 wherein for a boundary defining the shortest path around the perimeter of the substrate, the substrate portion covers at least 80% of the area within the boundary.

Feature WP16. A securement system in any one of eatures WP1 to WP15 wherein the system may be utilised in conjunction with any one or more of securement system of TA1-TA14, or the cannula of COM1-COM17, or the cannula of PWL1-PWL17, or tubes SP1-SP38 or SP21-SP241 or ST31-ST33.

The invention claimed is:
1. An interface assembly comprising:
a user interface comprising a nasal cannula arrangement comprising:
at least one nasal prong, said prong having a gas outlet adapted to be inserted into a user's nare and a gas inlet fluidly connected to the gas outlet,
a patient facing rear surface extending generally laterally outward from the at least one nasal prong, and
a lip extending about at least a portion of a perimeter of the rear surface; and
a securement system for at least one of the user interface and a component associated with the user interface, the securement system comprising a two-part releasable attachment arrangement, the two-part releasable attachment arrangement comprising:
a dermal patch and a user interface patch,
the dermal patch comprising a patient side and an interface side,
the patient side of the dermal patch configured to attach to the skin of a user,
the interface side of the dermal patch comprising a first part of the two-part releasable attachment arrangement, and
the user interface patch comprising an interface side and patient side, the patient side of the user interface patch comprising a second part of the two-part releasable attachment arrangement, the second part being complementary to the first part, the interface side of the user interface patch being attachable to at least one of the user interface and the component associated with the user interface, the rear surface of the user interface configured for receiving or retaining the user interface patch such that the user interface patch is capable of being releasably attachable or connectable to, or with, the dermal patch and the lip at least partially bounds the user interface patch, wherein the dermal patch is configured to be affixed to a user's face.

2. The interface assembly as claimed in claim 1, wherein the interface includes one or a pair of nasal prongs.

3. The interface assembly as claimed in claim 1, wherein the lip is a barrier.

4. The interface assembly as claimed in claim 1, wherein the lip is deformable.

5. The interface assembly as claimed in claim 1, wherein the lip is a continuous lip extending about the perimeter of the rear surface.

6. The interface assembly as claimed in claim 1, wherein the lip is a series of one or more separate lips.

7. The interface assembly as claimed in claim 1, wherein, in use, the lip substantially forms a fluid (e.g. liquid) seal, or barrier to fluid, between the rear surface of the nasal cannula arrangement and a cannula-facing surface of the user interface patch.

8. The interface assembly as claimed in claim 1, wherein the rear surface is contoured and configured to conform to a user's face.

9. The interface assembly as claimed in claim 1, wherein the lip is hydrophobic.

10. The interface assembly as claimed in claim 1, wherein the lip comprises at least one outer perimeter lip portion and at least one inner perimeter lip portion, each of said lip portions provided for contacting with a user's face.

11. The interface assembly as claimed in claim 1, wherein the first part of the two-part releasable attachment arrangement has a first of a hook and a loop, and the second part of the two-part releasable attachment arrangement has a second of the hook and the loop, such that the first and second parts are releasably attachable to each other.

12. The interface assembly as claimed in claim 11, wherein the first part of the two-part releasable attachment arrangement occupies less than about 90% of the interface side of the dermal patch.

13. The interface assembly as claimed in claim 1, wherein the first part of the two-part releasable attachment arrangement is adhered or adherable to the interface side of the dermal patch with an adhesive.

14. The interface assembly as claimed in claim 1, wherein the patient side of the dermal patch has a dermatologically sensitive adhesive capable of adhering the dermal patch to a user's skin.

15. The interface assembly as claimed in claim 1, wherein the securement system is configured to receive and/or secure the nasal cannula arrangement and associated tubing, the tubing configured to extend from one or both sides of a user's face.

16. The interface assembly as claimed in claim 1, wherein the securement system is configured for use with an infant or neonatal infant.

17. The interface assembly as claimed in claim 1, wherein the first part of the two-part releasable attachment arrangement includes a substrate portion secured to, or for securing to, the dermal patch.

18. The interface assembly as claimed in claim 17, wherein the substrate portion includes at least one slit or at least one slot with areas of the substrate portion separated by the slit or slot.

19. The interface assembly as claimed in claim 18, wherein the slits and/or slots are arranged in the substrate portion such that a first set of at least one set of slits or slots extends into the substrate portion from a first edge of the substrate portion and a second set of slits or slots extends into the substrate portion from a second edge of the substrate portion, the second edge opposing the first edge, the slits or slots of the first set being interleaved with the slits or slots of a second set such that a path along the substrate portion from a first end to a second end without crossing the slits or slots must follow a zigzag or serpentine path much longer than a direct line between the first end and the second end.

20. The interface assembly as claimed in claim 18, wherein the slits or slots are arranged in a herring bone pattern extending in from at least one edge of the substrate portion.

21. The interface assembly as claimed in 18, wherein the substrate portion includes a plurality of slits or slots or both which together divide the substrate portion into a serpentine body.

22. The interface assembly as claimed in claim 21, wherein at least one of the slits or slots of the plurality of slits or slots is curved.

23. The interface assembly as claimed in claim 21, wherein a plurality of the slits or slots is curved and the curved slits or slots are arranged substantially parallel.

24. The interface assembly as claimed in claim 18, wherein the slit or slots divide the substrate portion into a plurality of islands, each joined to an adjacent island or islands by a narrow bridge.

25. The interface assembly as claimed in claim 17, wherein the substrate portion is divided into separated portions by a serpentine slit or slot.

26. The interface assembly as claimed in claim 17, wherein the substrate portion is divided into portions by a spiral slit or slot.

27. The interface assembly as claimed in claim 17, wherein the substrate portion is divided into sub-portions by slits or slots arranged on substantially concentric circles.

28. The interface assembly as claimed in claim 17, wherein the substrate portion covers at least 70% of the dermal patch.

29. The interface assembly as claimed in claim 1, further comprising a tube connected to the user interface providing at least a part of a breathing circuit for a user of the user interface, wherein the tube comprises:
a tubular body defining a lumen extending between open terminal ends of the tubular body,
an internal form enclosed within the lumen and supportive of the tubular body, and
a coating encapsulating the internal form, the coating securing the internal form to the tubular body.

30. The interface assembly as claimed in claim 29, wherein the tube is a medical breathing tube.

31. The interface assembly as claimed in claim 29, wherein the coating and the tubular body of the tube are plastically welded together along the tube.

32. The interface assembly as claimed in claim 29, wherein an outer-most perimeter of the internal form defines a plurality of alternating crests and troughs along a length of the tubular body.

33. The interface assembly as claimed in claim 29, wherein the internal form is one of, or a combination of, a helical spring or a helically wound element, a helically wound skeleton or a helically wound rib, annular disks, rings, or a plurality of discrete supports interconnected or inter-connectable by one or more connecting links.

34. The interface assembly as claimed in claim 29, herein the tubular body is a breathable tube, or is formed of or from a breathable material.

35. The interface assembly as claimed in claim 29, wherein the internal form is a helically wound element having a pitch between adjacent turns of about 1 mm to about 1.5 mm.

36. The interface assembly as claimed in claim 29, wherein the internal form is a helically wound element, the helically wound element having a diameter of about 0.1 mm to about 0.4 mm.

37. The interface assembly as claimed in claim 29, wherein the internal form is a conductive wire suitable for heating or sensing a property of gases within the tube.

38. The interface assembly as claimed in claim 29, wherein the internal form is a helically wound element having a pitch and wherein a ratio of pitch of the internal form to an outer diameter of the internal form is about 0.10 to about 0.50.

39. The interface assembly as claimed in claim 38, wherein the ratio of pitch of the internal form to an outer diameter of the internal form is about 0.28.

* * * * *

UNITED STATES PATENT AND TRADEMARK OFFICE
CERTIFICATE OF CORRECTION

PATENT NO. : 10,238,828 B2
APPLICATION NO. : 13/880036
DATED : March 26, 2019
INVENTOR(S) : Mark Thomas O'Connor It is certified that error appears in the above-identified patent and that said Letters Patent is hereby corrected as shown below:

In the Specification

Column 15 Line 49, change "troughs" to --troughs.--.

Column 19 Line 46, change "users" to --user's--.

Column 36 Line 8, change "may" to --may be--.

Column 40 Line 25, change "the or" to --or the--.

Column 40 Line 59, change "avoid" to --avoided--.

Column 45 Line 9, change "that that" to --that--.

Column 51 Line 6, change "users" to --user's--.

Column 65 Line 56, change "troughs" to --troughs.--.

Column 72 Line 35, change "eatures" to --features--.

In the Claims

Column 74 Line 26, Claim 21, change "18," to --claim 18,--.

Signed and Sealed this
Third Day of September, 2019

Andrei Iancu
*Director of the United States Patent and Trademark Office*